(12) United States Patent
Ackermann et al.

(10) Patent No.: US 8,258,158 B2
(45) Date of Patent: Sep. 4, 2012

(54) HSL INHIBITORS USEFUL IN THE TREATMENT OF DIABETES

(75) Inventors: Jean Ackermann, Riehen (CH); Aurelia Conte, Basel (CH); Werner Neidhart, Hagenthal-le-Bas (FR); Matthias Nettekoven, Grenzach-Wyhlen (DE); Stanley Wertheimer, Croton, NY (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/875,446

(22) Filed: Sep. 3, 2010

(65) Prior Publication Data

US 2011/0065707 A1    Mar. 17, 2011

(30) Foreign Application Priority Data

Sep. 11, 2009   (EP) ..................... 09170071

(51) Int. Cl.
*A61K 31/445*   (2006.01)
*C07D 211/06*   (2006.01)
*C07D 401/02*   (2006.01)

(52) U.S. Cl. ........ 514/326; 546/184; 546/192; 546/207; 546/210; 514/315; 514/317

(58) Field of Classification Search ............... 546/184, 546/192, 207, 210; 514/315, 317, 326
See application file for complete search history.

(56) References Cited

U.S. PATENT DOCUMENTS 6,858,626 B2 *   2/2005   Xue et al. ................... 514/312
8,003,662 B2 *   8/2011   Blake et al. ................ 514/301

FOREIGN PATENT DOCUMENTS

WO   2010/106081   9/2010

OTHER PUBLICATIONS

Benbow, J.W. et al, Bioorganic & Medicinal Chemistry Letters, (2009) 19:8 2220-2223, xp026066471.
Wertheimer et al, Drug Discovery Today: 4:2 pp. 129-135 (2007) XP002607051.
Atrash B et al, Wiley VCH Verlag Weinheim LNKD (2001) 40:5 pp. 938-941 xp001004958.
International Search Report for PCT/EP2010/063078 dated Nov. 22, 2010.
Wang et al., Chem. Biol. 2006 vol. 13 pp. 1019-1027.
Gregoire et al., Physiol. Rev. 1998 vol. 78 pp. 783-809.
Unger et al., Annu. Rev. Med. 2002 vol. 53 pp. 319-336.
Duncan et al., 2007 Annu. Rev. Nutr. vol. 27 pp. 79-101.
Jaworski et al., 2007 Am. J. Physiol. Gastrointest. Liver Physiol. vol. 293 pp. G1-G4.
Large et al., 1998 J. Lipid. Res. vol. 39 pp. 1688-1695.
Hotamisigil, G. S., 1995, J. Clin. Invest. vol. 95 pp. 2409-2415.
Gao et al., Mol. Endocrinol. 2004 vol. 18 pp. 2024-2034.
Lopaschuk et al., Physiol. Rev. 2005 vol. 85 p. 1093.
Oliver, M. F., QJM 2006 vol. 99 pp. 701-709.
Cusi et al., J. Cardiometab. Syndr. 2009 vol. 3 pp. 141-146.
Mauriege et al., J. Physiol. Biochem. 2009 vol. 65 pp. 33-41.
Lewis et al., Dig. Dis. Sci. 2010 vol. 55 pp. 560-578.

* cited by examiner

*Primary Examiner* — Golam M M Shameem
(74) *Attorney, Agent, or Firm* — George W. Johnston; Patricia S. Rocha-Tramaloni; Gene J. Yao

(57) ABSTRACT

The present invention relates to compounds of formula (I)

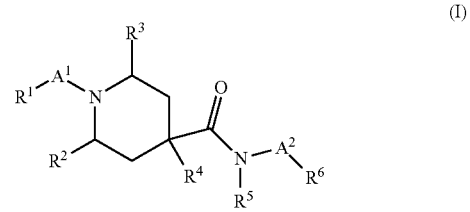

(I)

as well as pharmaceutically acceptable salts thereof, wherein $A^1, A^2, R^1, R^2, R^3, R^4, R^5$ and $R^6$ have the significance given herein.

13 Claims, No Drawings

HSL INHIBITORS USEFUL IN THE TREATMENT OF DIABETES

PRIORITY TO RELATED APPLICATION(S)

This application claims the benefit of European Patent Application No. 09170071.6, filed Sep. 11, 2009, which is hereby incorporated by reference in its entirety.

FIELD OF THE INVENTION

The present invention is concerned with novel azacyclic derivatives useful as HSL inhibitors. In particular, the invention is concerned particularly with compounds of formula (I),

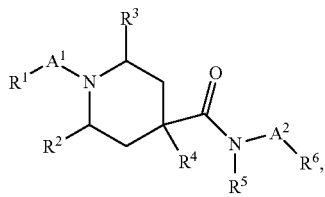

wherein $R^1, R^2, R^3, R^4, R^5, R^6, A^1, A^2$, G, and n are as defined herein.

BACKGROUND OF THE INVENTION

The main physiological role of white adipose tissue (WAT) is to supply energy when it is needed by other tissues. In mammals, white adipose tissue is the primary energy storage depot, accumulating fuel reserves in the form of triacylglycerol (TAG) during times of energy excess (Wang M. et al., Chem. Biol., 2006, 13, 1019-1027; Gregoire F. M. et al., Physiol. Rev., 1998, 78, 783-809). However, unlike TAG synthesis that also occurs at high levels in liver for very low density lipoprotein (VLDL) production, lipolysis for the provision of fatty acids as an energy source for use by other organs is unique to adipocytes. The release of free fatty acids (FFA) from TAG proceeds in an orderly and regulated manner (Unger R. H, Annu. Rev. Med. 2002, 53, 319-336; Duncan R. E. et al, 2007, Annu Rev Nutr, 27, 79-101; Jaworski K. Et al, 2007, Am J Physiol Gastrointest Liver Physiol, 293, G1-4), stimulated by catecholamines and regulated by hormones such as insulin, glucagon and epinephrine.

The most important enzyme in WAT believed responsible for hormone regulated hydrolysis of triglyceride is hormone sensitive lipase (HSL). This enzyme is also present in the liver, skeletal muscle, pancreas and adrenal glands. In the basal state, it has minimal activity against its substrate. Stimulation of adipocytes by hormones activates protein kinase A resulting in the phosphorylation of HSL and the lipid droplet coating protein perilipin. Phosphorylation of perilipin leads to its removal from the lipid droplet and migration of phosphorylated HSL from the cytosol to the lipid droplet where it catalyzes the hydrolysis of triglycerides (Wang M. et al., Chem. Biol., 2006, 13, 1019-1027).

Dysregulation of adipocyte lipolysis, resulting in elevated circulating non-esterified fatty acids (NEFA) is associated with obesity and co-morbidities including the development of type 2 diabetes (Unger R. H, Annu. Rev. Med. 2002, 53, 319-336). Obese or insulin resistant subjects have increased visceral adipose tissue depots. These depots contain elevated levels of HSL protein (Large, V. et al., 1998, J. Lipid. Res. 39, 1688-1695) and exhibit enhanced lipolytic activity as they are resistant to the insulin-mediated suppression of lipolysis. This results in increased plasma levels of free fatty acids, which further exacerbates insulin resistance due to the accumulation of triglycerides in tissues other than WAT such as liver, pancreas and muscle. The ectopic deposition of triglycerides results in pathological effects such as increased glucose production in the liver, decreased insulin secretion from the pancreas, and reduced glucose uptake and fatty acid oxidation in skeletal muscle. Thus, the elevated plasma levels of FFA due to increased HSL activity contributes to and worsens insulin resistance in obese and type 2 diabetic individuals. In addition, elevated FFA is related to increased production of the inflammatory cytokine TNF-alpha, by the adipose tissue (Hotamisigil, G. S., 1995, J. Clin. Invest. 95, 2409-2415). TNF-alpha further disrupts insulin signaling by the activation of serine kinases, such as JNK-1, which phosphorylated IRS-1 which depresses insulin signaling (Gao, Z. et. al., Mol Endocrinol, 2004, 18, 2024-2034). Thus, restoring the exaggerated plasma FFA and triglyceride levels through inhibition of HSL would reduce the accumulation of triglycerides in tissues other than WAT, such as liver, muscle and the pancreas resulting in decreased hepatic glucose output, increased muscle fatty acid oxidation and improving β-cell function. Inflammatory cytokine production would also be lessened, leading to further reductions in FFA production and improved insulin signaling. Elevated FFAs are also associated with increased cardiovascular risk, including atherosclerosis and myocardial dysfunction (Lopaschuk, et. al., Physiol Rev 2005, 85, 1093-129; Oliver, M F, QJM 2006, 99, 701-9) It has also been demonstrated that chronic low-dose lipid infusion in healthy patients induces markers of endothelial activation independent of its metabolic effects (Cusi, et. al., J. Cardiometab. Syndr. 2009, 3, 141-6). Here it was shown that modest lipid infusion elevates markers of endothelial activation-ET-1, ICAM-1, VCAM-1. Furthermore high lipolytic activity and elevated FFAs lead to increased insulin resistance and hypertension in hypertensive rats (Mauriege, et. al. J Physiol Biochem. 2009, 65, 33-41).

As HSL is major hormone regulated lipase, it is known that during insulin resistant states, the ability of insulin to suppress lipolysis is reduced, and contributes to the increased FFA, ie. lipotoxicity. These fatty acids collect in the liver and lead to increased production of TAG, which are packaged into VLDLs which are secreted. There is also an accumulation of lipid in liver, leading to a fatty liver phenotype. Lipolysis is increased during diabetes and obesity which contributes to this phenotype. Therefore, reducing the activity of HSL would decrease the release of FFA to the blood, thus limiting the supply of FFA to the liver for TAG synthesis. Thus, HSL inhibitors could have beneficial effects as treatment of NAFLD (nonalkoholic fatty liver disease) and NASH (non-alkoholic steatohepatitis) (Jeffry R. Lewis et al, Dig Dis Sci 2010, 55: 560-578).

SUMMARY OF THE INVENTION

The present invention relates to a compound of formula (I),

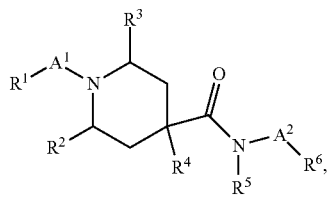

wherein

R¹ is selected from the group consisting of: dimethylpropyl, dimethylbutyl, cyclopropylalkyl, pyrazolyl, methyl-trifluoromethyl-1H-pyrazolyl, morpholinyl, phenyl, 2-chlorophenyl, 4-methylphenyl and 4-methoxyphenyl;

R² is selected from the group consisting of: hydrogen, alkyl, hydroxyalkyl and alkoxyalkyl;

R³ is selected from the group consisting of: hydrogen, alkyl, hydroxyalkyl and alkoxyalkyl;

R⁴ is selected from the group consisting of: hydrogen, halogen, alkyl, hydroxyalkyl and alkoxyalkyl;

R⁵ is hydrogen or alkyl;

R⁶ is selected from the group consisting of: 2,3-dihydrobenzofuranyl, alkylpyridin-3-yl, haloalkoxypyridin-3yl, pyridazinyl, alkoxypyridazinyl, alkyl-trifluoromethyl-1H-pyrazolyl, phenyl and substituted phenyl, wherein substituted phenyl is phenyl substituted in the 4-position with a substituent selected from the group consisting of: chlorine, isopropyl, hydroxyalkyl, isopropoxy, cycloalkylalkoxy, haloalkoxy, haloalkoxyalkyl, alkoxycarbonylalkoxy, carboxyalkoxy, hydroxyalkoxy, alkoxyhaloalkoxy and hydroxyhaloalkoxy; and optionally further substituted in another position with one substituent independently selected from the group consisting of: fluorine, trifluoromethoxy, alkoxycarbonylalkoxy and hydroxyalkoxycarbonyl;

A¹ is carbonyl or —S(O)₂—;

A² is a single bond, —CH₂CH₂— or G;

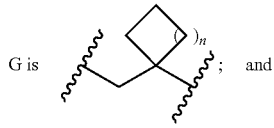

n is zero, 1, 2, 3, 4 or 5;

and pharmaceutically acceptable salts thereof;

with the proviso that, when R⁶ is phenyl or phenyl substituted in the 4-position with chlorine, A² is G;

with the further proviso that said compound is not 1-(toluene-4-sulfonyl)-piperidine-4-carboxylic acid (4-trifluoromethoxy-phenyl)-amide; 1-(toluene-4-sulfonyl)-piperidine-4-carboxylic acid [2-(4-difluoromethoxy-phenyl)-ethyl]-amide; 1-benzenesulfonyl-piperidine-4-carboxylic acid (4-isopropyl-phenyl)-amide; 1-(toluene-4-sulfonyl)-piperidine-4-carboxylic acid (4-isopropyl-phenyl)-amide; 1-(4-methoxy-benzenesulfonyl)-piperidine-4-carboxylic acid (4-trifluoromethoxy-phenyl)-amide; 1-benzenesulfonyl-piperidine-4-carboxylic acid (4-trifluoromethoxy-phenyl)-amide; 1-(4-methoxy-benzenesulfonyl)-piperidine-4-carboxylic acid (4-difluoromethoxy-phenyl)-amide; 1-(4-methoxy-benzenesulfonyl)-piperidine-4-carboxylic acid (4-isopropyl-phenyl)-amide; 1-(4-methoxy-benzenesulfonyl)-piperidine-4-carboxylic acid (4-chloro-2-fluoro-phenyl)-amide; 1-benzoyl-piperidine-4-carboxylic acid (4-isopropyl-phenyl)-amide; 1-(2-chloro-benzoyl)-piperidine-4-carboxylic acid (4-isopropyl-phenyl)-amide; 1-benzenesulfonyl-piperidine-4-carboxylic acid (1-phenyl-cyclopropylmethyl)-amide or 1-(toluene-4-sulfonyl)-piperidine-4-carboxylic acid (1-phenyl-cyclopentylmethyl)-amide.

The present invention also relates to a pharmaceutical composition comprising a therapeutically inert carrier and a compound as described above.

DETAILED DESCRIPTION OF THE INVENTION

The present invention relates in part to a compound of formula (I),

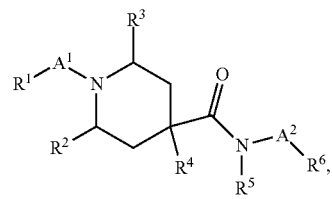

wherein

R¹ is selected from the group consisting of: dimethylpropyl, dimethylbutyl, cyclopropylalkyl, pyrazolyl, methyl-trifluoromethyl-1H-pyrazolyl, morpholinyl, phenyl, 2-chlorophenyl, 4-methylphenyl and 4-methoxyphenyl;

R² is selected from the group consisting of: hydrogen, alkyl, hydroxyalkyl and alkoxyalkyl;

R³ is selected from the group consisting of: hydrogen, alkyl, hydroxyalkyl and alkoxyalkyl;

R⁴ is selected from the group consisting of: hydrogen, halogen, alkyl, hydroxyalkyl and alkoxyalkyl;

R⁵ is hydrogen or alkyl;

R⁶ is selected from the group consisting of: 2,3-dihydrobenzofuranyl, alkylpyridin-3-yl, haloalkoxypyridin-3yl, pyridazinyl, alkoxypyridazinyl, alkyl-trifluoromethyl-1H-pyrazolyl, phenyl and substituted phenyl, wherein substituted phenyl is phenyl substituted in the 4-position with a substituent selected from the group consisting of: chlorine, isopropyl, hydroxyalkyl, isopropoxy, cycloalkylalkoxy, haloalkoxy, haloalkoxyalkyl, alkoxycarbonylalkoxy, carboxyalkoxy, hydroxyalkoxy, alkoxyhaloalkoxy and hydroxyhaloalkoxy; and optionally further substituted in another position with one substituent independently selected from the group consisting of: fluorine, trifluoromethoxy, alkoxycarbonylalkoxy and hydroxyalkoxycarbonyl;

A¹ is carbonyl or —S(O)₂—;

A² is a single bond, —CH₂CH₂— or G;

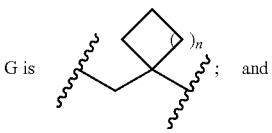

n is zero, 1, 2, 3, 4 or 5;

and pharmaceutically acceptable salts thereof; with the proviso that, when R⁶ is phenyl or phenyl substituted in the 4-position with chlorine, A² is G;

with the further proviso that said compound is not 1-(toluene-4-sulfonyl)-piperidine-4-carboxylic acid (4-trifluoromethoxy-phenyl)-amide; 1-(toluene-4-sulfonyl)-piperidine-4-carboxylic acid [2-(4-difluoromethoxy-phenyl)-ethyl]-amide; 1-benzenesulfonyl-piperidine-4-carboxylic acid (4-isopropyl-phenyl)-amide; 1-(toluene-4-sulfonyl)-piperidine-4-carboxylic acid (4-isopropyl-phenyl)-amide; 1-(4-methoxy-benzenesulfonyl)-piperidine-4-carboxylic acid (4-trifluoromethoxy-phenyl)-amide; 1-benzenesulfonyl-piperidine-4-carboxylic acid (4-trifluoromethoxy-phenyl)-amide; 1-(4-methoxy-benzenesulfonyl)-piperidine-4-carboxylic acid (4-difluoromethoxy-phenyl)-amide; 1-(4-methoxy-benzenesulfonyl)-piperidine-4-carboxylic acid (4-isopropyl-phenyl)-amide; 1-(4-methoxy-benzenesulfonyl)-piperidine-4-carboxylic acid (4-chloro-2-fluoro-phenyl)-amide; 1-benzoyl-piperidine-4-carboxylic acid (4-isopropyl-phenyl)-amide; 1-(2-chloro-benzoyl)-piperidine-4-carboxylic acid (4-isopropyl-phenyl)-amide; 1-benzenesulfonyl-piperidine-4-carboxylic acid (1-phenyl-cyclopropylmethyl)-amide or 1-(toluene-4-sulfonyl)-piperidine-4-carboxylic acid (1-phenyl-cyclopentylmethyl)-amide.

Aspects of the present invention include the compounds of formula (I) and their pharmaceutically-acceptable salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of diabetes, metabolic syndrome, dyslipidemia, atherosclerosis or obesity and the use of the said compounds, salts or esters for the production of medicaments for the treatment or prophylaxis of diabetes, metabolic syndrome, dyslipidemia, atherosclerosis or obesity.

The term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms. Examples are methyl, ethyl, propyl, isopropyl, butyl, isobutyl, tert-butyl, the isomeric pentyls, the isomeric hexyls, the isomeric heptyls and the isomeric octyls, preferably methyl, ethyl, isopropyl, tert-butyl and isomeric pentyls. Particularly preferred alkyl are methyl, isopropyl and tert-butyl.

The term "cycloalkyl", alone or in combination, signifies a cycloalkyl ring with 3 to 8 carbon atoms and preferably a cycloalkyl ring with 3 to 6 carbon atoms. Examples are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl. A preferred cycloalkyl is cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert-butoxy, preferably methoxy and isopropoxy. A particularly preferred alkoxy is isopropoxy.

The term "hydroxyalkyl", alone or in combination, signifies an alkyl group as defined before, wherein one or more hydrogen atoms is replaced by a hydroxy group. Examples of hydroxyalkyl are hydroxymethyl, hydroxyethyl, hydroxypropyl and dihydroxypropyl. A preferred hydroxyalkyl is hydroxymethyl.

The term "halogen", alone or in combination, signifies fluorine, chlorine, bromine or iodine and preferably fluorine or chlorine.

The term "haloalkoxy", alone or in combination, signifies an alkoxy group as defined before, wherein one or more hydrogen atoms are replaced by a halogen atom. Examples of haloalkyl are fluoromethoxy, difluoromethoxy, trifluoromethoxy, trifluoroethoxy, trifluoromethylethoxy, trifluorodimethylethoxy or pentafluoroethoxy. Preferred haloalkoxy is trifluoromethoxy.

The term "carbonyl", alone or in combination, signifies the —C(O)— group.

The term "carboxy", alone or in combination, signifies the —C(O)OH— group.

The term "hydroxy", alone or in combination, signifies the —OH group.

The term "sulfonyl", alone or in combination, signifies the —S(O)$_2$— group.

The term "protecting group" refers to groups which are used to block the reactivity of functional groups such as amino groups or hydroxy groups. Examples of protecting groups are tert-butyloxycarbonyl (Boc), benzyloxycarbonyl (Cbz), fluorenylmethyloxycarbonyl (Fmoc) or benzyl (Bn). Preferred protecting groups are tert-butyloxycarbonyl (Boc) and benzyl (Bn).

Cleavage of protecting group can be done using standard methods known by the man skilled in the art such as hydrogenation or in the presence of an acid, e.g. HCl or TFA, preferably TFA, or a base, e.g. triethylamine.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particularly preferred pharmaceutically acceptable salts of compounds of formula (I) are the hydrochloride salts, methanesulfonic acid salts and citric acid salts.

The compounds of formula (I) can also be solvated, e.g. hydrated. The solvation can be effected in the course of the manufacturing process or can take place e.g. as a consequence of hygroscopic properties of an initially anhydrous compound of formula (I) (hydration). The term pharmaceutically acceptable salts also includes physiologically acceptable solvates.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention. Preferred pharmaceutically acceptable esters of compounds of formula (I) are methyl and ethyl esters.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Preferred are the compounds of formula (I) and pharmaceutically acceptable salts or esters thereof.

Further preferred are the compounds of formula (I) and pharmaceutically acceptable salts thereof, particularly the compounds of formula (I).

Also further preferred are compounds of formula (I), wherein $R^1$ is selected from the group consisting of: dimethylpropyl, dimethylbutyl, cyclopropylalkyl, methyl-trifluoromethyl-1H-pyrazolyl, morpholinyl, phenyl, 2-chlorophenyl, 4-methylphenyl and 4-methoxyphenyl.

Moreover preferred are compounds of formula (I), wherein $R^1$ is selected from the group consisting of: dimethylpropyl, phenyl, 2-chlorophenyl and 4-methylphenyl.

Particularly preferred are compounds of formula (I), wherein $R^1$ is dimethylpropyl.

Also particularly preferred are compounds of formula (I), wherein $R^1$ is selected from the group consisting of: phenyl, 2-chlorophenyl and 4-methylphenyl.

Especially preferred are those compounds of formula (I), wherein $R^1$ is 4-methylphenyl.

Preferred are compounds of formula (I), wherein n is zero, 1, 2 or 3.

Particularly preferred are those wherein n is zero.

Further preferred are compounds of formula (I), wherein $R^2$ is hydrogen or hydroxyalkyl.

Particularly preferred are those wherein $R^2$ is hydrogen.

Also particularly preferred are those wherein $R^2$ is hydroxymethyl.

Another preferred embodiment of the present invention are compounds of formula (I), wherein $A^1$ is —S(O)$_2$—.

Also preferred are compounds of formula (I), wherein $A^2$ is a single bond or G.

Moreover preferred are those, wherein $A^2$ is a single bond.

Also preferred are compounds of formula (I), wherein $R^3$ is hydrogen.

Preferred are compounds of formula (I), wherein $R^4$ is selected from the group consisting of: hydrogen, methyl, hydroxymethyl and fluoro.

Particularly preferred are those, wherein $R^4$ is hydrogen.

Further preferred are compounds of formula (I), wherein $R^5$ is hydrogen or methyl.

Particularly preferred are those, wherein $R^5$ is hydrogen.

Another preferred embodiment of the present invention are compounds according to formula (I), wherein $R^6$ is selected from the group consisting of: 2,3-dihydro-benzofuranyl, alkylpyridin-3-yl, alkoxypyridazinyl, alkyl-trifluoromethyl-1H-pyrazolyl and substituted phenyl, wherein substituted phenyl is phenyl substituted in the 4-position with a substituent selected from the group consisting of: chlorine, isopropyl, hydroxyalkyl, isopropoxy, cycloalkylalkoxy, haloalkoxy, alkoxyhaloalkoxy and hydroxyhaloalkoxy.

Further preferred are compounds of formula (I), wherein $R^6$ is substituted phenyl, wherein substituted phenyl is phenyl substituted in the 4-position with a substituent selected from the group consisting of: chlorine, isopropyl, hydroxyalkyl, isopropoxy, cycloalkylalkoxy, haloalkoxy, alkoxyhaloalkoxy and hydroxyhaloalkoxy.

More preferred are compounds of formula (I), wherein $R^6$ is substituted phenyl, wherein substituted phenyl is phenyl substituted in the 4-position with a substituent selected from isopropoxy or haloalkoxy.

Particularly preferred are those, wherein $R^6$ is substituted phenyl wherein substituted phenyl is phenyl substituted in the 4-position with isopropoxy.

Also particularly preferred are those, wherein $R^6$ is substituted phenyl, wherein substituted phenyl is phenyl substituted in the 4-position with haloalkoxy.

Moreover preferred are compounds of formula (I), wherein $R^6$ is substituted phenyl, wherein substituted phenyl is phenyl substituted in the 4-position with trifluoromethoxy.

Examples of preferred compounds of formula (I) are selected from the group consisting of:

1-Benzenesulfonyl-piperidine-4-carboxylic acid (6-isopropyl-pyridin-3-yl)-amide;

1-Benzenesulfonyl-piperidine-4-carboxylic acid (6-methoxy-pyridazin-3-yl)-amide;

(rac)-1-(Toluene-4-sulfonyl)-piperidine-4-carboxylic acid ethyl-[4-(2,2,2-trifluoro-1-methyl-ethoxy)-phenyl]-amide;

(rac)-1-(Toluene-4-sulfonyl)-piperidine-4-carboxylic acid methyl-[4-(2,2,2-trifluoro-1-methyl-ethoxy)-phenyl]-amide;

(rac)-1-(Toluene-4-sulfonyl)-piperidine-4-carboxylic acid [6-(2,2,2-trifluoro-1-methyl-ethoxy)-pyridin-3-yl]-amide;

1-(Toluene-4-sulfonyl)-piperidine-4-carboxylic acid (4-isopropoxy-phenyl)-amide;

1-(2-Cyclopropyl-acetyl)-piperidine-4-carboxylic acid (4-isopropyl-phenyl)-amide;

1-(3-Cyclopropyl-propionyl)-piperidine-4-carboxylic acid (4-isopropyl-phenyl)-amide;

1-(3,3-Dimethyl-butyryl)-piperidine-4-carboxylic acid (4-isopropyl-phenyl)-amide;

(2S,4S)-1-(2-Chloro-benzenesulfonyl)-2-hydroxymethyl-piperidine-4-carboxylic acid methyl-(4-trifluoromethoxy-phenyl)-amide;

(2R,4R)-1-(2-Chloro-benzenesulfonyl)-2-hydroxymethyl-piperidine-4-carboxylic acid methyl-(4-trifluoromethoxy-phenyl)-amide;

1-Benzenesulfonyl-4-(3-methoxy-propyl)-piperidine-4-carboxylic acid (4-isopropoxy-phenyl)-amide;

1-(Toluene-4-sulfonyl)-piperidine-4-carboxylic acid (4-difluoromethoxy-phenyl)-amide;

1-(Toluene-4-sulfonyl)-piperidine-4-carboxylic acid [4-(2,2,2-trifluoro-ethoxy)-phenyl]-amide;

1-(Toluene-4-sulfonyl)-piperidine-4-carboxylic acid (2-fluoro-4-isopropoxy-phenyl)-amide;

1-(Toluene-4-sulfonyl)-piperidine-4-carboxylic acid methyl-(4-trifluoromethoxy-phenyl)-amide;

1-(Toluene-4-sulfonyl)-piperidine-4-carboxylic acid (2,3-dihydro-benzofuran-5-yl)-amide;

4-Fluoro-1-(toluene-4-sulfonyl)-piperidine-4-carboxylic acid (4-trifluoromethoxy-phenyl)-amide;

4-Fluoro-1-(toluene-4-sulfonyl)-piperidine-4-carboxylic acid (4-isopropoxy-phenyl)-amide;

1-(Toluene-4-sulfonyl)-piperidine-4-carboxylic acid (4-cyclopropylmethoxy-phenyl)-amide;

1-(3,3-Dimethyl-butyryl)-piperidine-4-carboxylic acid (4-trifluoromethoxy-phenyl)-amide;

1-(Toluene-4-sulfonyl)-piperidine-4-carboxylic acid [4-(2-hydroxy-ethyl)-phenyl]-amide;
(2S,4S)-2-Methoxymethyl-1-(toluene-4-sulfonyl)-piperidine-4-carboxylic acid (4-trifluoromethoxy-phenyl)-amide;
(2R,4R)-2-Methoxymethyl-1-(toluene-4-sulfonyl)-piperidine-4-carboxylic acid (4-trifluoromethoxy-phenyl)-amide;
(rac)-1-(2-Chloro-benzenesulfonyl)-4-hydroxymethyl-piperidine-4-carboxylic acid [4-(2,2,2-trifluoro-1-methyl-ethoxy)-phenyl]-amide;
(rac)-1-(Toluene-4-sulfonyl)-piperidine-4-carboxylic acid [4-(2,2,2-trifluoro-1-methyl-ethoxy)-phenyl]-amide;
1-Benzenesulfonyl-4-hydroxymethyl-piperidine-4-carboxylic acid (4-trifluoromethoxy-phenyl)-amide;
(rac)-1-benzenesulfonyl-4-hydroxymethyl-piperidine-4-carboxylic acid [4-(2,2,2-trifluoro-1-methyl-ethoxy)-phenyl]-amide;
1-(2-Chloro-benzenesulfonyl)-4-hydroxymethyl-piperidine-4-carboxylic acid (4-trifluoromethoxy-phenyl)-amide;
4-Fluoro-1-(4-methoxy-benzenesulfonyl)-piperidine-4-carboxylic acid (4-trifluoromethoxy-phenyl)-amide;
1-(2-Chloro-benzenesulfonyl)-4-fluoro-piperidine-4-carboxylic acid (4-trifluoromethoxy-phenyl)-amide;
4-Methyl-1-(toluene-4-sulfonyl)-piperidine-4-carboxylic acid (4-trifluoromethoxy-phenyl)-amide;
(rac)-4-Fluoro-1-(toluene-4-sulfonyl)-piperidine-4-carboxylic acid [4-(2,2,2-trifluoro-1-methyl-ethoxy)-phenyl]-amide;
1-(Toluene-4-sulfonyl)-piperidine-4-carboxylic acid [4-(2,2,2-trifluoro-1,1-dimethyl-ethoxy)-phenyl]-amide;
(rac)-1-(Toluene-4-sulfonyl)-piperidine-4-carboxylic acid [4-(1-cyclopropyl-ethoxy)-phenyl]-amide;
1-Benzenesulfonyl-piperidine-4-carboxylic acid (1-ethyl-5-trifluoromethyl-1H-pyrazol-3-yl)-amide;
(2S,4S)-1-(2-Chloro-benzenesulfonyl)-2-hydroxymethyl-piperidine-4-carboxylic acid (4-trifluoromethoxy-phenyl)-amide;
(2R,4R)-1-(2-Chloro-benzenesulfonyl)-2-hydroxymethyl-piperidine-4-carboxylic acid (4-trifluoromethoxy-phenyl)-amide;
1-(Morpholine-4-sulfonyl)-piperidine-4-carboxylic acid (4-trifluoromethoxy-phenyl)-amide;
1-(2-Chloro-benzenesulfonyl)-piperidine-4-carboxylic acid (4-trifluoromethoxy-phenyl)-amide;
1-(2-Chloro-benzenesulfonyl)-piperidine-4-carboxylic acid (4-isopropoxy-phenyl)-amide;
(rac)-1-(2-Chloro-benzenesulfonyl)-piperidine-4-carboxylic acid [4-(2,2,2-trifluoro-1-methyl-ethoxy)-phenyl]-amide;
4-Fluoro-1-(toluene-4-sulfonyl)-piperidine-4-carboxylic acid (4-isopropyl-phenyl)-amide;
(2S,4S)-2-Hydroxymethyl-1-(toluene-4-sulfonyl)-piperidine-4-carboxylic acid (4-trifluoromethoxy-phenyl)-amide;
(2R,4R)-2-Hydroxymethyl-1-(toluene-4-sulfonyl)-piperidine-4-carboxylic acid (4-trifluoromethoxy-phenyl)-amide;
(rac)-4-Methyl-1-(toluene-4-sulfonyl)-piperidine-4-carboxylic acid [4-(2,2,2-trifluoro-1-methyl-ethoxy)-phenyl]-amide;
(rac)-1-(2-Chloro-benzoyl)-piperidine-4-carboxylic acid [4-(2,2,2-trifluoro-1-methyl-ethoxy)-phenyl]-amide;
1-(Toluene-4-sulfonyl)-piperidine-4-carboxylic acid [4-(2,2,2-trifluoro-1-hydroxymethyl-ethoxy)-phenyl]-amide;
1-Benzenesulfonyl-piperidine-4-carboxylic acid (4-isopropoxy-phenyl)-amide;
1-(4-Methoxy-benzenesulfonyl)-piperidine-4-carboxylic acid (4-isopropoxy-phenyl)-amide;
(rac)-1-Benzenesulfonyl-4-methyl-piperidine-4-carboxylic acid [4-(2,2,2-trifluoro-1,1-dimethyl-ethoxy)-phenyl]-amide;
4-Hydroxymethyl-1-(toluene-4-sulfonyl)-piperidine-4-carboxylic acid (4-trifluoromethoxy-phenyl)-amide;
(rac)-1-(Toluene-4-sulfonyl)-piperidine-4-carboxylic acid [4-(3,3,3-trifluoro-2-hydroxy-propoxy)-phenyl]-amide;
(rac)-1-(Toluene-4-sulfonyl)-piperidine-4-carboxylic acid [4-(3,3,3-trifluoro-2-methoxy-propoxy)-phenyl]-amide;
(rac)-1-(Toluene-4-sulfonyl)-piperidine-4-carboxylic acid [4-(2,2,2-trifluoro-1-methoxymethyl-ethoxy)-phenyl]-amide;
4-Hydroxymethyl-1-(toluene-4-sulfonyl)-piperidine-4-carboxylic acid [4-(2,2,2-trifluoro-1-methyl-ethoxy)-phenyl]-amide;
1-(4,4-Dimethyl-pentanoyl)-piperidine-4-carboxylic acid (4-trifluoromethoxy-phenyl)-amide;
1-Benzenesulfonyl-4-methyl-piperidine-4-carboxylic acid (4-trifluoromethoxy-phenyl)-amide;
1-(2-Chloro-benzenesulfonyl)-4-methyl-piperidine-4-carboxylic acid (4-trifluoromethoxy-phenyl)-amide;
1-(Toluene-4-sulfonyl)-piperidine-4-carboxylic acid [4-((R)-3-methoxy-1-trifluoromethyl-propoxy)-phenyl]-amide;
1-(Toluene-4-sulfonyl)-piperidine-4-carboxylic acid [4-((R)-3-hydroxy-1-trifluoromethyl-propoxy)-phenyl]-amide;
1-(2-Chloro-benzenesulfonyl)-piperidine-4-carboxylic acid [1-(4-chloro-phenyl)-cyclopropylmethyl]-amide;
1-Benzenesulfonyl-piperidine-4-carboxylic acid [1-(4-chloro-phenyl)-cyclopropylmethyl]-amide;
4-Fluoro-1-(1-methyl-3-trifluoromethyl-1H-pyrazole-4-sulfonyl)-piperidine-4-carboxylic acid (4-trifluoromethoxy-phenyl)-amide; and
1-(Toluene-4-sulfonyl)-piperidine-4-carboxylic acid [1-(4-chloro-phenyl)-cyclopropylmethyl]-amide.

Further particularly preferred examples of compounds of formula (I) are selected from the group consisting of:
1-(Toluene-4-sulfonyl)-piperidine-4-carboxylic acid (4-isopropoxy-phenyl)-amide;
(2S,4S)-1-(2-Chloro-benzenesulfonyl)-2-hydroxymethyl-piperidine-4-carboxylic acid methyl-(4-trifluoromethoxy-phenyl)-amide;
(2R,4R)-1-(2-Chloro-benzenesulfonyl)-2-hydroxymethyl-piperidine-4-carboxylic acid methyl-(4-trifluoromethoxy-phenyl)-amide;
1-(Toluene-4-sulfonyl)-piperidine-4-carboxylic acid methyl-(4-trifluoromethoxy-phenyl)-amide;
1-(3,3-Dimethyl-butyryl)-piperidine-4-carboxylic acid (4-trifluoromethoxy-phenyl)-amide;
1-Benzenesulfonyl-4-hydroxymethyl-piperidine-4-carboxylic acid (4-trifluoromethoxy-phenyl)-amide;

1-(2-Chloro-benzenesulfonyl)-4-fluoro-piperidine-4-carboxylic acid (4-trifluoromethoxy-phenyl)-amide;
(rac)-1-(2-Chloro-benzenesulfonyl)-piperidine-4-carboxylic acid [4-(2,2,2-trifluoro-1-methyl-ethoxy)-phenyl]-amide;
(2S,4S)-2-Hydroxymethyl-1-(toluene-4-sulfonyl)-piperidine-4-carboxylic acid (4-trifluoromethoxy-phenyl)-amide;
(2R,4R)-2-Hydroxymethyl-1-(toluene-4-sulfonyl)-piperidine-4-carboxylic acid (4-trifluoromethoxy-phenyl)-amide; and
1-Benzenesulfonyl-4-methyl-piperidine-4-carboxylic acid (4-trifluoromethoxy-phenyl)-amide.

Processes for the manufacture of compounds of formula (I) are an object of the invention.

The preparation of compounds of formula (I) of the present invention may be carried out in sequential or convergent synthetic routes. Syntheses of the invention are shown in the following schemes. The skills required for carrying out the reaction and purification of the resulting products are known to those persons skilled in the art. In case a mixture of enantiomers or diastereoisomers is produced during a reaction, these enantiomers can be separated by methods described herein or known to the man skilled in the art such as e.g. chiral chromatography. The substituents and indices used in the following description of the processes have the significance given herein.

Compounds of formula (I) are readily accessible as outlined in scheme 1 on application of the aluminium-mediated conversion of esters to amides, the Weinreb reaction. Thus, by heating compounds of formula (II) with an amine of general formula (IV) and dimethylaluminium chloride in a solvent such as toluene at reflux temperature. Alternatively, dioxane can be used as solvent and trimethylaluminium as organometallic reagent (scheme 1).

Also, the synthesis of compounds of general formula (I) can be achieved in a stepwise process according to scheme 1, wherein compounds of formula (II) are first hydrolyzed under standard conditions on treatment with aqueous NaOH in a solvent such as methanol or ethanol at RT or reflux temperatures to give the corresponding acids (III). These can then be condensed with the amines of formula (IV) using standard condensation reagents such as EDC, BOP or CDMT in the presence of a base such as triethylamine, N-methyl-morpholine or Hunig's base in solvents such as acetonitrile, THF or DMF, at RT or elevated temperatures to give compounds of formula (I). Alternatively, the acids of formula (III) can first be converted to the corresponding acid chloride with, e.g., with oxalyl chloride in methylene chloride and triethylamine as a base or with thionyl chloride and then reacted with the amines of formula (IV) to give the amides of formula (I).

Scheme 1

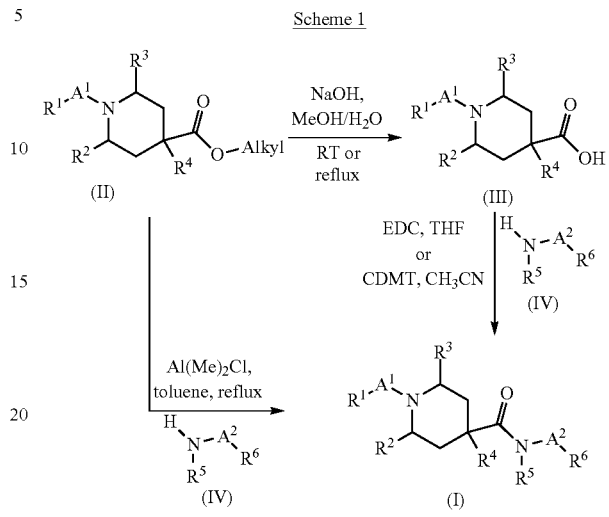

Alkyl is e.g. methyl or ethyl

A further alternative process to synthesize compounds of formula (I) is outlined in scheme 2.

Thus, starting form suitably protected compounds of formula (IIa), wherein PG is a protecting group, e.g. benzyl, Boc or Cbz which is compatible with the reaction conditions applied, these are subsequently converted directly to compounds formula (Ia) on reaction with the amines of formula (IV) and dimethylaluminium chloride in toluene at reflux temperature or stepwise via the acids of formula (IIIa) and subsequent coupling with the amines of formula (IV) to give the compounds of formula (Ia) The protecting group can then be removed by standard conditions e.g. Boc cleavage with trifluororoacetic acid in methylene chloride as a solvent at RT, to give the compounds of formula (Ib). Subsequent condensation with a compound of formula (V) under standard conditions, in THF, methylene chloride, DMF or the like in the presence of a base such as DMAP, or triethylamine, or in pyridine gives then rise to compounds of formula (I). Carboxylic acids of formula (VI) can be used in the reaction together with an appropriate condensation reagent such as the EDC, BOP and the like in solvents such as THF, acetonitrile and a base e.g. Hunigs's base or trietylamine or DMAP to give the compounds of general formula (I), wherein $A^1$ is carbonyl.

Scheme 2

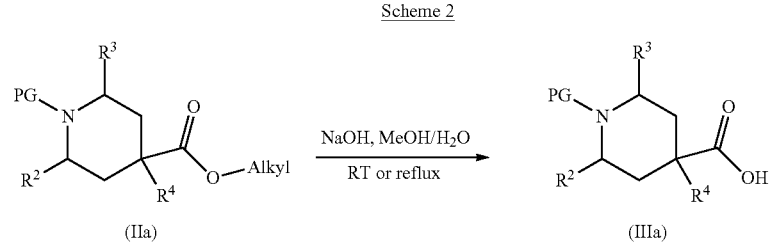

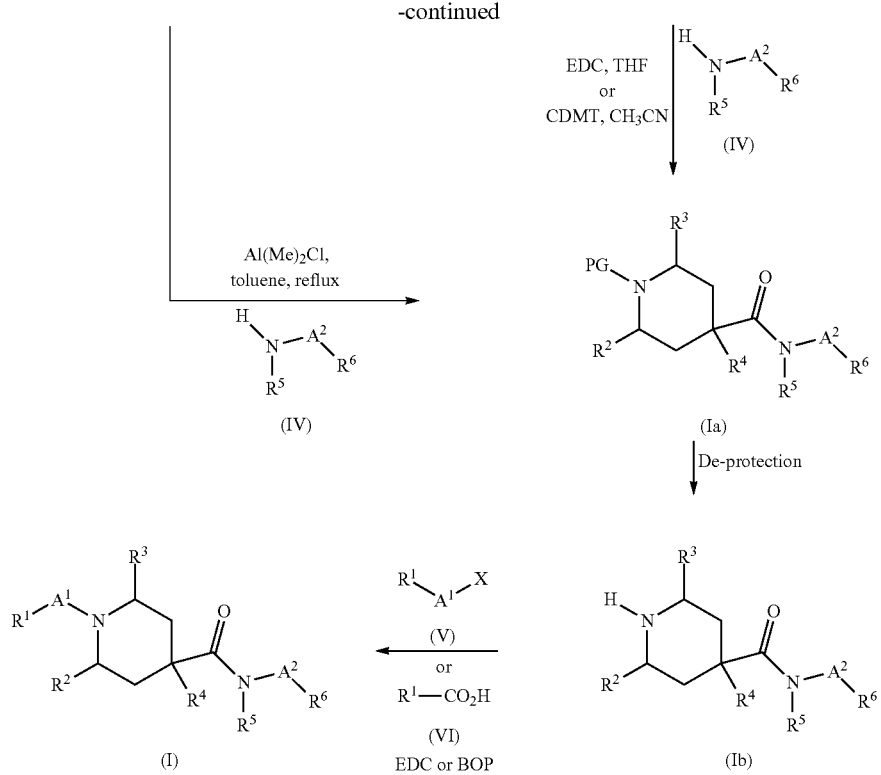

Alkyl is e.g. methyl or ethyl
PG is e.g. benzyl, Boc or Cbz
X is halogen, preferably Cl The starting materials that are used in schemes 1 to 2 can be prepared from commercial compounds or compounds described in the literature applying general reaction procedures known in the art and outlined in scheme 3.

Thus, compounds of formula (II) wherein $R^4$ is alkyl or alkoxyalkyl are prepared from compounds of formula (VII), wherein PG is a protecting group, e.g. benzyl, Boc or Cbz which is compatible with the reaction conditions applied, which are either commercial or known in the literature. Compounds of formula (VII) can then be treated with a base such as LDA at low temperature in a solvent such as THF followed by reaction with compounds of formula (VIII), wherein $R^4$ is alkyl or alkoxyalkyl and X is halogen, such as chlorine or bromine, to give compounds of formula (IIa). These can then be de-protected and reacted with compounds of formula (V) or (VI) as already outlined above to give the compounds of formula (II).

Scheme 3

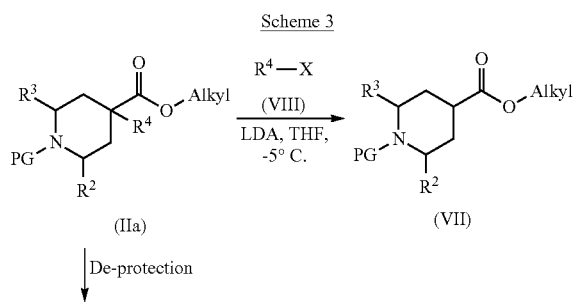

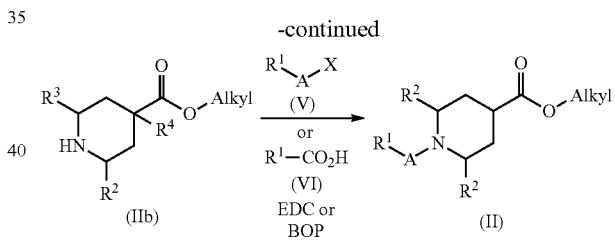

X is halogen, preferably Cl or Br
Alkyl is e.g. methyl or ethyl
Protecting group is e.g. benzyl, Boc or Cbz Compounds of formula (Ia) wherein $R^4$ is hydroxylalkyl, can be prepared as described in scheme 4 from the corresponding compounds of formula (IX) wherein $R^7$ is benzyloxyalkyl by applying the Weinreb reaction as described above with $Al(Me)_2Cl$ as reagent that results in simultaneous amide formation and benzyl group cleavage in $R^7$. Alternatively the benzyl group in $R^7$ can be taken off separately as known in the art.

Scheme 4

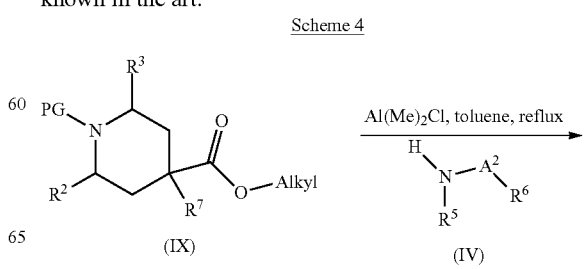

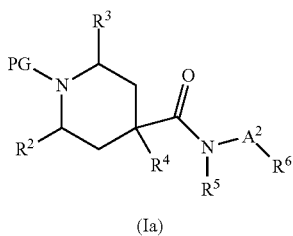

(Ia)

Alkyl is e.g. methyl or ethyl

Compounds of formula (IX), wherein R⁷ is benzyloxyalkyl can be prepared as described in scheme 5 by analogy to compounds of formula (IIa).

Scheme 5

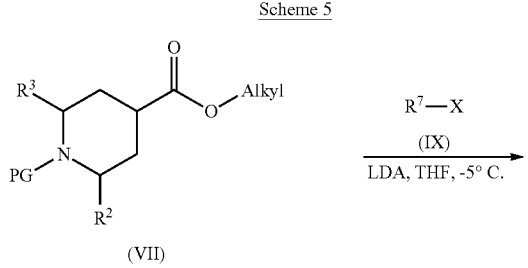

X is halogen, preferably Cl or Br
Alkyl is e.g. methyl or ethyl
Protecting group is e.g. benzyl, Boc or Cbz Preferred is a process to prepare a compound of formula (I) as defined before

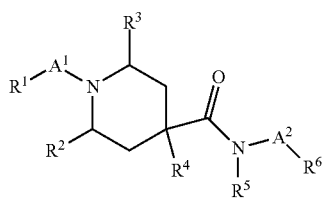

(I)

comprising a a) reaction of a compound of formula (II) in the presence of a compound of formula (IV);

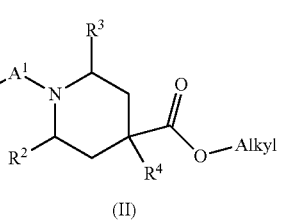 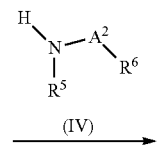

(II)         (IV)

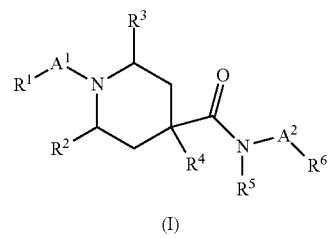

(I)

preferably in the presence of an organoaluminium compound of formula Al(Alkyl)$_3$ or Al(Alkyl)$_2$X, particularly trimethylaluminium or dimethylaluminium chloride, in a solvent, particularly toluene or dioxane, and at a temperature between RT and reflux of the solvent, particularly at reflux of the solvent, wherein $R^1$, $R^2$, $R^3$, $R^4$, $R^5$, $R^6$, $A^1$ and $A^2$ are as defined before;

b) reaction of a compound of formula (III) in the presence of a compound of formula (IV);

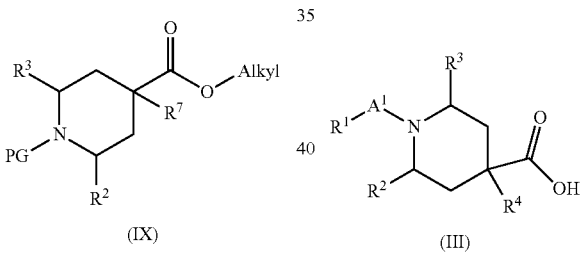 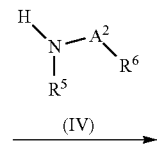

(III)        (IV)

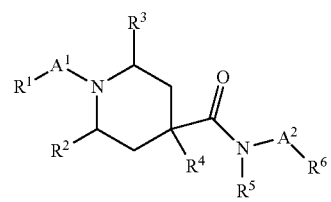

(I)

preferably in the presence of a condensation reagent, particularly EDC, BOP or CDMT, in the presence of a base, particularly, triethylamine, N-methyl-morpholine or Hünig's base, in a solvent, particularly acetonitrile, THF or DMF, and at a temperature between −10° C. and reflux of the solvent, particularly at RT, wherein $R^1$, $R^2$, $R^3$, $R^4$, $R^5$, $R^6$, $A^1$ and $A^2$ are as defined before;

c) reaction of a compound of formula (X) in the presence of a compound of formula (IV);

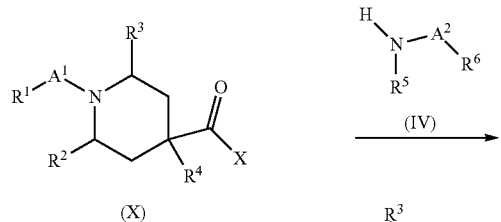

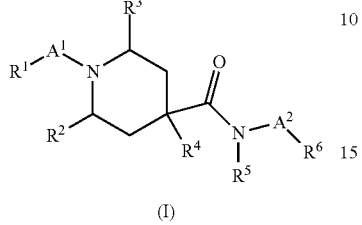

preferably in the presence of a base, particularly pyridine, triethylamine or DMAP, in a solvent, particularly pyridine, THF or methylene chloride, and at a temperature between −20° C. and reflux of the solvent, particularly at RT, wherein $R^1, R^2, R^3, R^4, R^5, R^6, A^1$ and $A^2$ are as defined before and X is halogen, particularly chlorine;

d) reaction of a compound of formula (Ib) in the presence of a compound of formula (V);

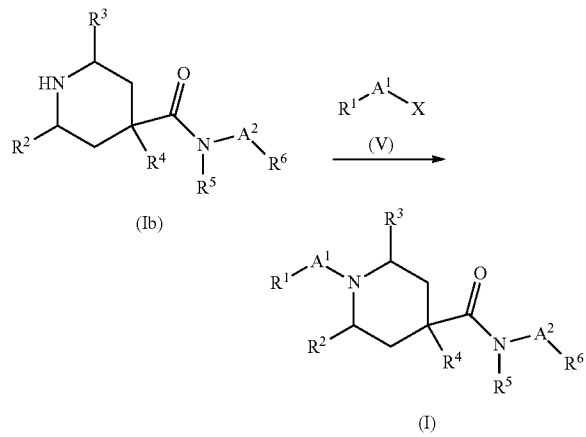

preferably in the presence of a base, particularly pyridine, triethylamine or DMAP, in a solvent, particularly pyridine, THF or methylene chloride, and at a temperature between −20° C. and reflux of the solvent, particularly at RT, wherein $R^1, R^2, R^3, R^4, R^5, R^6, A^1$ and $A^2$ are as defined before and X is halogen, particularly chlorine;

or e) reaction of a compound of formula (Ib) in the presence of a compound of formula (VI);

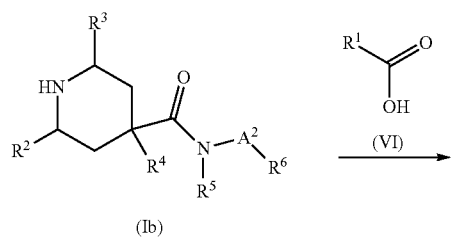

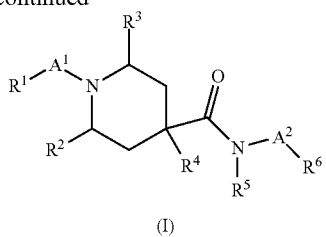

preferably in the presence of a condensation reagent, particularly EDC, BOP or CDMT, in the presence of a base, particularly, triethylamine, N-methyl-morpholine or Hünig's base, in a solvent, particularly acetonitrile, THF or DMF, and at a temperature between −10° C. and reflux of the solvent, particularly at RT, wherein $R^1, R^2, R^3, R^4, R^5, R^6$, and $A^2$ are as defined before and $A^1$ is carbonyl.

Preferred intermediates are selected from the group consisting of:

Benzenesulfonyl-4-(3-methoxy-propyl)-piperidine-4-carboxylic acid ethyl ester;
4-Fluoro-1-(toluene-4-sulfonyl)-piperidine-4-carboxylic acid ethyl ester;
4-Fluoro-1-(toluene-4-sulfonyl)-piperidine-4-carboxylic acid;
4-Benzyloxymethyl-piperidine-1,4-dicarboxylic acid 1-tert-butyl ester 4-ethyl ester;
4-Benzyloxymethyl-piperidine-4-carboxylic acid ethyl ester;
4-Benzyloxymethyl-1-(benzenesulfonyl)-piperidine-4-carboxylic acid ethyl ester;
4-Fluoro-4-(4-trifluoromethoxy-phenylcarbamoyl)-piperidine-1-carboxylic acid tert-butyl ester;
4-Fluoro-piperidine-4-carboxylic acid (4-trifluoromethoxy-phenyl)-amide;
4-Methyl-4-(4-trifluoromethoxy-phenylcarbamoyl)-piperidine-1-carboxylic acid tert-butyl ester;
(2S,4S)-1-(2-Chloro-benzenesulfonyl)-piperidine-2,4-dicarboxylic acid 4-methyl ester;
(2R,4R)-1-(2-Chloro-benzenesulfonyl)-piperidine-2,4-dicarboxylic acid 4-methyl ester;
(2S,4S)-1-(2-Chloro-benzenesulfonyl)-4-(4-trifluoromethoxy-phenylcarbamoyl)-piperidine-2-carboxylic acid;
(2R,4R)-1-(2-Chloro-benzenesulfonyl)-4-(4-trifluoromethoxy-phenylcarbamoyl)-piperidine-2-carboxylic acid;
1-(Morpholine-4-sulfonyl)-piperidine-4-carboxylic acid ethyl ester;
1-(Morpholine-4-sulfonyl)-piperidine-4-carboxylic acid;
(2S,4S)-1-(Toluene-4-sulfonyl)-piperidine-2,4-dicarboxylic acid 4-methyl ester;
(2R,4R)-1-(Toluene-4-sulfonyl)-piperidine-2,4-dicarboxylic acid 4-methyl ester;
(2S,4S)-1-(Toluene-4-sulfonyl)-4-(4-trifluoromethoxy-phenylcarbamoyl)-piperidine-2-carboxylic acid;
(2R,4R)-1-(Toluene-4-sulfonyl)-4-(4-trifluoromethoxy-phenylcarbamoyl)-piperidine-2-carboxylic acid;
(rac)-4-Methyl-4-[4-(2,2,2-trifluoro-1-methyl-ethoxy)-phenylcarbamoyl]-piperidine-1-carboxylic acid tert-butyl ester;
(rac)-4-Methyl-piperidine-4-carboxylic acid [4-(2,2,2-trifluoro-1-methyl-ethoxy)-phenyl]-amide;
4-Benzyloxymethyl-1-(toluene-4-sulfonyl)-piperidine-4-carboxylic acid ethyl ester;

4-Fluoro-1-(1-methyl-3-trifluoromethyl-1H-pyrazole-4-sulfonyl)-piperidine-4-carboxylic acid ethyl ester; and
4-Fluoro-1-(1-methyl-3-trifluoromethyl-1H-pyrazole-4-sulfonyl)-piperidine-4-carboxylic acid.

A further object of the invention are compounds according to formula (I) as described above for use as therapeutically active substance.

A further object of the invention are compounds selected from the group consisting of: 1-(toluene-4-sulfonyl)-piperidine-4-carboxylic acid (4-trifluoromethoxy-phenyl)-amide, 1-(toluene-4-sulfonyl)-piperidine-4-carboxylic acid [2-(4-difluoromethoxy-phenyl)-ethyl]-amide, 1-benzenesulfonyl-piperidine-4-carboxylic acid (4-isopropyl-phenyl)-amide, 1-(toluene-4-sulfonyl)-piperidine-4-carboxylic acid (4-isopropyl-phenyl)-amide, 1-(4-methoxy-benzenesulfonyl)-piperidine-4-carboxylic acid (4-trifluoromethoxy-phenyl)-amide, 1-benzenesulfonyl-piperidine-4-carboxylic acid (4-trifluoromethoxy-phenyl)-amide, 1-(4-methoxy-benzenesulfonyl)-piperidine-4-carboxylic acid (4-difluoromethoxy-phenyl)-amide, 1-(4-methoxy-benzenesulfonyl)-piperidine-4-carboxylic acid (4-isopropyl-phenyl)-amide, 1-(4-methoxy-benzenesulfonyl)-piperidine-4-carboxylic acid (4-chloro-2-fluoro-phenyl)-amide, 1-benzoyl-piperidine-4-carboxylic acid (4-isopropyl-phenyl)-amide, 1-(2-chloro-benzoyl)-piperidine-4-carboxylic acid (4-isopropyl-phenyl)-amide, 1-benzenesulfonyl-piperidine-4-carboxylic acid (1-phenyl-cyclopropylmethyl)-amide and 1-(toluene-4-sulfonyl)-piperidine-4-carboxylic acid (1-phenyl-cyclopentylmethyl)-amide.

Likewise an object of the present invention are pharmaceutical compositions comprising a therapeutically inert carrier and a compound according to formula (I) as described above or a compound selected from 1-(toluene-4-sulfonyl)-piperidine-4-carboxylic acid (4-trifluoromethoxy-phenyl)-amide, 1-(toluene-4-sulfonyl)-piperidine-4-carboxylic acid [2-(4-difluoromethoxy-phenyl)-ethyl]-amide, 1-benzenesulfonyl-piperidine-4-carboxylic acid (4-isopropyl-phenyl)-amide, 1-(toluene-4-sulfonyl)-piperidine-4-carboxylic acid (4-isopropyl-phenyl)-amide, 1-(4-methoxy-benzenesulfonyl)-piperidine-4-carboxylic acid (4-trifluoromethoxy-phenyl)-amide, 1-benzenesulfonyl-piperidine-4-carboxylic acid (4-trifluoromethoxy-phenyl)-amide, 1-(4-methoxy-benzenesulfonyl)-piperidine-4-carboxylic acid (4-difluoromethoxy-phenyl)-amide, 1-(4-methoxy-benzenesulfonyl)-piperidine-4-carboxylic acid (4-isopropyl-phenyl)-amide, 1-(4-methoxy-benzenesulfonyl)-piperidine-4-carboxylic acid (4-chloro-2-fluoro-phenyl)-amide, 1-benzoyl-piperidine-4-carboxylic acid (4-isopropyl-phenyl)-amide, 1-(2-chloro-benzoyl)-piperidine-4-carboxylic acid (4-isopropyl-phenyl)-amide, 1-benzenesulfonyl-piperidine-4-carboxylic acid (1-phenyl-cyclopropylmethyl)-amide and 1-(toluene-4-sulfonyl)-piperidine-4-carboxylic acid (1-phenyl-cyclopentylmethyl)-amide.

Preferred are pharmaceutical compositions comprising a therapeutically inert carrier and a compound according to formula (I) as described above.

Also an object of the present invention are compounds according to formula (I) as described above, 1-(toluene-4-sulfonyl)-piperidine-4-carboxylic acid (4-trifluoromethoxy-phenyl)-amide, 1-(toluene-4-sulfonyl)-piperidine-4-carboxylic acid [2-(4-difluoromethoxy-phenyl)-ethyl]-amide, 1-benzenesulfonyl-piperidine-4-carboxylic acid (4-isopropyl-phenyl)-amide, 1-(toluene-4-sulfonyl)-piperidine-4-carboxylic acid (4-isopropyl-phenyl)-amide, 1-(4-methoxy-benzenesulfonyl)-piperidine-4-carboxylic acid (4-trifluoromethoxy-phenyl)-amide, 1-benzenesulfonyl-piperidine-4-carboxylic acid (4-trifluoromethoxy-phenyl)-amide, 1-(4-methoxy-benzenesulfonyl)-piperidine-4-carboxylic acid (4-difluoromethoxy-phenyl)-amide, 1-(4-methoxy-benzenesulfonyl)-piperidine-4-carboxylic acid (4-isopropyl-phenyl)-amide, 1-(4-methoxy-benzenesulfonyl)-piperidine-4-carboxylic acid (4-chloro-2-fluoro-phenyl)-amide, 1-benzoyl-piperidine-4-carboxylic acid (4-isopropyl-phenyl)-amide, 1-(2-chloro-benzoyl)-piperidine-4-carboxylic acid (4-isopropyl-phenyl)-amide, 1-benzenesulfonyl-piperidine-4-carboxylic acid (1-phenyl-cyclopropylmethyl)-amide or 1-(toluene-4-sulfonyl)-piperidine-4-carboxylic acid (1-phenyl-cyclopentylmethyl)-amide for the preparation of a medicament for the treatment or prophylaxis of illnesses which are caused by disorders associated e.g. with the enzyme hormone-sensitive lipase.

Further preferred are compounds according to formula (I) as described above, 1-(toluene-4-sulfonyl)-piperidine-4-carboxylic acid (4-trifluoromethoxy-phenyl)-amide, 1-(toluene-4-sulfonyl)-piperidine-4-carboxylic acid [2-(4-difluoromethoxy-phenyl)-ethyl]-amide, 1-benzenesulfonyl-piperidine-4-carboxylic acid (4-isopropyl-phenyl)-amide, 1-(toluene-4-sulfonyl)-piperidine-4-carboxylic acid (4-isopropyl-phenyl)-amide, 1-(4-methoxy-benzenesulfonyl)-piperidine-4-carboxylic acid (4-trifluoromethoxy-phenyl)-amide, 1-benzenesulfonyl-piperidine-4-carboxylic acid (4-trifluoromethoxy-phenyl)-amide, 1-(4-methoxy-benzenesulfonyl)-piperidine-4-carboxylic acid (4-difluoromethoxy-phenyl)-amide, 1-(4-methoxy-benzenesulfonyl)-piperidine-4-carboxylic acid (4-isopropyl-phenyl)-amide, 1-(4-methoxy-benzenesulfonyl)-piperidine-4-carboxylic acid (4-chloro-2-fluoro-phenyl)-amide, 1-benzoyl-piperidine-4-carboxylic acid (4-isopropyl-phenyl)-amide, 1-(2-chloro-benzoyl)-piperidine-4-carboxylic acid (4-isopropyl-phenyl)-amide, 1-benzenesulfonyl-piperidine-4-carboxylic acid (1-phenyl-cyclopropylmethyl)-amide or 1-(toluene-4-sulfonyl)-piperidine-4-carboxylic acid (1-phenyl-cyclopentylmethyl)-amide for the preparation of a medicament for the treatment or prophylaxis of diabetes, metabolic syndrome, dyslipidemia, atherosclerosis or obesity.

Also further preferred are compounds according to formula (I) as described above, 1-(toluene-4-sulfonyl)-piperidine-4-carboxylic acid (4-trifluoromethoxy-phenyl)-amide, 1-(toluene-4-sulfonyl)-piperidine-4-carboxylic acid [2-(4-difluoromethoxy-phenyl)-ethyl]-amide, 1-benzenesulfonyl-piperidine-4-carboxylic acid (4-isopropyl-phenyl)-amide, 1-(toluene-4-sulfonyl)-piperidine-4-carboxylic acid (4-isopropyl-phenyl)-amide, 1-(4-methoxy-benzenesulfonyl)-piperidine-4-carboxylic acid (4-trifluoromethoxy-phenyl)-amide, 1-benzenesulfonyl-piperidine-4-carboxylic acid (4-trifluoromethoxy-phenyl)-amide, 1-(4-methoxy-benzenesulfonyl)-piperidine-4-carboxylic acid (4-difluoromethoxy-phenyl)-amide, 1-(4-methoxy-benzenesulfonyl)-piperidine-4-carboxylic acid (4-isopropyl-phenyl)-amide, 1-(4-methoxy-benzenesulfonyl)-piperidine-4-carboxylic acid (4-chloro-2-fluoro-phenyl)-amide, 1-benzoyl-piperidine-4-carboxylic acid (4-isopropyl-phenyl)-amide, 1-(2-chloro-benzoyl)-piperidine-4-carboxylic acid (4-isopropyl-phenyl)-amide, 1-benzenesulfonyl-piperidine-4-carboxylic acid (1-phenyl-cyclopropylmethyl)-amide or 1-(toluene-4-sulfonyl)-piperidine-4-carboxylic acid (1-phenyl-cyclopentylmethyl)-amide for the preparation of a medicament for the treatment or prophylaxis of cardiovascular diseases, myocardial dysfunction or inflammation.

Particularly preferred are compounds according to formula (I) as described above for the preparation of medicaments for the treatment or prophylaxis of diabetes.

Moreover preferred are compounds according to formula (I) as described above for the preparation of medicaments for the treatment or prophylaxis of diabetes Type II.

A further preferred embodiment of the present invention is the use of a compound according to formula (I) as described above or of a compound selected from 1-(toluene-4-sulfonyl)-piperidine-4-carboxylic acid (4-trifluoromethoxy-phenyl)-amide, 1-(toluene-4-sulfonyl)-piperidine-4-carboxylic acid [2-(4-difluoromethoxy-phenyl)-ethyl]-amide, 1-benzenesulfonyl-piperidine-4-carboxylic acid (4-isopropyl-phenyl)-amide, 1-(toluene-4-sulfonyl)-piperidine-4-carboxylic acid (4-isopropyl-phenyl)-amide, 1-(4-methoxy-benzenesulfonyl)-piperidine-4-carboxylic acid (4-trifluoromethoxy-phenyl)-amide, 1-benzenesulfonyl-piperidine-4-carboxylic acid (4-trifluoromethoxy-phenyl)-amide, 1-(4-methoxy-benzenesulfonyl)-piperidine-4-carboxylic acid (4-difluoromethoxy-phenyl)-amide, 1-(4-methoxy-benzenesulfonyl)-piperidine-4-carboxylic acid (4-isopropyl-phenyl)-amide, 1-(4-methoxy-benzenesulfonyl)-piperidine-4-carboxylic acid (4-chloro-2-fluoro-phenyl)-amide, 1-benzoyl-piperidine-4-carboxylic acid (4-isopropyl-phenyl)-amide, 1-(2-chloro-benzoyl)-piperidine-4-carboxylic acid (4-isopropyl-phenyl)-amide, 1-benzenesulfonyl-piperidine-4-carboxylic acid (1-phenyl-cyclopropylmethyl)-amide and 1-(toluene-4-sulfonyl)-piperidine-4-carboxylic acid (1-phenyl-cyclopentylmethyl)-amide for the preparation of a medicament for the treatment or prophylaxis of diabetes, metabolic syndrome, dyslipidemia, atherosclerosis or obesity.

Also a further preferred embodiment of the present invention is the use of a compound according to formula (I) as described above or of a compound selected from 1-(toluene-4-sulfonyl)-piperidine-4-carboxylic acid (4-trifluoromethoxy-phenyl)-amide, 1-(toluene-4-sulfonyl)-piperidine-4-carboxylic acid [2-(4-difluoromethoxy-phenyl)-ethyl]-amide, 1-benzenesulfonyl-piperidine-4-carboxylic acid (4-isopropyl-phenyl)-amide, 1-(toluene-4-sulfonyl)-piperidine-4-carboxylic acid (4-isopropyl-phenyl)-amide, 1-(4-methoxy-benzenesulfonyl)-piperidine-4-carboxylic acid (4-trifluoromethoxy-phenyl)-amide, 1-benzenesulfonyl-piperidine-4-carboxylic acid (4-trifluoromethoxy-phenyl)-amide, 1-(4-methoxy-benzenesulfonyl)-piperidine-4-carboxylic acid (4-difluoromethoxy-phenyl)-amide, 1-(4-methoxy-benzenesulfonyl)-piperidine-4-carboxylic acid (4-isopropyl-phenyl)-amide, 1-(4-methoxy-benzenesulfonyl)-piperidine-4-carboxylic acid (4-chloro-2-fluoro-phenyl)-amide, 1-benzoyl-piperidine-4-carboxylic acid (4-isopropyl-phenyl)-amide, 1-(2-chloro-benzoyl)-piperidine-4-carboxylic acid (4-isopropyl-phenyl)-amide, 1-benzenesulfonyl-piperidine-4-carboxylic acid (1-phenyl-cyclopropylmethyl)-amide and 1-(toluene-4-sulfonyl)-piperidine-4-carboxylic acid (1-phenyl-cyclopentylmethyl)-amide for the preparation of a medicament for the treatment or prophylaxis of cardiovascular diseases, myocardial dysfunction or inflammation.

Particularly preferred is the use of a compound according to formula (I) as described above for the preparation of medicaments for the treatment or prophylaxis of diabetes.

Moreover preferred is the use of a compound according to formula (I) as described above for the preparation of medicaments for the treatment or prophylaxis of diabetes Type II.

A further object of the present invention comprises a compound according to formula (I) as described above or a compound selected from 1-(toluene-4-sulfonyl)-piperidine-4-carboxylic acid (4-trifluoromethoxy-phenyl)-amide, 1-(toluene-4-sulfonyl)-piperidine-4-carboxylic acid [2-(4-difluoromethoxy-phenyl)-ethyl]-amide, 1-benzenesulfonyl-piperidine-4-carboxylic acid (4-isopropyl-phenyl)-amide, 1-(toluene-4-sulfonyl)-piperidine-4-carboxylic acid (4-isopropyl-phenyl)-amide, 1-(4-methoxy-benzenesulfonyl)-piperidine-4-carboxylic acid (4-trifluoromethoxy-phenyl)-amide, 1-benzenesulfonyl-piperidine-4-carboxylic acid (4-trifluoromethoxy-phenyl)-amide, 1-(4-methoxy-benzenesulfonyl)-piperidine-4-carboxylic acid (4-difluoromethoxy-phenyl)-amide, 1-(4-methoxy-benzenesulfonyl)-piperidine-4-carboxylic acid (4-isopropyl-phenyl)-amide, 1-(4-methoxy-benzenesulfonyl)-piperidine-4-carboxylic acid (4-chloro-2-fluoro-phenyl)-amide, 1-benzoyl-piperidine-4-carboxylic acid (4-isopropyl-phenyl)-amide, 1-(2-chloro-benzoyl)-piperidine-4-carboxylic acid (4-isopropyl-phenyl)-amide, 1-benzenesulfonyl-piperidine-4-carboxylic acid (1-phenyl-cyclopropylmethyl)-amide and 1-(toluene-4-sulfonyl)-piperidine-4-carboxylic acid (1-phenyl-cyclopentylmethyl)-amide, when manufactured according to any one of the described processes.

Preferred is a compound according to formula (I) as described above when manufactured according to any one of the described processes.

Also an object of the invention is a method for the treatment or prophylaxis of diabetes, metabolic syndrome, dyslipidemia, atherosclerosis or obesity, which method comprises administering an effective amount of a compound according to formula (I) as described above or of a compound selected from 1-(toluene-4-sulfonyl)-piperidine-4-carboxylic acid (4-trifluoromethoxy-phenyl)-amide, 1-(toluene-4-sulfonyl)-piperidine-4-carboxylic acid [2-(4-difluoromethoxy-phenyl)-ethyl]-amide, 1-benzenesulfonyl-piperidine-4-carboxylic acid (4-isopropyl-phenyl)-amide, 1-(toluene-4-sulfonyl)-piperidine-4-carboxylic acid (4-isopropyl-phenyl)-amide, 1-(4-methoxy-benzenesulfonyl)-piperidine-4-carboxylic acid (4-trifluoromethoxy-phenyl)-amide, 1-benzenesulfonyl-piperidine-4-carboxylic acid (4-trifluoromethoxy-phenyl)-amide, 1-(4-methoxy-benzenesulfonyl)-piperidine-4-carboxylic acid (4-difluoromethoxy-phenyl)-amide, 1-(4-methoxy-benzenesulfonyl)-piperidine-4-carboxylic acid (4-isopropyl-phenyl)-amide, 1-(4-methoxy-benzenesulfonyl)-piperidine-4-carboxylic acid (4-chloro-2-fluoro-phenyl)-amide, 1-benzoyl-piperidine-4-carboxylic acid (4-isopropyl-phenyl)-amide, 1-(2-chloro-benzoyl)-piperidine-4-carboxylic acid (4-isopropyl-phenyl)-amide, 1-benzenesulfonyl-piperidine-4-carboxylic acid (1-phenyl-cyclopropylmethyl)-amide and 1-(toluene-4-sulfonyl)-piperidine-4-carboxylic acid (1-phenyl-cyclopentylmethyl)-amide.

Also preferred is a method for the treatment or prophylaxis of cardiovascular diseases, myocardial dysfunction or inflammation, which method comprises administering an effective amount of a compound according to formula (I) as described above or of a compound selected from the group consisting of: 1-(toluene-4-sulfonyl)-piperidine-4-carboxylic acid (4-trifluoromethoxy-phenyl)-amide, 1-(toluene-4-sulfonyl)-piperidine-4-carboxylic acid [2-(4-difluoromethoxy-phenyl)-ethyl]-amide, 1-benzenesulfonyl-piperidine-4-carboxylic acid (4-isopropyl-phenyl)-amide, 1-(toluene-4-sulfonyl)-piperidine-4-carboxylic acid (4-isopropyl-phenyl)-amide, 1-(4-methoxy-benzenesulfonyl)-piperidine-4-carboxylic acid (4-trifluoromethoxy-phenyl)-amide, 1-benzenesulfonyl-piperidine-4-carboxylic acid (4-trifluoromethoxy-phenyl)-amide, 1-(4-methoxy-benzenesulfonyl)-piperidine-4-carboxylic acid (4-difluoromethoxy-phenyl)-amide, 1-(4-methoxy-benzenesulfonyl)-piperidine-4-carboxylic acid (4-isopropyl-phenyl)-amide, 1-(4-methoxy-benzenesulfonyl)-piperidine-4-carboxylic acid (4-chloro-2-fluoro-phenyl)-amide, 1-benzoyl-piperidine-4-carboxylic acid (4-isopropyl-phenyl)-amide, 1-(2-chlorobenzoyl)-piperidine-4-carboxylic acid (4-isopropyl-phenyl)-amide, 1-benzenesulfonyl-piperidine-4-carboxylic acid (1-phenyl-cyclopropylmethyl)-amide and 1-(toluene-4-sulfonyl)-piperidine-4-carboxylic acid (1-phenyl-cyclopentylmethyl)-amide.

Particularly preferred is a method for the treatment or prophylaxis of diabetes, which method comprises administering an effective amount of a compound according to formula (I) as described above.

Moreover preferred is a method for the treatment or prophylaxis of diabetes Type II, which method comprises administering an effective amount of a compound according to formula (I) as described above.

A further preferred embodiment of the present invention are compounds according to formula (I) as described above, 1-(toluene-4-sulfonyl)-piperidine-4-carboxylic acid (4-trifluoromethoxy-phenyl)-amide, 1-(toluene-4-sulfonyl)-piperidine-4-carboxylic acid [2-(4-difluoromethoxy-phenyl)-ethyl]-amide, 1-benzenesulfonyl-piperidine-4-carboxylic acid (4-isopropyl-phenyl)-amide, 1-(toluene-4-sulfonyl)-piperidine-4-carboxylic acid (4-isopropyl-phenyl)-amide, 1-(4-methoxy-benzenesulfonyl)-piperidine-4-carboxylic acid (4-trifluoromethoxy-phenyl)-amide, 1-benzenesulfonyl-piperidine-4-carboxylic acid (4-trifluoromethoxy-phenyl)-amide, 1-(4-methoxy-benzenesulfonyl)-piperidine-4-carboxylic acid (4-difluoromethoxy-phenyl)-amide, 1-(4-methoxy-benzenesulfonyl)-piperidine-4-carboxylic acid (4-isopropyl-phenyl)-amide, 1-(4-methoxy-benzenesulfonyl)-piperidine-4-carboxylic acid (4-chloro-2-fluoro-phenyl)-amide, 1-benzoyl-piperidine-4-carboxylic acid (4-isopropyl-phenyl)-amide, 1-(2-chloro-benzoyl)-piperidine-4-carboxylic acid (4-isopropyl-phenyl)-amide, 1-benzenesulfonyl-piperidine-4-carboxylic acid (1-phenyl-cyclopropylmethyl)-amide or 1-(toluene-4-sulfonyl)-piperidine-4-carboxylic acid (1-phenyl-cyclopentylmethyl)-amide for the preparation of a medicament for the treatment or prophylaxis of nonalkoholic fatty liver disease or nonalkoholic steatohepatitis.

Preferred are compounds according to formula (I) as described above for the preparation of medicaments for the treatment or prophylaxis of nonalkoholic fatty liver disease or nonalkoholic steatohepatitis.

A further preferred embodiment of the present invention is the use of a compound according to formula (I) as described above or of a compound selected from the group consisting of: 1-(toluene-4-sulfonyl)-piperidine-4-carboxylic acid (4-trifluoromethoxy-phenyl)-amide, 1-(toluene-4-sulfonyl)-piperidine-4-carboxylic acid [2-(4-difluoromethoxy-phenyl)-ethyl]-amide, 1-benzenesulfonyl-piperidine-4-carboxylic acid (4-isopropyl-phenyl)-amide, 1-(toluene-4-sulfonyl)-piperidine-4-carboxylic acid (4-isopropyl-phenyl)-amide, 1-(4-methoxy-benzenesulfonyl)-piperidine-4-carboxylic acid (4-trifluoromethoxy-phenyl)-amide, 1-benzenesulfonyl-piperidine-4-carboxylic acid (4-trifluoromethoxy-phenyl)-amide, 1-(4-methoxy-benzenesulfonyl)-piperidine-4-carboxylic acid (4-difluoromethoxy-phenyl)-amide, 1-(4-methoxy-benzenesulfonyl)-piperidine-4-carboxylic acid (4-isopropyl-phenyl)-amide, 1-(4-methoxy-benzenesulfonyl)-piperidine-4-carboxylic acid (4-chloro-2-fluoro-phenyl)-amide, 1-benzoyl-piperidine-4-carboxylic acid (4-isopropyl-phenyl)-amide, 1-(2-chloro-benzoyl)-piperidine-4-carboxylic acid (4-isopropyl-phenyl)-amide for the preparation of a medicament for the treatment or prophylaxis of nonalkoholic fatty liver disease or nonalkoholic steatohepatitis.

Preferred is the use of a compound according to formula (I) as described above for the preparation of medicaments for the treatment or prophylaxis of nonalkoholic fatty liver disease or nonalkoholic steatohepatitis.

Also an object of the invention is a method for the treatment or prophylaxis of nonalkoholic fatty liver disease or nonalkoholic steatohepatitis, which method comprises administering an effective amount of a compound according to formula (I) as described above or of a compound selected from the group consisting of: 1-(toluene-4-sulfonyl)-piperidine-4-carboxylic acid (4-trifluoromethoxy-phenyl)-amide, 1-(toluene-4-sulfonyl)-piperidine-4-carboxylic acid [2-(4-difluoromethoxy-phenyl)-ethyl]-amide, 1-benzenesulfonyl-piperidine-4-carboxylic acid (4-isopropyl-phenyl)-amide, 1-(toluene-4-sulfonyl)-piperidine-4-carboxylic acid (4-isopropyl-phenyl)-amide, 1-(4-methoxy-benzenesulfonyl)-piperidine-4-carboxylic acid (4-trifluoromethoxy-phenyl)-amide, 1-benzenesulfonyl-piperidine-4-carboxylic acid (4-trifluoromethoxy-phenyl)-amide, 1-(4-methoxy-benzenesulfonyl)-piperidine-4-carboxylic acid (4-difluoromethoxy-phenyl)-amide, 1-(4-methoxy-benzenesulfonyl)-piperidine-4-carboxylic acid (4-isopropyl-phenyl)-amide, 1-(4-methoxy-benzenesulfonyl)-piperidine-4-carboxylic acid (4-chloro-2-fluoro-phenyl)-amide, 1-benzoyl-piperidine-4-carboxylic acid (4-isopropyl-phenyl)-amide, 1-(2-chloro-benzoyl)-piperidine-4-carboxylic acid (4-isopropyl-phenyl)-amide, 1-benzenesulfonyl-piperidine-4-carboxylic acid (1-phenyl-cyclopropylmethyl)-amide and 1-(toluene-4-sulfonyl)-piperidine-4-carboxylic acid (1-phenyl-cyclopentylmethyl)-amide.

Preferred is a method for the treatment or prophylaxis of nonalkoholic fatty liver disease or nonalkoholic steatohepatitis, which method comprises administering an effective amount of a compound according to formula (I) as described above.

Assay Procedures

Production of Human Full Length Hormone Sensitive Lipase-His[6]:

1) Cloning: cDNA was prepared from commercial human brain polyA+ RNA and used as a template in overlapping PCR to generate a full length human HSL ORF with a 3'-His6 tag. This full length insert was cloned into the pFast-BAC vector and the DNA-sequence of several single clones was verified. DNA from a correct full length clone with the 3'His6 tag was used to transform the *E. coli* strain DH10BAC. Resulting bacmid DNA was used to generate a titered baculovirus stock for protein generation. The sequence of the encoded HSL conforms to Swissprot entry Q05469, with the additional C-terminal His6-tag.

2) Protein purification: Culture: 5.5 L, High 5 cells expressing human full length HSL-His[6], 48 hr., containing 25 μM E-64. Cell count: $1.78 \times 10^{10}$ cells/ml, 90% viable. Cells were thawed. On ice, cells were suspended in Base Buffer containing 10% glycerol, 25 mM Tris-Cl, 300 mM NaCl, 10 mM imidazole, 10 mM 2-mercaptoethanol, 2 μg pepstatin/ml, 2 μg leupeptin/ml, 2 μg antipain/ml, pH 8.0 at 4° C. in a final volume of 475 ml with 3.75×107 cells/ml. Sanitation was done at 3×30 sec., Lubrol PX was added to 0.2% final concentration followed by stirring for 15 min. at 4° C. and centrifugation at 25 k×g, 60 min., 4° C. Soluble proteins were mixed with 60 ml of pre-washed and equilibrated Ni-NTA Agarose (Qiagen 30210) followed by tumbling end-over-end, 45 min., 4° C., centrifugation 1000 rpm 5 min and letting resin settle 5 min. Supernatant was removed, the resin washed in the centrifuge vessel using 5 volumes of Base Buffer containing 0.2% Lubrol PX. Centrifugation was done again, then the supernatant discarded. The resin was poured onto a 0.8 µm membrane in a disposable filter unit (Nalge 450-0080), and washed with 5 volumes of Base Buffer containing 0.2% Lubrol PX. It was then washed with 30 volumes of Base Buffer containing 60 mM imidazole pH 7.5 at 4° C. The protein was eluated with 5 volumes of 25 mM Tris-Cl, 300 mM NaCl, 200 mM imidazole, 10 mM 2-mercaptoethanol, pH 7.5 at 4° C. by tumbling resin with buffer end-over-end, 30 min., 4° C. The resin was captured on a 0.2 µm membrane disposable filter unit (Millipore SCGP U02 RE) and the eluate collected in the reservoir. The eluate was concentrated using a 30 k MWCO centrifugal filter device (Sartorius Vivascience Vivacell 100, VC1022), to 20 ml. It was then dialyzed overnight at 4° C., two times against 2 L of 10% glycerol, 25 mM Tris-Cl, 300 mM NaCl, 0.2 mM EDTA, 0.2 mM DTT, pH 7.5 at 4° C. The protein was filtered using a 0.22 µm disposable filter unit (Millipore SCGP00525). The protein concentration was calculated from absorbance at 280 nm, using 280=0.67 cm-1 mg-1. Yield was 235 mg, total. The protein was stored at −80° C.

Human Hormone-Sensitive Lipase (HSL) Enzyme Inhibition Assay:

HSL enzyme activity was measured by a colorimetric assay using 2,3-dimercapto-1-propanol tributyrate (Aldrich, St. Louis, Mo.) as a substrate. Typically, 1.5 mM 2,3-dimercapto-1-propanol tributyrate (DMPT) in 100 mM MOPS, pH 7.2, 0.2 mg/ml fatty acid-free BSA was prepared by sonication at 4° C. to homogenous suspension. Test compounds (2 mM stock in DMSO) were diluted 3 fold in series in DMSO. Compound solutions were diluted 24 fold in 1.5 mM DMPT containing solution and 18 ul per well was added to 384-well microplates (Corning Costar). Twelve microliters per well of human HSL (15 ug/ml) was added and the reaction mixture was incubated at 37° C. for 20 minutes. Six microliters of 12 mM dithio-bis-(2-nitrobenzoic acid) (DTNB) in DMSO plus 1.2% SDS and 0.6% Triton X-100 were added and the mixture was incubated at room temperature for 15 minutes. Product production was monitored by reading absorbance at 405 nm on an Envision Reader (PerkinElmer Life and Analytical Sciences, Shelton, Conn.).

Cellular Assay:

The following assay was used to measure the effect of the compounds to inhibit lipolysis in intact cells (adipocytes).

3T3-L1 pre-adipocyte cells were plated into 96-well plates at a density of 20,000 cells/well in 200 ul growth media (DMEM/10% Calf Serum/1× antibiotic-antimycotic) until confluent. At 48 hours post-confluency, the medium was removed and the cells were differentiated into adipocytes with differentiation medium (DMEM/10% FBS/1× Antibiotic-Antimycotic PLUS: 1 uM IBMX (3-Isobutyl-1-methylxanthine) Inhibitor of phosphodiesterases, 1 uM Dexamethasone, 1 uM Rosiglitazone, 10 ug/ml Insulin). The cells were incubated in said medium for 3 days and then medium was changed to post-differentiation medium (DMEM/10% FBS PLUS: 10 ug/ml Insulin) and the cells were incubated for an additional 3 days. The medium was then changed to maintenance media (DMEM/10% FBS). The cells were fed every 3 days with maintenance media until use. The lipolysis assay may be performed on day 9-14 after the initiation of differentiation in 96 well plates.

The lipolysis assay was performed as follows. The adipocytes were washed 2× with 200 ul Krebs Ringer Bicarbonate Hepes buffer (KRBH)/3% BSA. Test compounds were at 10 mM in DMSO and were initially diluted to 5 mM in DMSO. They were then serially diluted 5-fold in DMSO (5 mM to 320 pM). Each compound was then diluted 200-fold into KRBH/3% BSA (0.5% DMSO final). The resulting solutions range from 25 uM to 1.6 pM final. One hundred fifty ul of the diluted compounds were added to each well (in triplicate) and the cells were preincubated 30 min at 37° C. Forskolin (50 uM final) was added to the wells and the cells were incubated 120 minutes at 37° C. One hundred ul was collected into a new 96-well plate for glycerol analysis. The amount of glycerol produced was determined using a glycerol determination kit (Sigma).

| Examples | HSL hum IC$_{50}$ (uM) |
|---|---|
| 1 | 0.08 |
| 2 | 0.24 |
| 3 | 12 |
| 4 | 3 |
| 5 | 0.12 |
| 6 | 0.12 |
| 7 | 0.07 |
| 8 | 0.8 |
| 9 | 0.35 |
| 10 | 0.2 |
| 11 | 0.08 |
| 12 | 0.92 |
| 13 | 0.12 |
| 14 | 0.16 |
| 15 | 0.47 |
| 16 | 0.04 |
| 17 | 0.77 |
| 18 | 0.55 |
| 19 | 0.74 |
| 20 | 0.17 |
| 21 | 0.2 |
| 22 | 0.7 |
| 23 | 0.11 |
| 24 | 1.14 |
| 25 | 0.09 |
| 26 | 0.22 |
| 27 | 0.95 |
| 28 | 0.66 |
| 29 | 0.28 |
| 30 | 0.18 |
| 31 | 0.48 |
| 32 | 0.92 |
| 33 | 0.13 |
| 34 | 0.09 |
| 35 | 1.13 |
| 36 | 0.05 |
| 37 | 0.6 |
| 38 | 0.02 |
| 39 | 0.04 |
| 40 | 0.07 |
| 41 | 0.32 |
| 42 | 0.04 |
| 43 | 0.81 |
| 44 | 0.62 |
| 45 | 0.15 |
| 46 | 0.04 |
| 47 | 0.07 |
| 48 | 0.04 |
| 49 | 0.09 |
| 50 | 0.81 |
| 51 | 0.33 |
| 52 | 0.86 |
| 53 | 0.66 |
| 54 | 0.08 |
| 55 | 1.42 |
| 56 | 0.26 |
| 57 | 0.25 |
| 58 | 0.54 |
| 59 | 0.29 |

| Examples | HSL hum IC$_{50}$ (uM) |
|---|---|
| 60 | 0.07 |
| 61 | 0.64 |
| 62 | 0.53 |
| 63 | 1.09 |
| 64 | 1.49 |

Compounds as described above have IC$_{50}$ values between 0.005 uM and 1000 uM, preferred compounds have IC$_{50}$ values between 0.01 uM and 15 uM, particularly preferred compounds have IC$_{50}$ values between 0.01 uM and 0.5 uM. These results have been obtained by using the foregoing HSL enzyme inhibition assay (uM means microMolar).

The compounds of formula (I), 1-(toluene-4-sulfonyl)-piperidine-4-carboxylic acid (4-trifluoromethoxy-phenyl)-amide, 1-(toluene-4-sulfonyl)-piperidine-4-carboxylic acid [2-(4-difluoromethoxy-phenyl)-ethyl]-amide, 1-benzenesulfonyl-piperidine-4-carboxylic acid (4-isopropyl-phenyl)-amide, 1-(toluene-4-sulfonyl)-piperidine-4-carboxylic acid (4-isopropyl-phenyl)-amide, 1-(4-methoxy-benzenesulfonyl)-piperidine-4-carboxylic acid (4-trifluoromethoxy-phenyl)-amide, 1-benzenesulfonyl-piperidine-4-carboxylic acid (4-trifluoromethoxy-phenyl)-amide, 1-(4-methoxy-benzenesulfonyl)-piperidine-4-carboxylic acid (4-difluoromethoxy-phenyl)-amide, 1-(4-methoxy-benzenesulfonyl)-piperidine-4-carboxylic acid (4-isopropyl-phenyl)-amide, 1-(4-methoxy-benzenesulfonyl)-piperidine-4-carboxylic acid (4-chloro-2-fluoro-phenyl)-amide, 1-benzoyl-piperidine-4-carboxylic acid (4-isopropyl-phenyl)-amide, 1-(2-chloro-benzoyl)-piperidine-4-carboxylic acid (4-isopropyl-phenyl)-amide, 1-benzenesulfonyl-piperidine-4-carboxylic acid (1-phenyl-cyclopropylmethyl)-amide, 1-(toluene-4-sulfonyl)-piperidine-4-carboxylic acid (1-phenyl-cyclopentylmethyl)-amide and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I), 1-(toluene-4-sulfonyl)-piperidine-4-carboxylic acid (4-trifluoromethoxy-phenyl)-amide, 1-(toluene-4-sulfonyl)-piperidine-4-carboxylic acid [2-(4-difluoromethoxy-phenyl)-ethyl]-amide, 1-benzenesulfonyl-piperidine-4-carboxylic acid (4-isopropyl-phenyl)-amide, 1-(toluene-4-sulfonyl)-piperidine-4-carboxylic acid (4-isopropyl-phenyl)-amide, 1-(4-methoxy-benzenesulfonyl)-piperidine-4-carboxylic acid (4-trifluoromethoxy-phenyl)-amide, 1-benzenesulfonyl-piperidine-4-carboxylic acid (4-trifluoromethoxy-phenyl)-amide, 1-(4-methoxy-benzenesulfonyl)-piperidine-4-carboxylic acid (4-difluoromethoxy-phenyl)-amide, 1-(4-methoxy-benzenesulfonyl)-piperidine-4-carboxylic acid (4-isopropyl-phenyl)-amide, 1-(4-methoxy-benzenesulfonyl)-piperidine-4-carboxylic acid (4-chloro-2-fluoro-phenyl)-amide, 1-benzoyl-piperidine-4-carboxylic acid (4-isopropyl-phenyl)-amide, 1-(2-chloro-benzoyl)-piperidine-4-carboxylic acid (4-isopropyl-phenyl)-amide, 1-benzenesulfonyl-piperidine-4-carboxylic acid (1-phenyl-cyclopropylmethyl)-amide, 1-(toluene-4-sulfonyl)-piperidine-4-carboxylic acid (1-phenyl-cyclopentylmethyl)-amide and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention, the compounds of formula (I), 1-(toluene-4-sulfonyl)-piperidine-4-carboxylic acid (4-trifluoromethoxy-phenyl)-amide, 1-(toluene-4-sulfonyl)-piperidine-4-carboxylic acid [2-(4-difluoromethoxy-phenyl)-ethyl]-amide, 1-benzenesulfonyl-piperidine-4-carboxylic acid (4-isopropyl-phenyl)-amide, 1-(toluene-4-sulfonyl)-piperidine-4-carboxylic acid (4-isopropyl-phenyl)-amide, 1-(4-methoxy-benzenesulfonyl)-piperidine-4-carboxylic acid (4-trifluoromethoxy-phenyl)-amide, 1-benzenesulfonyl-piperidine-4-carboxylic acid (4-trifluoromethoxy-phenyl)-amide, 1-(4-methoxy-benzenesulfonyl)-piperidine-4-carboxylic acid (4-difluoromethoxy-phenyl)-amide, 1-(4-methoxy-benzenesulfonyl)-piperidine-4-carboxylic acid (4-isopropyl-phenyl)-amide, 1-(4-methoxy-benzenesulfonyl)-piperidine-4-carboxylic acid (4-chloro-2-fluoro-phenyl)-amide, 1-benzoyl-piperidine-4-carboxylic acid (4-isopropyl-phenyl)-amide, 1-(2-chloro-benzoyl)-piperidine-4-carboxylic acid (4-isopropyl-phenyl)-amide, 1-benzenesulfonyl-piperidine-4-carboxylic acid (1-phenyl-cyclopropylmethyl)-amide, 1-(toluene-4-sulfonyl)-piperidine-4-carboxylic acid (1-phenyl-cyclopentylmethyl)-amide and their pharmaceutically acceptable salts can be used for the prophylaxis or treatment of diabetes, metabolic syndrome, dyslipidemia, atherosclerosis and obesity. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

In case the preparative examples are obtained as a mixture of enantiomers, the pure enantiomers can be separated

EXAMPLE 1

1-(Toluene-4-sulfonyl)-piperidine-4-carboxylic acid (4-trifluoromethoxy-phenyl)-amide

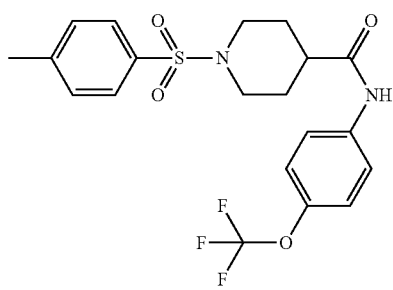

1-[(4-Methylphenyl)sulfonyl]-4-piperidinecarboxylic acid (0.283 g) and 2-chloro-4,6-dimethoxy-1,3,5-triazine (CDMT) in acetonitrile (40 ml) were treated at RT and under an argon atmosphere with N-methyl-morpholine (0.2 g) and the mixture was stirred for 2 h at RT. 4-trifluoromethoxy-aniline (0.176 g) was then added and stirring was continued for 20 h at RT until completion of the reaction. The reaction mixture was partitioned between ethyl acetate and aqueous 1M HCl, the layers were separated and the organic layer washed with 2M aqueous $KHCO_3$ then dried over $Na_2SO_4$. The solvent was evaporated off, the residue purified by flash chromatography (AcOEt/heptane, gradient from 0 to 30%) to give 1-(toluene-4-sulfonyl)-piperidine-4-carboxylic acid (4-trifluoromethoxy-phenyl)-amide (0.298 g) as a white solid. MS (ESI): 443.1 (MH+).

EXAMPLE 2

1-Benzenesulfonyl-piperidine-4-carboxylic acid (6-isopropyl-pyridin-3-yl)-amide

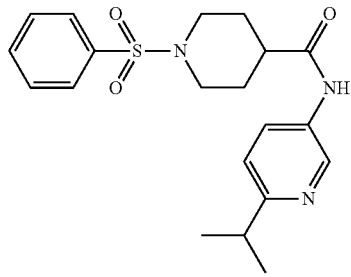

This material was obtained in analogy to example 1 from 1-(phenylsulfonyl)-4-piperidinecarboxylic acid (0.094 g) and 6-isopropyl-pyridin-3-ylamine (0.084 g) to give the desired 1-benzenesulfonyl-piperidine-4-carboxylic acid (6-isopropyl-pyridin-3-yl)-amide (0.039 g) as a white solid. MS (ESI): 388.2 (MH+).

EXAMPLE 3

1-Benzenesulfonyl-piperidine-4-carboxylic acid (6-methoxy-pyridazin-3-yl)-amide

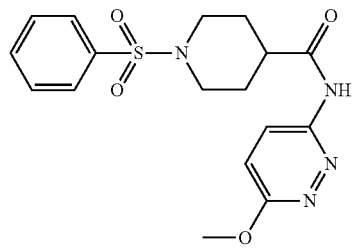

This material was obtained in analogy to example 1 from 1-(phenylsulfonyl)-4-piperidinecarboxylic acid (0.094 g) and 6-methoxy-pyridazin-3-ylamineylamine (0.044 g) to give the desired 1-benzenesulfonyl-piperidine-4-carboxylic acid (6-methoxy-pyridazin-3-yl)-amide (0.012 g) as a off-white solid. MS (ESI): 377.1 (MH+).

EXAMPLE 4

(rac)-1-(Toluene-4-sulfonyl)-piperidine-4-carboxylic acid ethyl-[4-(2,2,2-trifluoro-1-methyl-ethoxy)-phenyl]-amide

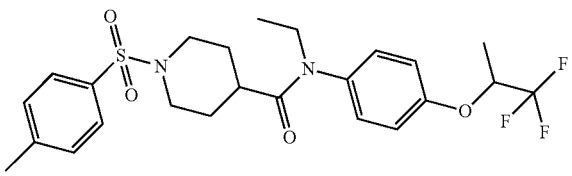

This material was obtained in analogy to example 1 from 1-[(4-methylphenyl)sulfonyl]-4-piperidinecarboxylic acid (0.14 g) and (rac)-ethyl-[4-(2,2,2-trifluoro-1-methyl-ethoxy)-phenyl]-amine (0.116 g) using EDC as coupling reagent, DMAP as base and THF as solvent to give the desired (rac)-1-(toluene-4-sulfonyl)-piperidine-4-carboxylic acid ethyl-[4-(2,2,2-trifluoro-1-methyl-ethoxy)-phenyl]-amide (0.187 g) as a crystalline white solid. MS (ESI): 499.3 (MH+).

(i) Preparation of Starting Material, (rac)-ethyl-[4-(2,2,2-trifluoro-1-methyl-ethoxy)-phenyl]-amine This material was prepared from (rac)-4-(2,2,2-trifluoro-1-methyl-ethoxy)-phenylamine by, first a standard acetylation reaction (acetic anhydride, DMAP as base) followed by reduction with $LiAlH_4$ using standard literature procedures.

(ii) Preparation of (rac)-4-(2,2,2-trifluoro-1-methyl-ethoxy)-phenylamine a) To a solution of 1-fluoro-4-nitro-benzene (4.24 g) and (rac)-1,1,1-trifluoro-propan-2-ol (4.563 g) in acetonitrile (50 ml) under an argon atmosphere was added at RT $Cs_2CO_3$ (13.04 g) and the mixture was refluxed for 10 h. It was then acidified with diluted aqueous HCL and partitioned between ethyl acetate and water. The layers were separated, dried over Na₂SO₄ and the solvent was then evaporated off to give (rac)-1-nitro-4-(2,2,2-trifluoro-1-methyl-ethoxy)-benzene as brown oil (6.74 g) that was used without further purification.

b) (rac)-1-nitro-4-(2,2,2-trifluoro-1-methyl-ethoxy)-benzene (6.74 g) in methanol (80 ml) were hydrogenated at RT over Pd/C (10%, 500 mg) under atmospheric pressure for 12 h. The catalyst was filtered off and filtrate concentrated in vacuo to give the desired (rac)-4-(2,2,2-trifluoro-1-methyl-ethoxy)-phenylamine (5.8 g) as a light yellow oil. MS (ESI): 206.1 (MH⁺).

EXAMPLE 5

(rac)-1-(Toluene-4-sulfonyl)-piperidine-4-carboxylic acid methyl-[4-(2,2,2-trifluoro-1-methyl-ethoxy)-phenyl]-amide

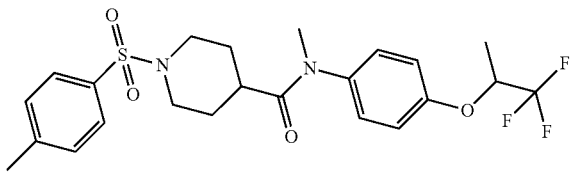

This material was obtained in analogy to example 4 from 1-[(4-methylphenyl)sulfonyl]-4-piperidinecarboxylic acid (0.014 g) and (rac)-methyl-[4-(2,2,2-trifluoro-1-methyl-ethoxy)-phenyl]-amine (0.11 g) to give the desired (rac)-1-(toluene-4-sulfonyl)-piperidine-4-carboxylic acid methyl-[4-(2,2,2-trifluoro-1-methyl-ethoxy)-phenyl]-amide (0.123 g) as a crystalline off-white solid. MS (ESI): 485.3 (MH⁺).

Preparation of Starting Material, (rac)-methyl-[4-(2,2,2-trifluoro-1-methyl-ethoxy)-phenyl]-amine This material was prepared from (rac)-4-(2,2,2-trifluoro-1-methyl-ethoxy)-phenylamine by, first an standard methoxycarbonylation reaction with dimethyl dicarbonate in methylene chloride (at RT and 12 h stirring) followed by reduction with LiAlH4 according to standard literature procedures.

EXAMPLE 6

(rac)-1-(Toluene-4-sulfonyl)-piperidine-4-carboxylic acid [6-(2,2,2-trifluoro-1-methyl-ethoxy)-pyridin-3-yl]-amide

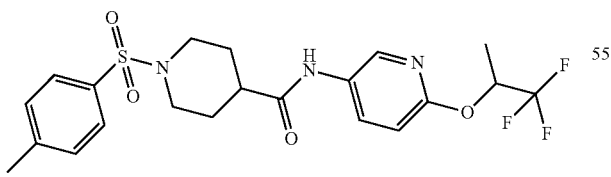

This material was obtained in analogy to example 4 from 1-[(4-methylphenyl)sulfonyl]-4-piperidinecarboxylic acid (0.14 g) and (rac)-6-(2,2,2-trifluoro-1-methyl-ethoxy)-pyridin-3-ylamine (0.1 g) to give the desired (rac)-1-(toluene-4-sulfonyl)-piperidine-4-carboxylic acid [6-(2,2,2-trifluoro-1-methyl-ethoxy)-pyridin-3-yl]-amide (0.2 g) as a crystalline off-white solid. MS (ESI): 472.1 (MH⁺).

Preparation of Starting Material, (rac)-6-(2,2,2-trifluoro-1-methyl-ethoxy)-pyridin-3-ylamine i) To a solution of 2-chloro-5-nitro-pyridine (1.74 g) and 1,1,1-trifluoro-propan-2-ol (1.097 g) in DMF (15 ml) under an argon atmosphere was added under ice cooling NaH (0.528 g, 55% suspension in oil). The mixture was stirred for 3 h at RT then partitioned between diethyl ether and water, the layers were separated dried over Na₂SO₄ and the solvent was evaporated off to give (rac)-5-nitro-2-(2,2,2-trifluoro-1-methyl-ethoxy)-pyridine as brown oil (2.28 g) that was used in the next step without further purification.

ii) (rac)-5-Nitro-2-(2,2,2-trifluoro-1-methyl-ethoxy)-pyridine (2.23 g) in methanol (30 ml) was hydrogenated over Pd/C (10%, 500 mg) at RT and at atmospheric pressure for 12 h. The catalyst was filtered off and the solvent removed in vacuo to give the desired (rac)-6-(2,2,2-trifluoro-1-methyl-ethoxy)-pyridin-3-ylamine (1.91 g) as a brown oil. MS (ESI): 270.0 (MH⁺).

EXAMPLE 7

1-(Toluene-4-sulfonyl)-piperidine-4-carboxylic acid (4-isopropoxy-phenyl)-amide

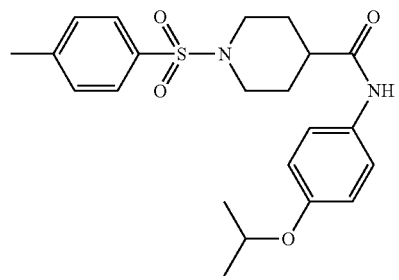

This material was obtained in analogy to example 1 from 1-[(4-methylphenyl)sulfonyl]-4-piperidinecarboxylic acid (0.142 g) (and 4-isopropoxy-phenylamine (0.079 g) to give the desired 1-(toluene-4-sulfonyl)-piperidine-4-carboxylic acid (4-isopropoxy-phenyl)-amide (0.12 g) as an off-white solid. MS (ESI): 417.3 (MH⁺).

EXAMPLE 8

1-(2-Cyclopropyl-acetyl)-piperidine-4-carboxylic acid (4-isopropyl-phenyl)-amide

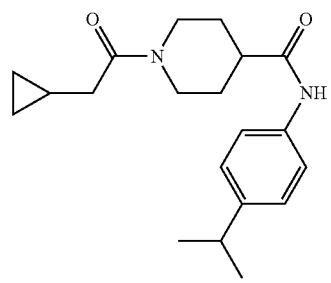

Step A): 4-(4-Isopropyl-phenylcarbamoyl)-piperidine-1-carboxylic acid tert-butyl ester Piperidine-1,4-dicarboxylic acid mono-tert-butyl ester (2.293 g) and 2-chloro-4,6-dimethoxy-1,3,5-triazine (1.84 g) in acetonitrile (50 ml) were treated under ice cooling and an argon atmosphere with N-methyl-morpholine (3.034 g) and the mixture was stirred for 2 h at 0° C. Then 4-isopropyl-phenylamine (1.42 g) in acetonitrile was added dropwise and the reaction mixture was stirred at RT for 48 h. The reaction mixture was partitioned between ethyl acetate and aqueous 1M HCl, the layers were separated and the aqueous layer washed with 2M aqueous $KHCO_3$ then dried over $Na_2SO_4$. The solvent was evaporated off. The residue was then triturated with AcOEt/diethyl ether/heptane to give the desired 4-(4-isopropyl-phenylcarbamoyl)-piperidine-1-carboxylic acid tert-butyl ester (1.68 g) as white solid. MS (ESI): 347.28 (MH$^+$)

Step B): Piperidine-4-carboxylic acid (4-isopropyl-phenyl)-amide 4-(4-Isopropyl-phenylcarbamoyl)-piperidine-1-carboxylic acid tert-butyl ester (1.68 g) was dissolved in methylene chloride (50 ml), trifluoroacetic acid (2.75 g) was added at 0° C. and under an argon atmosphere and the mixture was stirred for 12 h at RT. Further trifluoroacetic acid (1.1 g) was added and stirring was continued for 1.5 h to complete the reaction. The reaction mixture was partitioned between methylene chloride and aqueous 1M NaOH, the layers were separated and the aqueous layer washed with 2M aqueous $KHCO_3$ then dried over $Na_2SO_4$. The solvent was evaporated off, the residue was triturated with diethyl ether/heptane to give the desired piperidine-4-carboxylic acid (4-isopropyl-phenyl)-amide (1 g) as a white solid that was directly used in the next step.

Step C): 1-(2-Cyclopropyl-acetyl)-piperidine-4-carboxylic acid (4-isopropyl-phenyl)-amide Cyclopropylacetic acid (0.055 g) was dissolved in acetonitrile (6 ml), ethyl-diisopropyl-amine (0.129 g), BOP (0.221 g) was added at RT under an argon atmosphere and the mixture was stirred for 30 minutes at RT. Then piperidine-4-carboxylic acid (4-isopropyl-phenyl)-amide (0.123 g) in acetonitrile (2 ml) was added dropwise at RT and the reaction mixture was stirred for 12 h until completion of the reaction. It was then partitioned between ethyl acetate and aqueous 1M HCl, the layers were separated and the aqueous layer washed with 2M aqueous $KHCO_3$ then dried over $Na_2SO_4$. The solvent was evaporated off, the residue purified by flash chromatography (AcOEt/heptane, gradient from 0 to 60%) to give 1-(2-cyclopropyl-acetyl)-piperidine-4-carboxylic acid (4-isopropyl-phenyl)-amide (0.158 g) as an off-white solid. MS (ESI): 329.17 (MH$^+$).

EXAMPLE 9

1-(3-Cyclopropyl-propionyl)-piperidine-4-carboxylic acid (4-isopropyl-phenyl)-amide

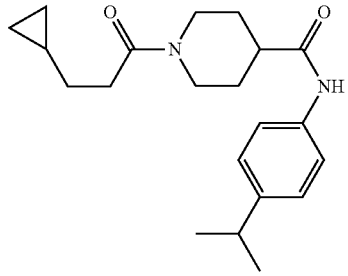

This material was prepared in analogy to example 8 step C) from piperidine-4-carboxylic acid (4-isopropyl-phenyl)-amide (0.123 g), 3-cyclopropylpropionic acid (0.057 g) as white solid (0.124 g). MS (ESI): 343.17 (MH$^+$).

EXAMPLE 10

1-(3-Cyclopropyl-propionyl)-piperidine-4-carboxylic acid (4-isopropyl-phenyl)-amide

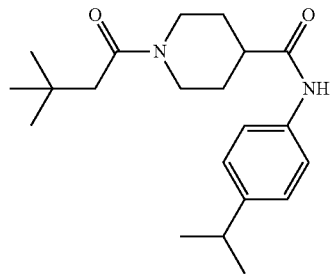

This material was prepared in analogy to example 8 step C) from piperidine-4-carboxylic acid (4-isopropyl-phenyl)-amide (0.123 g), 3,3-dimethyl-butyric acid (0.058 g) as white solid (0.135 g). MS (ESI): 345.29 (MH$^+$).

EXAMPLE 11

Racemic Mixture of Example 11a which is (2S,4S)-1-(2-Chloro-benzenesulfonyl)-2-hydroxymethyl-piperidine-4-carboxylic acid methyl-(4-trifluoromethoxy-phenyl)-amide and Example 11b which is (2R,4R)-1-(2-Chloro-benzenesulfonyl)-2-hydroxymethyl-piperidine-4-carboxylic acid methyl-(4-trifluoromethoxy-phenyl)-amide

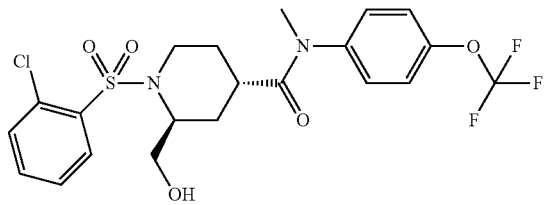

EXAMPLE 11a

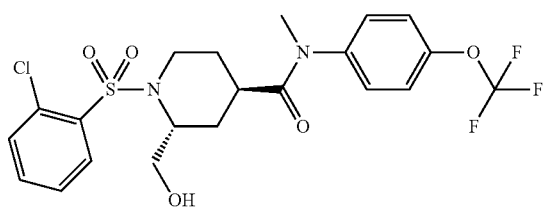

EXAMPLE 11b

A racemic mixture of (2S,4S)-1-(2-Chloro-benzenesulfonyl)-2-hydroxymethyl-piperidine-4-carboxylic acid (4-trifluoromethoxy-phenyl)-amide (see Example 36a) and (2R, 4R)-1-(2-Chloro-benzenesulfonyl)-2-hydroxymethylpiperidine-4-carboxylic acid (4-trifluoromethoxy-phenyl)-amide) (see Example 36b) (0.083 g) was dissolved in THF (5 ml) at RT under an argon atmosphere, potassium tert-butoxide (0.037 g) was added and the mixture was stirred 1 h. at RT. Then methyl iodide (2.32 g) was added and the mixture was stirred further 40 min at RT. The mixture was then made acidic with 3M aqueous HCl, stirred 5 min, absorbed on silica gel and the desired product was isolated by flash chromatography (AcOEt/heptane, gradient from 0 to 50%) to give a racemic mixture of (2S,4S)-1-(2-Chloro-benzenesulfonyl)-2-hydroxymethyl-piperidine-4-carboxylic acid methyl-(4-trifluoromethoxy-phenyl)-amide and (2R,4R)-1-(2-Chloro-benzenesulfonyl)-2-hydroxymethyl-piperidine-4-carboxylic acid methyl-(4-trifluoromethoxy-phenyl)-amide (0.026 g) as viscous oil. MS (ESI): 489.08 [(M-H$_2$O)H$^+$].

EXAMPLE 12

1-Benzenesulfonyl-4-(3-methoxy-propyl)-piperidine-4-carboxylic acid (4-isopropoxy-phenyl)-amide

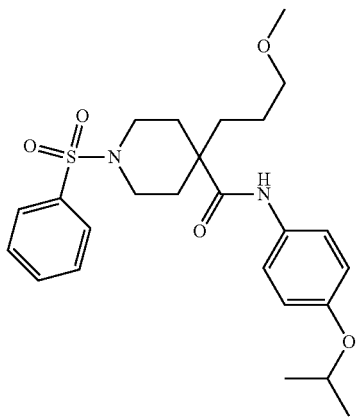

Step A): 4-(3-Methoxy-propyl)-piperidine-1,4-dicarboxylic acid 1-tert-butyl ester 4-ethyl ester To a pre-cooled THF solution (200 ml) under an argon atmosphere was added at −5° C. LDA (2M in THF/heptane/ethylbenzene, 16.24 ml) then dropwise piperidine-1,4-dicarboxylic acid 1-tert-butyl ester 4-ethyl ester (4.4 g, 4.2 ml) in THF (50 ml). The mixture was stirred between −5° C. to 0° C. for 3 hour and 1-bromo-3-methoxypropane (4.97 g) was added slowly at 0° C. The mixture was then stirred overnight at RT, the solvent was evaporated off, the residue taken up in ethyl acetate and washed with water then brine. The layers were separated, the organic layer dried over sodium sulphate and then evaporated off to give the desired 4-(3-methoxy-propyl)-piperidine-1,4-dicarboxylic acid 1-tert-butyl ester 4-ethyl ester a light brown oil (6.058 g) oil that was used in next reaction step without further purification.

Step B): 4-(3-Methoxy-propyl)-piperidine-4-carboxylic acid ethyl ester 4-(3-Methoxy-propyl)-piperidine-1,4-dicarboxylic acid 1-tert-butyl ester 4-ethyl ester (6 g) was dissolved in methylene chloride (200 ml) under an argon atmosphere, TFA (35.6 ml) was added and the reaction mixture was stirred for 3 hours at RT. The solvent together with most of the TFA was evaporated off, the residue dissolved in methylene chloride (800 ml) and treated with 2M KHCO$_3$ under ice cooling. The layers were separated, the organic layer was washed with water and brine, dried over sodium sulphate and concentrated in vacuo to give 3.63 g of 4-(3-methoxy-propyl)-piperidine-4-carboxylic acid ethyl ester as a light brown oil which was used in next reaction step without further purification.

Step C): 1-Benzenesulfonyl-4-(3-methoxy-propyl)-piperidine-4-carboxylic acid ethyl ester 4-(3-Methoxy-propyl)-piperidine-4-carboxylic acid ethyl ester (3.36 g) was dissolved under an argon atmosphere in pyridine (80 ml), benzensulfonyl chloride (2.59 g) was added and the mixture was stirred overnight at RT. The pyridine was evaporated off, the residue dissolved in ethyl acetate and washed with 0,05M HCl and brine. The layers were separated, the organic layer was dried over sodium sulphate, the solvent was then removed in vacuo and the crude oil was purified by flash chromatography over silica gel (AcOEt/heptane gradient from 0 to 25%) to give 1-benzenesulfonyl-4-(3-methoxy-propyl)-piperidine-4-carboxylic acid ethyl ester (4.15 g) as a yellow semi-solid. MS (ESI): 370.16 (MH$^+$).

Step D) 1-Benzenesulfonyl-4-(3-methoxy-propyl)-piperidine-4-carboxylic acid (4-isopropoxy-phenyl)-amide 1-Benzenesulfonyl-4-(3-methoxy-propyl)-piperidine-4-carboxylic acid ethyl ester (0.3 g) was dissolved under an argon atmosphere in toluene (10 ml), 4-(isopropoxy)-aniline (0.147 g) was added followed by dimethylaluminium chloride in heptane (1.8 ml, 0.9 molar). The mixture was refluxed 3 hours, more 4-(isopropox)-aniline (0.173 g) and dimethylaluminium chloride in heptane (1.8 ml) was added and refluxing was continued for 3 hours. The reaction mixture was then cooled to RT, water (1 ml) was added and the mixture was stirred for 10 minutes. The solvent was evaporated off, the residue absorbed on silica gel and the desired 1-benzenesulfonyl-4-(3-methoxy-propyl)-piperidine-4-carboxylic acid (4-isopropoxy-phenyl)-amide (0.047 g) was isolated by flash-chromatography (AcOEt/heptane, gradient from 0 to 25%) as a white solid. MS (ESI): 475.22 (MH$^+$).

EXAMPLE 13

1-(Toluene-4-sulfonyl)-piperidine-4-carboxylic acid (4-difluoromethoxy-phenyl)-amide

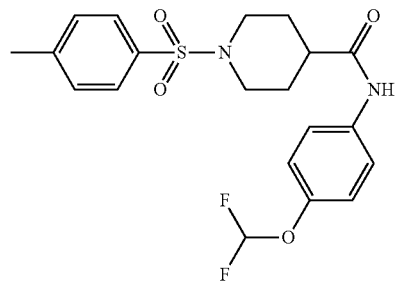

This material was obtained in analogy to example 1 from 1-[(4-Methylphenyl)sulfonyl]-4-piperidinecarboxylic acid (0.142 g) and 4-difluoromethoxy-phenylamine (0.08 g) to give the desired 1-(toluene-4-sulfonyl)-piperidine-4-carboxylic acid (4-difluoromethoxy-phenyl)-amide (0.069 g) as a white solid. MS (ESI): 425.20 (MH$^+$).

EXAMPLE 14

1-(Toluene-4-sulfonyl)-piperidine-4-carboxylic acid [4-(2,2,2-trifluoro-ethoxy)-phenyl]-amide

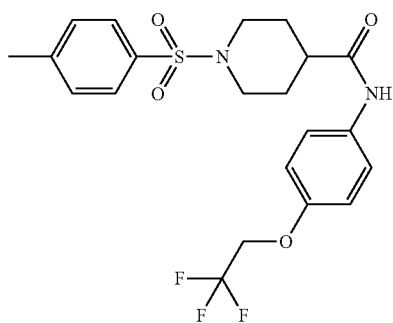

This material was obtained in analogy to example 1 from 1-[(4-methylphenyl)sulfonyl]-4-piperidinecarboxylic acid (0.099 g) and 4-(2,2,2-trifluoro-ethoxy)-phenylamine (0.08 g) to give the desired 1-(toluene-4-sulfonyl)-piperidine-4-carboxylic acid [4-(2,2,2-trifluoro-ethoxy)-phenyl]-amide (0.1 g) as a light brown solid. MS (ESI): 435.18 (MH$^+$).

EXAMPLE 15

1-(Toluene-4-sulfonyl)-piperidine-4-carboxylic acid (2-fluoro-4-isopropoxy-phenyl)-amide

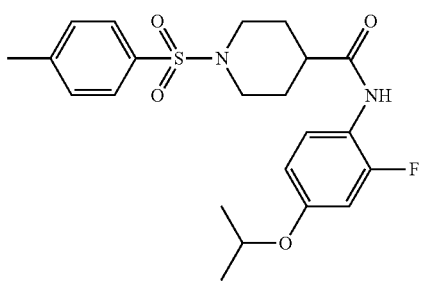

This material was obtained in analogy to example 1 from 1-[(4-methylphenyl)sulfonyl]-4-piperidinecarboxylic acid (0.099 g) and 2-fluoro-4-isopropoxyoxy-phenylamine (0.072 g) to give the desired 1-(toluene-4-sulfonyl)-piperidine-4-carboxylic acid (2-fluoro-4-isopropoxy-phenyl)-amide (0.1 g) as a light brown solid. MS (ESI): 435.18 (MH$^+$).

EXAMPLE 16

1-(Toluene-4-sulfonyl)-piperidine-4-carboxylic acid methyl-(4-trifluoromethoxy-phenyl)-amide

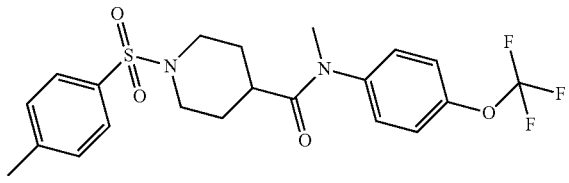

This material was obtained in analogy to example 4 from 1-[(4-methylphenyl)sulfonyl]-4-piperidinecarboxylic acid (0.283 g) and methyl-(4-trifluoromethoxy-phenyl)-amine (0.187 g) to give the desired 1-(toluene-4-sulfonyl)-piperidine-4-carboxylic acid methyl-[4-(2,2,2-trifluoro-1-methyl-ethoxy)-phenyl]-amide (0.318 g) as a crystalline off-white solid. MS (ESI): 457.3 (MH$^+$).

EXAMPLE 17

1-(Toluene-4-sulfonyl)-piperidine-4-carboxylic acid (2,3-dihydro-benzofuran-5-yl)-amide

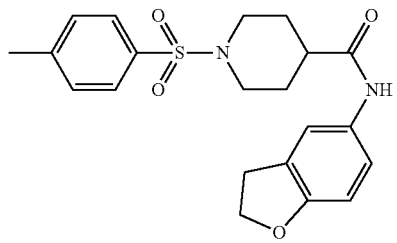

This material was obtained in analogy to example 1 from 1-[(4-methylphenyl)sulfonyl]-4-piperidinecarboxylic acid (0.099 g) 2,3-dihydro-benzofuran-5-ylamine (0.061 g) to give the desired 1-(toluene-4-sulfonyl)-piperidine-4-carboxylic acid (2,3-dihydro-benzofuran-5-yl)-amide (0.08) as a light off-white solid. MS (ESI): 401.19 (MH$^+$).

EXAMPLE 18

4-Fluoro-1-(toluene-4-sulfonyl)-piperidine-4-carboxylic acid (4-trifluoromethoxy-phenyl)-amide

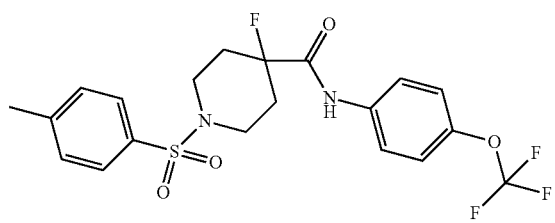

Step A): 4-Fluoro-1-(toluene-4-sulfonyl)-piperidine-4-carboxylic acid ethyl ester 4-Fluoro-piperidine-4-carboxylic acid ethyl ester (1.263 g), synthesis described in patent application US2004/10013, was dissolved in pyridine (70 ml) and p-toluenesulfonyl chloride (1.512 g) was added and the mixture was stirred at RT for 48 h under an argon atmosphere. Then the solvent was evaporated off, the residue partitioned between AcOEt and aqueous HCl, the organic layer was separated, washed with brine, dried over sodium sulphate and concentrated in vacuo to give a brown oil which was purified by flash chromatography (AcOEt/Heptane, gradient from 0 to 25%) to give the desired 4-fluoro-1-(toluene-4-sulfonyl)-piperidine-4-carboxylic acid ethyl ester (2.086 g) as a white solid. MS (ESI): 330.0 (MH$^+$).

Step B): 4-Fluoro-1-(toluene-4-sulfonyl)-piperidine-4-carboxylic acid

4-Fluoro-1-(toluene-4-sulfonyl)-piperidine-4-carboxylic acid ethyl ester (2.08 g) was dissolved in MeOH (70 ml) at RT and under an argon atmosphere and 3M aqueous NaOH (8.42 ml) was added at RT and the mixture was stirred for 12 h at RT. The solvent was evaporated and 3M HCl was slowly added to adjust the pH between 1-2. The mixture was then extracted twice with AcOEt, the organic layers were collected, washed with brine, dried over sodium sulphate and concentrated to give crude 4-fluoro-1-(toluene-4-sulfonyl)-piperidine-4-carboxylic acid (1.9 g) as a light brown solid which was used in next reaction step without further purification.

Step C): 4-Fluoro-1-(toluene-4-sulfonyl)-piperidine-4-carboxylic acid (4-trifluoromethoxy-phenyl)-amide This material was made in analogy to example 1 from 4-fluoro-1-(toluene-4-sulfonyl)-piperidine-4-carboxylic acid (0.2 g) and 4-trifluoromethoxy-aniline (0.118 g) to give the desired 4-fluoro-1-(toluene-4-sulfonyl)-piperidine-4-carboxylic acid (4-trifluoromethoxy-phenyl)-amide (0.1 g) as a white solid. MS (ESI): 461.2 MH$^+$).

EXAMPLE 19

4-Fluoro-1-(toluene-4-sulfonyl)-piperidine-4-carboxylic acid (4-isopropoxy-phenyl)-amide

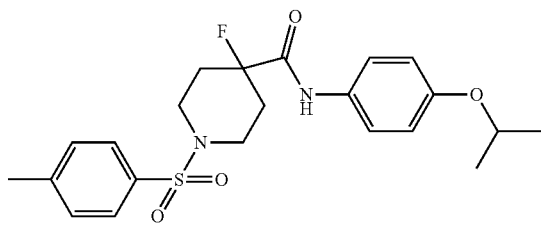

This materiel was made in analogy to example 1 from 4-fluoro-1-(toluene-4-sulfonyl)-piperidine-4-carboxylic acid (0.2 g), 4-isopropxy-aniline (0.1 g) to give the desired 4-fluoro-1-(toluene-4-sulfonyl)-piperidine-4-carboxylic acid (4-isopropoxy-phenyl)-amide (0.112 g) as an off-white solid. MS (ESI): 435.3 (MH$^+$).

EXAMPLE 20

1-(Toluene-4-sulfonyl)-piperidine-4-carboxylic acid (4-cyclopropylmethoxy-phenyl)-amide

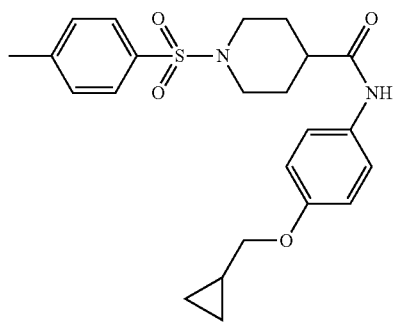

This material was obtained in analogy to example 1 from 1-[(4-Methylphenyl)sulfonyl]-4-piperidinecarboxylic acid (0.142 g), 4-cyclopropylmethoxy-phenylamine (0.098 g) to give the desired 1-(toluene-4-sulfonyl)-piperidine-4-carboxylic acid (4-cyclopropylmethoxy-phenyl)-amide (0.048) as a dark brown solid. MS (ESI): 429.23 (MH$^+$).

EXAMPLE 21

1-(3,3-Dimethyl-butyryl)-piperidine-4-carboxylic acid (4-trifluoromethoxy-phenyl)-amide

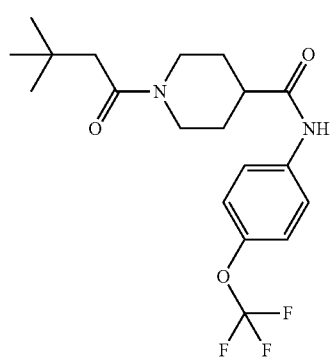

Step A): 4-(4-Trifluoromethoxy-phenylcarbamoyl)-piperidine-1-carboxylic acid tert-butyl ester In analogy to example 8 step A) there was obtained from piperidine-1,4-dicarboxylic acid mono-tert-butyl ester (2.293 g) and 4-trifluoromethoxy-aniline (1.86 g) the desired 4-(4-trifluoromethoxy-phenylcarbamoyl)-piperidine-1-carboxylic acid tert-butyl ester (2.39 g) as an off white solid, which was directly used in the next reaction step.

Step B): Piperidine-4-carboxylic acid (4-trifluoromethoxy-phenyl)-amide

In analogy to example 8 step B) there was obtained from 4-(4-trifluoromethoxy-phenylcarbamoyl)-piperidine-1-carboxylic acid tert-butyl ester (2.35 g) and de-protection with trifluoroacetic acid (5.52 g) in methylene chloride the desired piperidine-4-carboxylic acid (4-trifluoromethoxy-phenyl)-amide (1.3 g) as a light yellow solid that was used directly in the next reaction step.

Step C): 1-(3,3-Dimethyl-butyryl)-piperidine-4-carboxylic acid (4-trifluoromethoxy-phenyl)-amide In analogy to example 8 step C) there was obtained from piperidine-4-carboxylic acid (4-trifluoromethoxy-phenyl)-amide (0.1 g), 3,3-dimethyl-butyric acid (0.041 g) the desired 1-(3,3-dimethyl-butyryl)-piperidine-4-carboxylic acid (4-trifluoromethoxy-phenyl)-amide (0.1 g) as white solid. MS (ESI): 387.19 (MH+).

EXAMPLE 22

1-(Toluene-4-sulfonyl)-piperidine-4-carboxylic acid [4-(2-hydroxy-ethyl)-phenyl]-amide

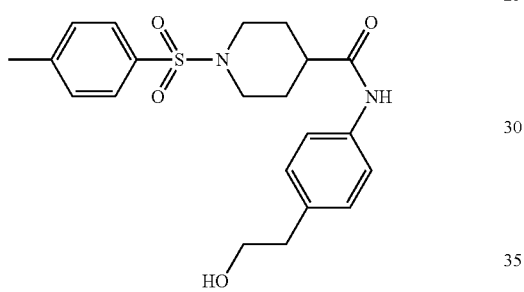

This material was obtained in analogy to example 1 from 1-[(4-methylphenyl)sulfonyl]-4-piperidinecarboxylic acid (0.142 g), 2-(4-amino-phenyl)-ethanol (0.069 g) to give the desired 1-(toluene-4-sulfonyl)-piperidine-4-carboxylic acid [4-(2-hydroxy-ethyl)-phenyl]-amide (0.048) as a white solid. MS (ESI): 403.1 (MH+).

EXAMPLE 23

Racemic Mixture of Example 23a which is (2S,4S)-2-Methoxymethyl-1-(toluene-4-sulfonyl)-piperidine-4-carboxylic acid (4-trifluoromethoxy-phenyl)-amide and Example 23b which is (2R,4R)-2-Methoxymethyl-1-(toluene-4-sulfonyl)-piperidine-4-carboxylic acid (4-trifluoromethoxy-phenyl)-amide

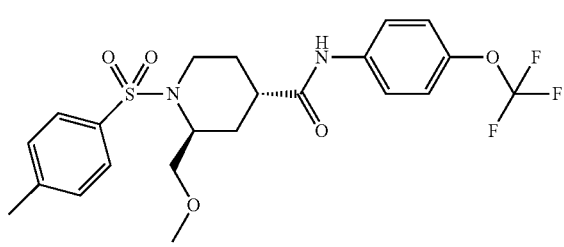

EXAMPLE 23a

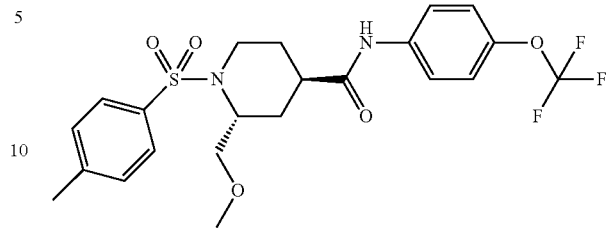

EXAMPLE 23b

This material was obtained by methylation of example 42 (a racemic mixture of example 42a which is (2S,4S)-2-hydroxymethyl-1-(toluene-4-sulfonyl)-piperidine-4-carboxylic acid (4-trifluoromethoxy-phenyl)-amide and 42b which is (2R,4R)-2-hydroxymethyl-1-(toluene-4-sulfonyl)-piperidine-4-carboxylic acid (4-trifluoromethoxy-phenyl)-amide) (0.083 g), with methyl iodide (2.34 g) following the procedure described in example 11 as light yellow oil (26 mg). MS (ESI): 487.25 (MH+).

EXAMPLE 24

1-(2-Chloro-benzenesulfonyl)-4-hydroxymethyl-piperidine-4-carboxylic acid [4-(2,2,2-trifluoro-1-methyl-ethoxy)-phenyl]-amide

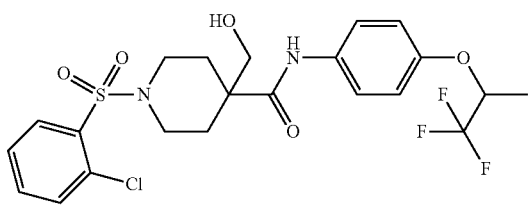

Step A:
4-Benzyloxymethyl-piperidine-1,4-dicarboxylic acid 1-tert-butyl ester 4-ethyl ester To a pre-cooled THF solution under an argon atmosphere was added at −5° C. LDA (2 M, in THF/hepatane/ethylbenzene, 17.5 ml) and then dropwise a solution of piperidine-1,4-dicarboxylic acid 1-tert-butyl ester 4-ethyl ester (5 g) in THF, keeping the temperature at about −7° C. The mixture was stirred 2 hours between −10 and −5° C. then treated slowly and dropwise with benzyl chlormethyl ether (5.47 g) at −5° C. The mixture was stirred 1 hour at 0° C. and 48 h at RT. The solvent was evaporated off, the residue partitioned between AcOEt and water. The layers were separated, the organic layer washed with brine, dried over sodium sulphate and concentrated in vacuo. The residue purified by flash chromatography (AcOEt/heptane, gradient from 0 to 5%) to give the desired 4-Benzyloxymethyl-piperidine-1,4-dicarboxylic acid 1-tert-butyl ester 4-ethyl ester (5.79 g) as a light brown oil. MS (ESI): 378.4 (MH+).

Step B) 4-Benzyloxymethyl-piperidine-4-carboxylic acid ethyl ester

This material was obtained in analogy to example 8B) by de-protection of 4-benzyloxymethyl-piperidine-1,4-dicarboxylic acid 1-tert-butyl ester (3 g) with trifluoroacetic acid (5.35 ml) in methylene chloride (50 ml) to give the desired 4-benzyloxymethyl-piperidine-4-carboxylic acid ethyl ester (2.3 g) as a light brown oil. MS (ESI): 278.2 (MH$^+$).

Step C): 4-Benzyloxymethyl-1-(2-chloro-benzene-sulfonyl)-piperidine-4-carboxylic acid ethyl ester This was obtained in analogy to example 12 step C) from 4-benzyloxymethyl-piperidine-4-carboxylic acid ethyl ester (2.19 g), 2-chloro-benzenesulfonyl chloride (1.667 g) to give the desired 4-benzyloxymethyl-1-(2-chloro-benzenesulfonyl)-piperidine-4-carboxylic acid ethyl ester (2.7 g) as a viscous light yellow oil. MS (ESI): 452.0 (MH$^+$).

Step D): 1-(2-Chloro-benzenesulfonyl)-4-hydroxymethyl-piperidine-4-carboxylic acid [4-(2,2,2-trifluoro-1-methyl-ethoxy)-phenyl]-amide This was obtained in analogy to example 12D) from 4-benzyloxymethyl-1-(2-chloro-benzenesulfonyl)-piperidine-4-carboxylic acid ethyl ester (0.3 g), (rac)-4-(2,2,2-trifluoro-1-methyl-ethoxy)-phenylamine (0.177 g) and dimethylaluminium chloride (2.21 ml, 0.9 molar in heptane) to give the desired 1-(2-chloro-benzenesulfonyl)-4-hydroxymethyl-piperidine-4-carboxylic acid [4-(2,2,2-trifluoro-1-methyl-ethoxy)-phenyl]-amide (0.138 g) as a brown viscous oil. MS (ESI): 521.2 (MH$^+$). (The benzyl group was concurrently cleaved under the reaction conditions applied.)

EXAMPLE 25

(rac)-1-(toluene-4-sulfonyl)-piperidine-4-carboxylic acid [4-(2,2,2-trifluoro-1-methyl-ethoxy)-phenyl]-amide

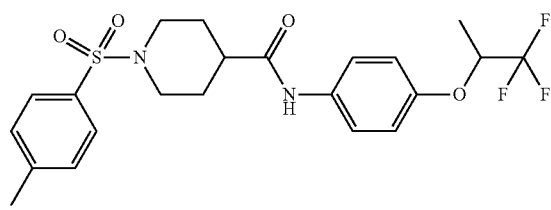

This material was obtained in analogy to example 4 from 1-[(4-methylphenyl)sulfonyl]-4-piperidinecarboxylic acid (0.34 g), (rac)-4-(2,2,2-trifluoro-1-methyl-ethoxy)-phenylamine (0.2 g) to give the desired (rac)-1-(toluene-4-sulfonyl)-piperidine-4-carboxylic acid [4-(2,2,2-trifluoro-1-methyl-ethoxy)-phenyl]-amide (0.25 g) as a light brown crystalline solid. MS (ESI): 470.5 (MH$^+$).

EXAMPLE 26

1-Benzenesulfonyl-4-hydroxymethyl-piperidine-4-carboxylic acid (4-trifluoromethoxy-phenyl)-amide

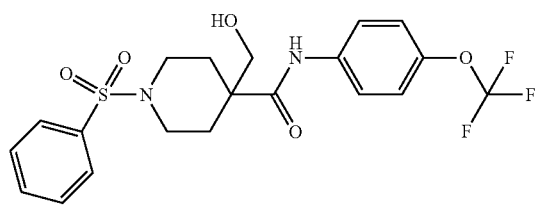

Step A): 4-Benzyloxymethyl-1-(benzenesulfonyl)-piperidine-4-carboxylic acid ethyl ester This was obtained in analogy to example 12 step C) from 4-benzyloxymethyl-piperidine-4-carboxylic acid ethyl ester (2.19 g), benzenesulfonyl
 g) to give the desired 4-benzyloxymethyl-1-(benzenesulfonyl)-piperidine-4-carboxylic acid ethyl ester (2.46 g) as a viscous light yellow oil. MS (ESI): 418.2 (MH$^+$).

Step B) 1-Benzenesulfonyl-4-hydroxymethyl-piperidine-4-carboxylic acid (4-trifluoromethoxy-phenyl)-amide This material was obtained in analogy to example 12D) from 4-benzyloxymethyl-1-(benzenesulfonyl)-piperidine-4-carboxylic acid ethyl ester (0.3 g), 4-trifluoromethoxy-aniline (0.165 g) and dimethylaluminium chloride (2.4 ml, 0.9 molar in heptane) to give the desired 1-benzenesulfonyl-4-hydroxymethyl-piperidine-4-carboxylic acid (4-trifluoromethoxy-phenyl)-amide (0.1 g) as a light brown solid. MS (ESI): 459.2 (MH$^+$). (The benzyl group was concurrently cleaved under the reaction conditions applied.)

EXAMPLE 27

(rac)-1-Benzenesulfonyl-4-hydroxymethyl-piperidine-4-carboxylic acid [4-(2,2,2-trifluoro-1-methyl-ethoxy)-phenyl]-amide

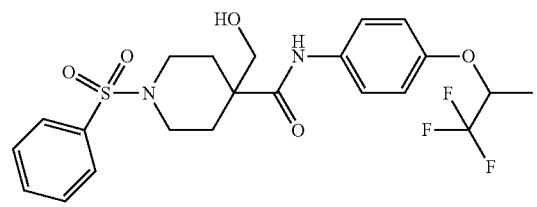

This material was obtained in analogy to example 12D) from 4-benzyloxymethyl-1-(benzenesulfonyl)-piperidine-4-carboxylic acid ethyl ester (0.3 g), ((rac)-4-(2,2,2-trifluoro-1-methyl-ethoxy)-phenylamine (0.192 g) and dimethylaluminium chloride (2.4 ml, 0.9 molar in heptane) to give the desired (rac)-1-benzenesulfonyl-4-hydroxymethyl-piperidine-4-carboxylic acid [4-(2,2,2-trifluoro-1-methyl-ethoxy)-phenyl]-amide (0.142 g) as a light yellow solid. MS (ESI): 487.3 (MH⁺). (The benzyl group was concurrently cleaved under the reaction conditions applied.)

EXAMPLE 28

1-(2-Chloro-benzenesulfonyl)-4-hydroxymethyl-piperidine-4-carboxylic acid (4-trifluoromethoxy-phenyl)-amide

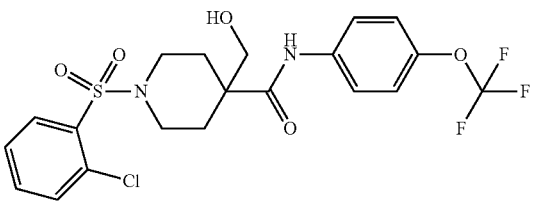

This material was obtained in analogy to example 12D) from 4-benzyloxymethyl-1-(2-chloro-benzenesulfonyl)-piperidine-4-carboxylic acid ethyl ester (0.3 g), 4-trifluoromethoxy-aniline (0.153 g) and dimethylaluminium chloride (2.21 ml, 0.9 molar in heptane) to give the desired 1-(2-chloro-benzenesulfonyl)-4-hydroxymethyl-piperidine-4-carboxylic acid (4-trifluoromethoxy-phenyl)-amide (0.1 g) as a orange viscous oil. MS (ESI): 493.2 (MH⁺). (The benzyl group was concurrently cleaved under the reaction conditions applied.).

EXAMPLE 29

4-Fluoro-1-(4-methoxy-benzenesulfonyl)-piperidine-4-carboxylic acid (4-trifluoromethoxy-phenyl)-amide

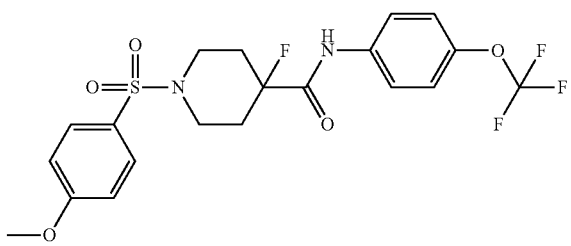

Step A): 4-Fluoro-4-(4-trifluoromethoxy-phenylcarbamoyl)-piperidine-1-carboxylic acid tert-butyl ester In analogy to example 1 from 4-fluoro-piperidine-1,4-dicarboxylic acid mono-tert-butyl ester (0.565 g), synthesis described in WO2008/98977, and 4-trifluoromethoxy-aniline (0.405 g) there as obtained 4-fluoro-4-(4-trifluoromethoxy-phenylcarbamoyl)-piperidine-1-carboxylic acid tert-butyl ester (0.64 g) as an off white solid. MS (ESI): 405.1 ([M-H]⁻).

Step B) 4-Fluoro-piperidine-4-carboxylic acid (4-trifluoromethoxy-phenyl)-amide

In analogy to example 8B) this material was obtained by de-protection of 4-fluoro-4-(4-trifluoromethoxy-phenylcarbamoyl)-piperidine-1-carboxylic acid tert-butyl ester (0.684 g) with trifluoroacetic acid (0.73 ml) in methylene chloride (70 ml) to give 4-fluoro-piperidine-4-carboxylic acid (4-trifluoromethoxy-phenyl)-amide (0.439 g) as a white solid. MS (ESI): 307.1 (MH⁺).

Step C): 4-Fluoro-1-(4-methoxy-benzenesulfonyl)-piperidine-4-carboxylic acid (4-trifluoromethoxy-phenyl)-amide 4-Fluoro-piperidine-4-carboxylic acid (4-trifluoromethoxy-phenyl)-amide (0.1 g) and 4-methoxybenzenesulfonyl chloride (0.067 g) were dissolved in pyridine (10 ml) at RT and under an argon atmosphere and stirred for 24 h at RT. The solvent was evaporated off, the residue was absorbed on silica gel and purified by flash chromatography (AcOEt/heptane, gradient from 0 to 25%) to give the desired 4-fluoro-1-(4-methoxy-benzenesulfonyl)-piperidine-4-carboxylic acid (4-trifluoromethoxy-phenyl)-amide (0.075 g) as a white solid. MS (ESI): 475.1 (MH⁺).

EXAMPLE 30

1-(2-Chloro-benzenesulfonyl)-4-fluoro-piperidine-4-carboxylic acid (4-trifluoromethoxy-phenyl)-amide

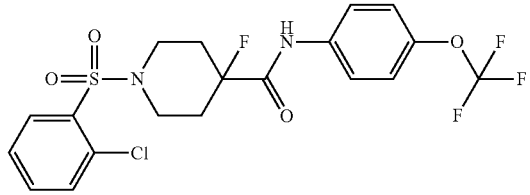

In analogy to example 29 step C) from 4-fluoro-piperidine-4-carboxylic acid (4-trifluoromethoxy-phenyl)-amide (0.1 g) and 2-chlorobenzenesulfonyl chloride (0.069 g) there was obtained 1-(2-chloro-benzenesulfonyl)-4-fluoro-piperidine-4-carboxylic acid (4-trifluoromethoxy-phenyl)-amide (0.125 g) a white solid. MS (ESI): 479.1 (MH⁺).

EXAMPLE 31

4-Methyl-1-(toluene-4-sulfonyl)-piperidine-4-carboxylic acid (4-trifluoromethoxy-phenyl)-amide

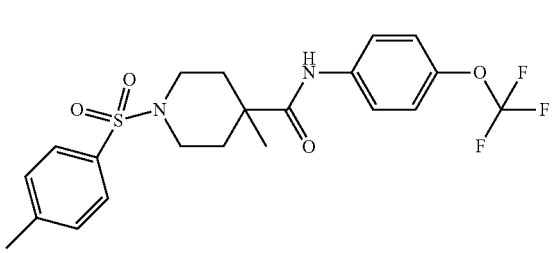

Step A): 4-Methyl-4-(4-trifluoromethoxy-phenylcarbamoyl)-piperidine-1-carboxylic acid tert-butyl ester In analogy to example 1 from 4-methyl-piperidine-1,4-dicarboxylic acid mono-tert-butyl ester (1.0 g)) and 4-trifluormethoxy-aniline (0.728 g) there was obtained 4-methyl-4-

(4-trifluoromethoxy-phenylcarbamoyl)-piperidine-1-carboxylic acid tert-butyl ester (0.75 g) as a colorless oil. MS (ESI): 401.4 ([M-H]⁻).

Step B): 4-Methyl-piperidine-4-carboxylic acid (4-trifluoromethoxy-phenyl)-amide In analogy to example 8B) this material was obtained by de-protection of 4-methyl-4-(4-trifluoromethoxy-phenylcarbamoyl)-piperidine-1-carboxylic acid tert-butyl ester (0.75 g) with trifluoroacetic acid (0.86 ml) in methylene chloride (70 ml) to give 4-methyl-piperidine-4-carboxylic acid (4-trifluoromethoxy-phenyl)-amide (0.34 g) as a colorless viscous oil. MS (ESI): 303.3 (MH⁺).

Step C: 4-Methyl-1-(toluene-4-sulfonyl)-piperidine-4-carboxylic acid (4-trifluoromethoxy-phenyl)-amide In analogy to example 29 C) there from 4-methyl-piperidine-4-carboxylic acid (4-trifluoromethoxy-phenyl)-amide (0.34 g), p-toluenesulfonyl chloride (0.214 g) there was obtained 4-methyl-1-(toluene-4-sulfonyl)-piperidine-4-carboxylic acid (4-trifluoromethoxy-phenyl)-amide (0.3 g) as a white solid. MS (ESI): 455.3 (MH⁺).

EXAMPLE 32

(rac-4-Fluoro-1-(toluene-4-sulfonyl)-piperidine-4-carboxylic acid [4-(2,2,2-trifluoro-1-methyl-ethoxy)-phenyl]-amide

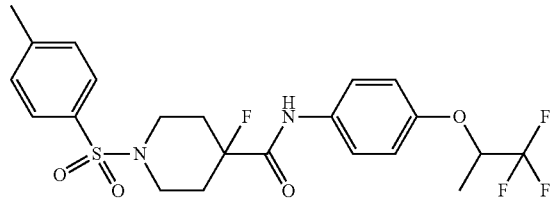

This material was made in analogy to example 1 from 4-fluoro-1-(toluene-4-sulfonyl)-piperidine-4-carboxylic acid (0.15 g), (rac)-4-(2,2,2-trifluoro-1-methyl-ethoxy)-phenylamine (0.102 g) to give the desired (rac)-4-fluoro-1-(toluene-4-sulfonyl)-piperidine-4-carboxylic acid [4-(2,2,2-trifluoro-1-methyl-ethoxy)-phenyl]-amide (0.025 g) as an off-white solid. MS (ESI): 489.25 (MH⁺).

EXAMPLE 33

1-(Toluene-4-sulfonyl)-piperidine-4-carboxylic acid [4-(2,2,2-trifluoro-1,1-dimethyl-ethoxy)-phenyl]-amide

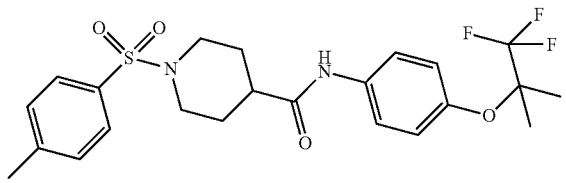

This material was obtained in analogy to example 4 from 1-[(4-methylphenyl)sulfonyl]-4-piperidinecarboxylic acid (0.288 g), 4-(2,2,2-trifluoro-1,1-dimethyl-ethoxy)-phenylamine (0.219 g) to give the desired 1-(toluene-4-sulfonyl)-piperidine-4-carboxylic acid [4-(2,2,2-trifluoro-1,1-dimethyl-ethoxy)-phenyl]-amide (0.376 g) as a light gray crystalline solid. MS (ESI): 485.3 (MH⁺).

Preparation of the Starting Material, 4-(2,2,2-trifluoro-1,1-dimethyl-ethoxy)-phenylamine i) To a solution of 1-fluoro-4-nitro-benzene (2.82 g) and 1,1,1-trifluoro-2-methyl-propan-2-ol (2.3 ml) in DMF (90 ml) under an argon atmosphere was added under ice cooling NaH (0.914 g, 55% suspension in oil) and the mixture was stirred for 3 h at RT. It was then partitioned between diethyl ether and water, the layers were separated, dried over Na₂SO₄ and the solvent was evaporated off to give 1-nitro-4-(2,2,2-trifluoro-1,1-dimethyl-ethoxy)-benzene as a brown oil (4.9 g) that was used in the next step without further purification.

ii) 1-Nitro-4-(2,2,2-trifluoro-1,1-dimethyl-ethoxy)-benzene (4.9 g) in methanol (30 ml) was hydrogenated over Pd/C (10%, 500 mg) at RT and atmospheric for 12 h. The catalyst was filtered off and the solvent removed in vacuo to give the desired 4-(2,2,2-trifluoro-1,1-dimethyl-ethoxy)-phenylamine (4.2 g) as a brown oil that was used without further purification in the next step.

EXAMPLE 34

(rac)-1-(Toluene-4-sulfonyl)-piperidine-4-carboxylic acid [4-(1-cyclopropyl-ethoxy)-phenyl]-amide

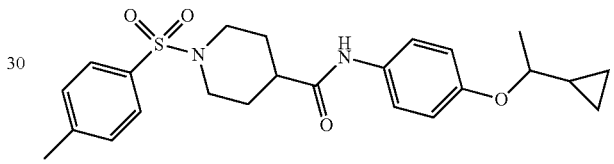

This material was obtained in analogy to example 4 from 1-[(4-methylphenyl)sulfonyl]-4-piperidinecarboxylic acid (0.288 g), (rac)-4-(1-cyclopropyl-ethoxy)-phenylamine (0.18 g) to give the desired (rac)-1-(toluene-4-sulfonyl)-piperidine-4-carboxylic acid [4-(1-cyclopropyl-ethoxy)-phenyl]-amide (0.306 g) as a light gray crystalline solid. MS (ESI): 443.3 (MH⁺).

Preparation of the Starting Material, (rac)-4-(1-cyclopropyl-ethoxy)-phenylamine This was obtained in analogy to the procedure described in example 4 ii), form 1-fluoro-4-nitro-benzene and 1-cyclopropyl-ethanol.

EXAMPLE 35

1-Benzenesulfonyl-piperidine-4-carboxylic acid (1-ethyl-5-trifluoromethyl-1H-pyrazol-3-yl)-amide

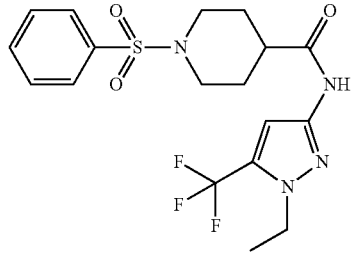

This material was obtained in analogy to example 1 from 1-(phenylsulfonyl)-4-piperidinecarboxylic acid (0.094 g)

and 1-ethyl-5-trifluoromethyl-1H-pyrazol-3-ylamine (0.063 g) to give the desired 1-benzenesulfonyl-piperidine-4-carboxylic acid (1-ethyl-5-trifluoromethyl-1H-pyrazol-3-yl)-amide (0.075 g) as a off-white solid. MS (ESI): 431.13 (MH+).

EXAMPLE 36

Racemic Mixture of Example 36a which is (2S,4S)-1-(2-Chloro-benzenesulfonyl)-2-hydroxymethyl-piperidine-4-carboxylic acid (4-trifluoromethoxy-phenyl)-amide and Example 36b which is (2R,4R)-1-(2-Chloro-benzenesulfonyl)-2-hydroxymethyl-piperidine-4-carboxylic acid (4-trifluoromethoxy-phenyl)-amide

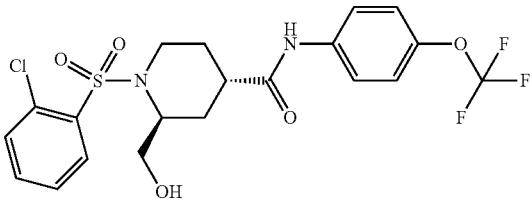

EXAMPLE 36a

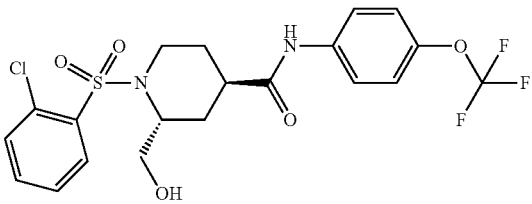

EXAMPLE 36b

Step A): Racemic Mixture of (2S,4S)-1-(2-Chloro-benzenesulfonyl)-piperidine-2,4-dicarboxylic acid 4-methyl ester and (2R,4R)-1-(2-Chloro-benzenesulfonyl)-piperidine-2,4-dicarboxylic acid 4-methyl ester A racemic mixture of (2S,4S)-Piperidine-2,4-dicarboxylic acid 4-methyl ester hydrochloride and (2R,4R)-Piperidine-2,4-dicarboxylic acid 4-methyl ester hydrochloride (0.32 g)—to be prepared by tert. butyl ester cleavage from a mixture of (2S,4S)-piperidine-2,4-dicarboxylic acid 2-tert-butyl ester 4-methyl ester and (2R,4R)-piperidine-2,4-dicarboxylic acid 2-tert-butyl ester 4-methyl ester (for preparation: M Del Bosco, Tetrahedron Vol 51, No 31, pp 8545)—and Na$_2$CO$_3$ (0.425 g) were dissolved in water (10 ml). Then 2-chloro-benzenesulfonyl chloride (0.347 g) was added and the mixture was stirred at RT for 12 h. The reaction mixture was then partitioned between aqueous HCl and AcOEt, the organic layer was separated, dried over sodium sulphate and concentrated in vacuo to give the desired racemic mixture of (2S,4S)-1-(2-Chloro-benzenesulfonyl)-piperidine-2,4-dicarboxylic acid 4-methyl ester and (2R,4R)-1-(2-Chloro-benzenesulfonyl)-piperidine-2,4-dicarboxylic acid 4-methyl ester (0.42 g) as a colorless viscous oil. MS (ESI): 360.2 ([M-H]−).

Step B): Racemic Mixture of (2S,4S)-1-(2-Chloro-benzenesulfonyl)-4-(4-trifluoromethoxy-phenylcarbamoyl)-piperidine-2-carboxylic acid and (2R,4R)-1-(2-Chloro-benzenesulfonyl)-4-(4-trifluoromethoxy-phenylcarbamoyl)-piperidine-2-carboxylic acid A racemic mixture of (2S,4S)-1-(2-Chloro-benzenesulfonyl)-piperidine-2,4-dicarboxylic acid 4-methyl ester and (2R,4R)-1-(2-Chloro-benzenesulfonyl)-piperidine-2,4-dicarboxylic acid 4-methyl ester (0.426 g) was dissolved in toluene (10 ml) under an argon atmosphere at RT. Then 4-trifluoromethoxy-aniline (0.229 g) was added followed by dimethylaluminium chloride in heptane (0.9 molar, 2.88 ml). The mixture was refluxed for 3 hours, cooled to RT and acidified with 3M aqueous HCl upon which insoluble material precipitated out. The mixture was further stirred for 12 h at RT, the solvent was evaporated off, the residue absorbed on silica gel and purified by flash chromatography (MeOH/CH2Cl2, gradient from 0 to 5%) to give the desired racemic mixture of (2S,4S)-1-(2-Chloro-benzenesulfonyl)-4-(4-trifluoromethoxy-phenylcarbamoyl)-piperidine-2-carboxylic acid and (2R,4R)-1-(2-Chloro-benzenesulfonyl)-4-(4-trifluoromethoxy-phenylcarbamoyl)-piperidine-2-carboxylic acid as a viscous oil. MS (ESI): 507.1 (MH+)

Step C): Racemic Mixture of (2S,4S)-1-(2-Chloro-benzenesulfonyl)-2-hydroxymethyl-piperidine-4-carboxylic acid (4-trifluoromethoxy-phenyl)-amide and (2R,4R)-1-(2-Chloro-benzenesulfonyl)-2-hydroxymethyl-piperidine-4-carboxylic acid (4-trifluoromethoxy-phenyl)-amide A racemic mixture of (2S,4S)-1-(2-Chloro-benzenesulfonyl)-4-(4-trifluoromethoxy-phenylcarbamoyl)-piperidine-2-carboxylic acid and (2R,4R)-1-(2-Chloro-benzenesulfonyl)-4-(4-trifluoromethoxy-phenylcarbamoyl)-piperidine-2-carboxylic acid (0.38 g) was dissolved in THF, cooled to 0° C. and borane-THF complex (1 molar in THF, 1.58 ml) was added dropwise under an argon atmosphere. The mixture was stirred for 1 hour at 0° C. and further 12 h at RT. To the mixture was then added 37% HCl (0.2 ml) and stirring was continued for 5 min. The solvent was evaporated off and the residue absorbed on silica gel and purified by flash chromatography (EE/heptane, gradient from 0 to 30%) to give the desired racemic mixture of (2S,4S)-1-(2-Chloro-benzenesulfonyl)-2-hydroxymethyl-piperidine-4-carboxylic acid (4-trifluoromethoxy-phenyl)-amide and (2R,4R)-1-(2-Chloro-benzenesulfonyl)-2-hydroxymethyl-piperidine-4-carboxylic acid (4-trifluoromethoxy-phenyl)-amide (120 mg) as white foam. MS (ESI): 493.08 (MH+).

EXAMPLE 37

1-(Morpholine-4-sulfonyl)-piperidine-4-carboxylic acid (4-trifluoromethoxy-phenyl)-amide

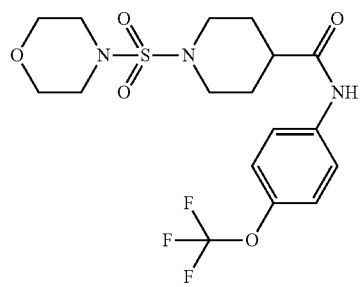

Step A): 1-(Morpholine-4-sulfonyl)-piperidine-4-carboxylic acid ethyl ester

Piperidine-4-carboxylic acid ethyl ester (0.943 g) dissolved in methylene chloride (60 ml) under an argon atmosphere was treated at RT, first with 4-dimethylaminopyridine (1.465 g) then dropwise with morpholine-4-sulfonyl chloride (1.136 g) and the reaction mixture was stirred for 12 h at RT to complete the reaction. The reaction mixture was then partitioned between methylene chloride and aqueous 1N HCL, the layers were separated and the organic layer washed with 2M aqueous $KHCO_3$ then dried over $Na_2SO_4$. The solvent was evaporated off, to give 1-(morpholine-4-sulfonyl)-piperidine-4-carboxylic acid ethyl ester (1.9 g) as a light yellow solid which was directly used in the next step.

Step B): 1-(Morpholine-4-sulfonyl)-piperidine-4-carboxylic acid 1-(Morpholine-4-sulfonyl)-piperidine-4-carboxylic acid ethyl ester (1.9 g) dissolved in methanol (80 ml) was treated at RT with 2M NaOH (15.5 ml) and the mixture was then heated at 85° C. for 12 h. The solvent was then evaporated off, the residue partitioned between methylene chloride and 1N HCL, the layers were separated and the organic layer washed with 2M aqueous $KHCO_3$, dried over $Na_2SO_4$ and concentrated in vacuo to give 1-(morpholine-4-sulfonyl)-piperidine-4-carboxylic acid (1.37 g) as a white solid. MS (ESI): 277.08 ([M-H]$^-$).

Step C): 1-(Morpholine-4-sulfonyl)-piperidine-4-carboxylic acid (4-trifluoromethoxy-phenyl)-amide In analogy to example 1 from 1-(morpholine-4-sulfonyl)-piperidine-4-carboxylic acid (0.097 g) and 4-trifluormethoxy-aniline (0.062 g) there was obtained 1-(morpholine-4-sulfonyl)-piperidine-4-carboxylic acid 4-trifluoromethoxy-phenylamine (0.052 g) as an off white solid. MS (ESI): 438.29 (MH$^+$).

EXAMPLE 38

1-(2-Chloro-benzenesulfonyl)-piperidine-4-carboxylic acid (4-trifluoromethoxy-phenyl)-amide

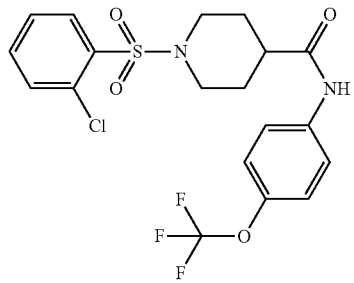

In analogy to example 1 from 1-(2-chloro-benzenesulfonyl)-piperidine-4-carboxylic acid (0.106 g) and 4-trifluoromethoxy-aniline (0.062 g) there was obtained 1-(2-chloro-benzenesulfonyl)-piperidine-4-carboxylic acid (4-trifluoromethoxy-phenyl)-amide (0.082 g) as an off-white solid. MS (ESI): 463.21 (MH$^+$).

EXAMPLE 39

1-(2-Chloro-benzenesulfonyl)-piperidine-4-carboxylic acid (4-isopropoxy-phenyl)-amide

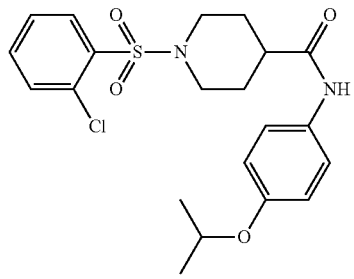

In analogy to example 1 from 1-(2-chloro-benzenesulfonyl)-piperidine-4-carboxylic acid (0.106 g) and 4-isopropoxy-aniline (0.053 g) there was obtained 1-(2-chloro-benzenesulfonyl)-piperidine-4-carboxylic acid (4-isopropoxy-phenyl)-amide (0.116 g) as an off-white solid. MS (ESI): 437.26 (MH$^+$).

EXAMPLE 40

(rac)-1-(2-Chloro-benzenesulfonyl)-piperidine-4-carboxylic acid [4-(2,2,2-trifluoro-1-methyl-ethoxy)-phenyl]-amide

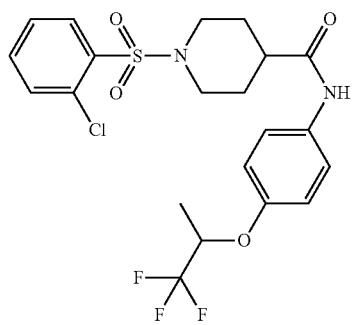

In analogy to example 1 from 1-(2-chloro-benzenesulfonyl)-piperidine-4-carboxylic acid (0.106 g) and (rac)-4-(2,2,2-trifluoro-1-methyl-ethoxy)-phenylamine (0.072 g) there was obtained (rac)-1-(2-chloro-benzenesulfonyl)-piperidine-4-carboxylic acid [4-(2,2,2-trifluoro-1-methyl-ethoxy)-phenyl]-amide (0.135 g) as an off-white solid. MS (ESI): 491.15 (MH+).

EXAMPLE 41

4-Fluoro-1-(toluene-4-sulfonyl)-piperidine-4-carboxylic acid (4-isopropyl-phenyl)-amide

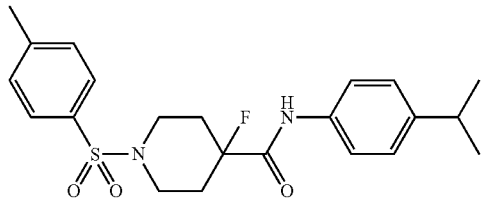

This materiel was made in analogy to example 1 from 4-fluoro-1-(toluene-4-sulfonyl)-piperidine-4-carboxylic acid (0.2 g), 4-isopropyl-aniline (0.09 g) to give the desired 4-fluoro-1-(toluene-4-sulfonyl)-piperidine-4-carboxylic acid (4-isopropoxy-phenyl)-amide (0.047 g) as light brown solid. MS (ESI): 419.3 (MH+).

EXAMPLE 42

Racemic Mixture of Example 42a which is (2S,4S)-2-Hydroxymethyl-1-(toluene-4-sulfonyl)-piperidine-4-carboxylic acid (4-trifluoromethoxy-phenyl)-amide and Example 42b which is (2R,4R)-2-Hydroxymethyl-1-(toluene-4-sulfonyl)-piperidine-4-carboxylic acid (4-trifluoromethoxy-phenyl)-amide

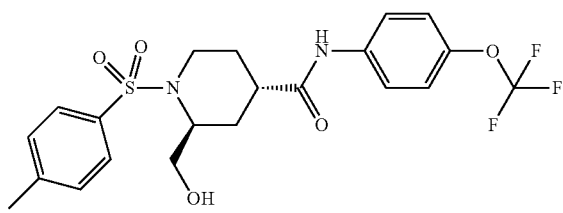

EXAMPLE 42a

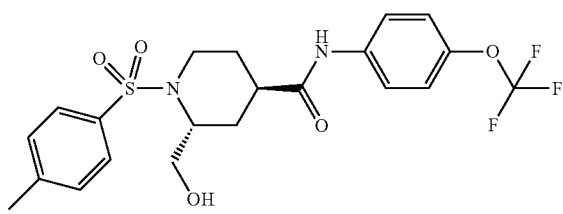

EXAMPLE 42b

Step A): Racemic mixture of (2S,4S)-1-(Toluene-4-sulfonyl)-piperidine-2,4-dicarboxylic acid 4-methyl ester and (2R,4R)-1-(Toluene-4-sulfonyl)-piperidine-2,4-dicarboxylic acid 4-methyl ester In analogy to example 36 step A) the desired racemic mixture of (2S,4S)-1-(toluene-4-sulfonyl)-piperidine-2,4-dicarboxylic acid 4-methyl ester and (2R,4R)-1-(toluene-4-sulfonyl)-piperidine-2,4-dicarboxylic acid 4-methyl ester (0.35 g) was obtained from the reaction of a racemic mixture of (2S,4S)-piperidine-2,4-dicarboxylic acid 4-methyl ester hydrochloride and (2R,4R)-piperidine-2,4-dicarboxylic acid 4-methyl ester hydrochloride (0.3 g) with 4-methyl-benzenesulfonyl chloride (0.294 g) as a white solid. MS (ESI): 342.06 (MH+).

Step B): Racemic mixture of (2S,4S)-1-(Toluene-4-sulfonyl)-4-(4-trifluoromethoxy-phenylcarbamoyl)-piperidine-2-carboxylic acid and (2R,4R)-1-(Toluene-4-sulfonyl)-4-(4-trifluoromethoxy-phenylcarbamoyl)-piperidine-2-carboxylic acid In analogy to example 36 step B) the desired racemic mixture of (2S,4S)-1-(toluene-4-sulfonyl)-4-(4-trifluoromethoxy-phenylcarbamoyl)-piperidine-2-carboxylic acid and (2R,4R)-1-(toluene-4-sulfonyl)-4-(4-trifluoromethoxy-phenylcarbamoyl)-piperidine-2-carboxylic acid (0.22 g) was obtained from the reaction of a racemic mixture of (2S,4S)-1-(toluene-4-sulfonyl)-piperidine-2,4-dicarboxylic acid 4-methyl ester and (2R,4R)-1-(toluene-4-sulfonyl)-piperidine-2,4-dicarboxylic acid 4-methyl ester (0.392 g) with 4-trifluoromethoxy-aniline (0.264 g) and dimethylaluminium chloride in heptane (0.9 molar, 2.93 ml) as a brown solid. MS (ESI): 487.2 (MH+).

Step C): Racemic mixture of (2S,4S)-2-Hydroxymethyl-1-(toluene-4-sulfonyl)-piperidine-4-carboxylic acid (4-trifluoromethoxy-phenyl)-amide and (2R,4R)-2-Hydroxymethyl-1-(toluene-4-sulfonyl)-piperidine-4-carboxylic acid (4-trifluoromethoxy-phenyl)-amide In analogy to example 36 step C) the desired racemic mixture of (2S,4S)-2-hydroxymethyl-1-(toluene-4-sulfonyl)-piperidine-4-carboxylic acid (4-trifluoromethoxy-phenyl)-amide and (2R,4R)-2-hydroxymethyl-1-(toluene-4-sulfonyl)-piperidine-4-carboxylic acid (4-trifluoromethoxy-phenyl)-amide (0.09 g) was obtained from the reaction of a racemic mixture of (2S,4S)-1-(toluene-4-sulfonyl)-4-(4-trifluoromethoxy-phenylcarbamoyl)-piperidine-2-carboxylic acid and (2R,4R)-1-(toluene-4-sulfonyl)-4-(4-trifluoromethoxy-phenylcarbamoyl)-piperidine-2-carboxylic acid (0.22 g) and borane-THF complex (1 molar in THF, 0.68 ml) as a white solid. MS (ESI): 473.2 (MH+).

EXAMPLE 43

(rac)-4-Methyl-1-(toluene-4-sulfonyl)-piperidine-4-carboxylic acid [4-(2,2,2-trifluoro-1-methyl-ethoxy)-phenyl]-amide

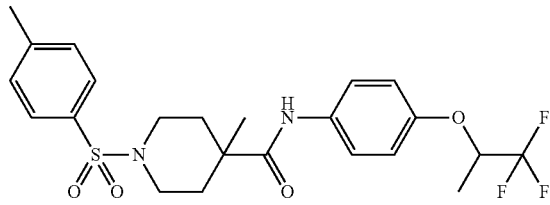

Step A): (rac)-4-Methyl-4-[4-(2,2,2-trifluoro-1-methyl-ethoxy)-phenylcarbamoyl]-piperidine-1-carboxylic acid tert-butyl ester In analogy to example 1 from 4-methyl-piperidine-1,4-dicarboxylic acid mono-tert-butyl ester (0.6 g) and (rac)-4-(2,2,2-trifluoro-1-methyl-ethoxy)-phenylamine (0.506 g) there was obtained (rac)-4-methyl-4-[4-(2,2,2-trifluoro-1-methyl-ethoxy)-phenylcarbamoyl]-piperidine-1-carboxylic acid tert-butyl ester (1.31 g) as a brown solid. MS (ESI): 429.4 ([M-H]−).

Step B): (rac)-4-Methyl-piperidine-4-carboxylic acid [4-(2,2,2-trifluoro-1-methyl-ethoxy)-phenyl]-amide In analogy to example 8B) this material was obtained by de-protection of (rac)-4-methyl-4-[4-(2,2,2-trifluoro-1-methyl-ethoxy)-phenylcarbamoyl]-piperidine-1-carboxylic acid tert-butyl ester (1.31 g) with trifluoroacetic acid (4.57 ml) in methylene chloride (50 ml) to give (rac)-4-methyl-piperidine-4-carboxylic acid [4-(2,2,2-trifluoro-1-methyl-ethoxy)-phenyl]-amide (0.82 g) as a brown oil. MS (ESI): 331.2 (MH+).

Step C: (rac)-4-Methyl-1-(toluene-4-sulfonyl)-piperidine-4-carboxylic acid [4-(2,2,2-trifluoro-1-methyl-ethoxy)-phenyl]-amide In analogy to example 29 C) there from (rac)-4-methyl-piperidine-4-carboxylic acid [4-(2,2,2-trifluoro-1-methyl-ethoxy)-phenyl]-amide (0.8 g), p-toluenesulfonyl chloride (0.46 g) there was obtained (rac)-4-methyl-1-(toluene-4-sulfonyl)-piperidine-4-carboxylic acid [4-(2,2,2-trifluoro-1-methyl-ethoxy)-phenyl]-amide (0.149 g) as a white solid. MS (ESI): 484.53 (MH+).

EXAMPLE 44

(rac)-1-(2-Chloro-benzoyl)-piperidine-4-carboxylic acid [4-(2,2,2-trifluoro-1-methyl-ethoxy)-phenyl]-amide

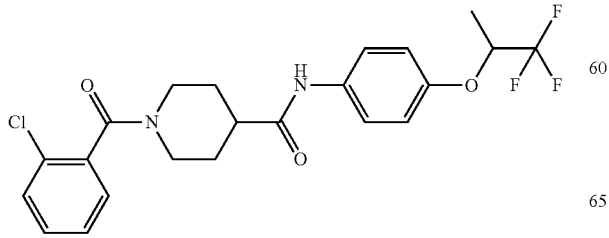

In analogy to example 4 from 1-(2-chloro-benzoyl)-piperidine-4-carboxylic acid (0.267 g) and (rac)-4-(2,2,2-trifluoro-1-methyl-ethoxy)-phenylamine (0.205 g) there was obtained (rac)-1-(2-chloro-benzoyl)-piperidine-4-carboxylic acid [4-(2,2,2-trifluoro-1-methyl-ethoxy)-phenyl]-amide (0.423 g) as crystalline white solid. MS (ESI): 455.3 (MH+).

EXAMPLE 45

(rac)-1-(Toluene-4-sulfonyl)-piperidine-4-carboxylic acid [4-(2,2,2-trifluoro-1-hydroxymethyl-ethoxy)-phenyl]-amide

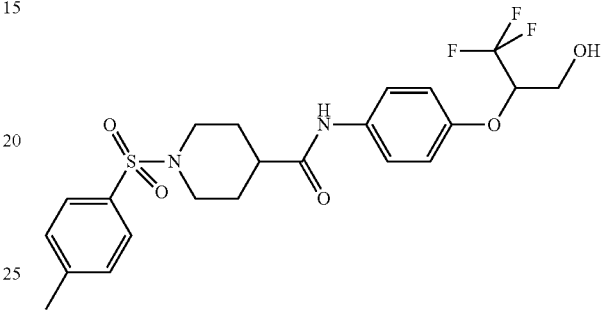

A solution of (rac)-1-(toluene-4-sulfonyl)-piperidine-4-carboxylic acid [4-(2,2,2-trifluoro-1-methoxymethyl-ethoxy)-phenyl]-amide (240 mg), product of example 54) in methylene chloride was treated at RT and under an argon atmosphere with BBr3 (0.5 molar in methylene chloride, 2 ml) and stirred 2 h at RT. The reaction mixture was then taken up in diethyl ether, washed with aqueous 1N HCl, the layers were separated, the organic layer dried over sodium sulfate and evaporated off to give the desired (rac)-1-(toluene-4-sulfonyl)-piperidine-4-carboxylic acid [4-(2,2,2-trifluoro-1-hydroxymethyl-ethoxy)-phenyl]-amide crystalline light red solid. MS (ESI): 487.3 (MH+).

EXAMPLE 46

1-Benzenesulfonyl-piperidine-4-carboxylic acid (4-trifluoromethoxy-phenyl)-amide

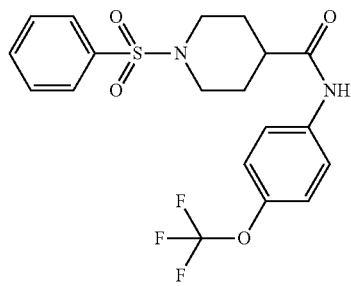

In analogy to example 1 from 1-(phenylsulfonyl)-4-piperidinecarboxylic acid (0.094 g) and 4-trifluoromethoxy-aniline (0.062 g) there was obtained 1-benzenesulfonyl-piperidine-4-carboxylic acid (4-trifluoromethoxy-phenyl)-amide (0.095 g) as white solid. MS (ESI): 429.3 (MH+).

EXAMPLE 47

1-Benzenesulfonyl-piperidine-4-carboxylic acid (4-isopropoxy-phenyl)-amide

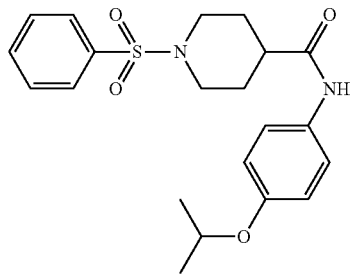

In analogy to example 1 from 1-(phenylsulfonyl)-4-piperidinecarboxylic acid (0.094 g) and 4-isopropoxy-phenylamine (0.053 g)) there was obtained 1-benzenesulfonyl-piperidine-4-carboxylic acid (4-isopropoxy-phenyl)-amide (0.11 g) as white solid. MS (ESI): 403.4 (MH$^+$).

EXAMPLE 48

1-(4-Methoxy-benzenesulfonyl)-piperidine-4-carboxylic acid (4-trifluoromethoxy-phenyl)-amide

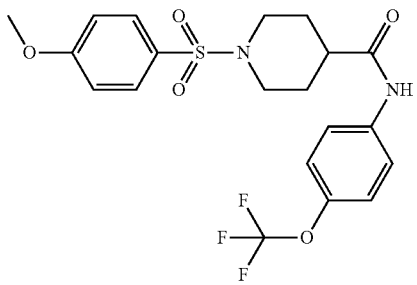

In analogy to example 1 from 1-(4-methoxy-benzenesulfonyl)-piperidine-4-carboxylic acid (0.1 g) and 4-trifluoromethoxy-aniline (0.062 g) there was obtained 1-(4-methoxy-benzenesulfonyl)-piperidine-4-carboxylic acid (4-trifluoromethoxy-phenyl)-amide amide (0.068 g) as white solid. MS (ESI): 459.3 (MH$^+$).

EXAMPLE 49

1-(4-Methoxy-benzenesulfonyl)-piperidine-4-carboxylic acid (4-isopropoxy-phenyl)-amide

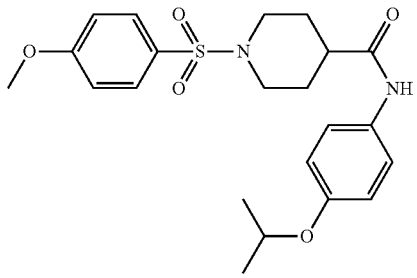

In analogy to example 1 from 1-(4-methoxy-benzenesulfonyl)-piperidine-4-carboxylic acid (0.1 g) and 4-isopropoxy-phenylamine (0.062 g) there was obtained 1-(4-methoxy-benzenesulfonyl)-piperidine-4-carboxylic acid (4-isopropoxy-phenyl)-amide (0.097 g) as white solid. MS (ESI): 431.3 (MH$^+$).

EXAMPLE 50

(rac)-1-Benzenesulfonyl-4-methyl-piperidine-4-carboxylic acid [4-(2,2,2-trifluoro-1,1-dimethyl-ethoxy)-phenyl]-amide

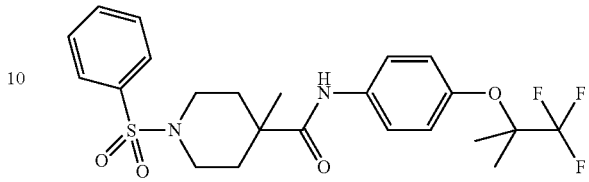

In analogy to example 29 C) from (rac)-4-methyl-piperidine-4-carboxylic acid [4-(2,2,2-trifluoro-1-methyl-ethoxy)-phenyl]-amide (0.3 g), benzenesulfonyl chloride (0.154 g) there was obtained (rac)-4-methyl-1-(toluene-4-sulfonyl)-piperidine-4-carboxylic acid [4-(2,2,2-trifluoro-1-methyl-ethoxy)-phenyl]-amide) (0.164 g) as a white solid. MS (ESI): 485.3 (MH$^+$).

EXAMPLE 51

(4-Hydroxymethyl-1-(toluene-4-sulfonyl)-piperidine-4-carboxylic acid (4-trifluoromethoxy-phenyl)-amide

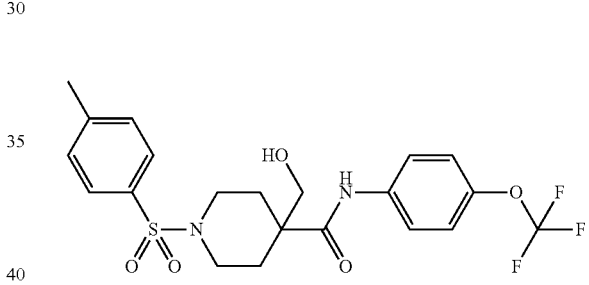

Step A): 4-Benzyloxymethyl-1-(toluene-4-sulfonyl)-piperidine-4-carboxylic acid ethyl ester This was obtained in analogy to example 12 step C) from 4-benzyloxymethyl-piperidine-4-carboxylic acid ethyl ester (2.3 g), p-toluenesulfonyl chloride (1.58 g) to give the desired 4-benzyloxymethyl-1-(toluene-4-sulfonyl)-piperidine-4-carboxylic acid ethyl ester (2.46 g) as a viscous light yellow oil. MS (ESI): 432.3 (MH$^+$).

Step B) (4-Hydroxymethyl-1-(toluene-4-sulfonyl)-piperidine-4-carboxylic acid (4-trifluoromethoxy-phenyl)-amide This was obtained in analogy to example 12D) from 4-benzyloxymethyl-1-(toluene-4-sulfonyl)-piperidine-4-carboxylic acid ethyl ester (0.7 g), 4-trifluoromethoxy-aniline (0.575 g) and dimethylaluminium chloride (4.5 ml, 0.9 molar in heptane) to give the desired (4-hydroxymethyl-1-(toluene-4-sulfonyl)-piperidine-4-carboxylic acid (4-trifluoromethoxy-phenyl)-amide (0.5 g) as a white solid. MS (ESI): 471.1 (MH$^+$). (The benzyl group was concurrently cleaved under the reaction conditions applied.)

EXAMPLE 52

(rac)-1-(Toluene-4-sulfonyl)-piperidine-4-carboxylic acid [4-(3,3,3-trifluoro-2-hydroxy-propoxy)-phenyl]-amide

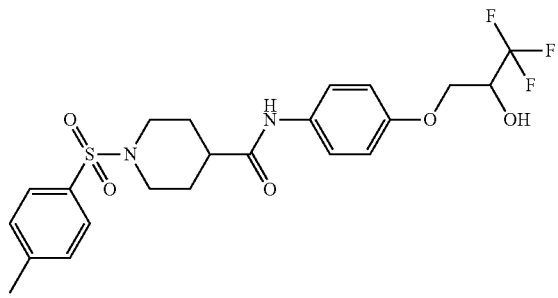

In analogy to example 4 from 1-[(4-methylphenyl)sulfonyl]-4-piperidinecarboxylic acid (0.185 g) and 4-[3,3,3-trifluoro-2-(tetrahydro-pyran-2-yloxy)-propoxy]-phenylamine (0.2 g) and subsequent cleavage of the tetrahydropyranyl protecting group from the crude coupling product with THF/1N HCl (8 ml/2 ml), 20 min at RT, there was obtained (rac)-1-(toluene-4-sulfonyl)-piperidine-4-carboxylic acid [4-(3,3,3-trifluoro-2-hydroxy-propoxy)-phenyl]-amide (0.286 g) as crystalline white solid. MS (ESI): 487.2 (MH$^+$).

Preparation of the Starting Materiel, 4-[3,3,3-trifluoro-2-(tetrahydro-pyran-2-yloxy)-propoxy]-phenylamine This material was obtained according to the procedures described in example 33 steps i,ii) from 1-fluoro-4-nitro-benzene and 3,3,3-trifluoro-2-(tetrahydro-pyran-2-yloxy)-propan-1-ol. 3,3,3-Trifluoro-2-(tetrahydro-pyran-2-yloxy)-propan-1-ol used in the reaction sequence above was obtained from 3,3,3-trifluoro-2-hydroxy-propionic acid methyl ester by, first introduction of the tetrahydropyranyl protecting group (3,4-dihydro-2H-pyran, methylene chloride, RT) and subsequent reduction of the ester group with LiAlH$_4$ in THF, following essentially known literature procedures, to give the desired 3,3,3-trifluoro-2-(tetrahydro-pyran-2-yloxy)-propan-1-ol.

EXAMPLE 53

(rac)-1-(Toluene-4-sulfonyl)-piperidine-4-carboxylic acid [4-(3,3,3-trifluoro-2-methoxy-propoxy)-phenyl]-amide

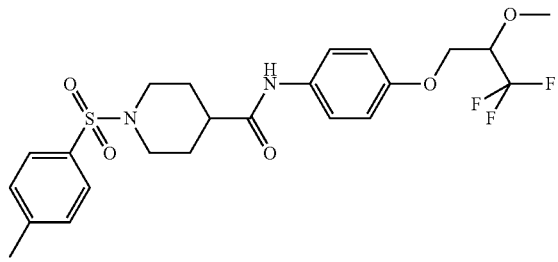

In analogy to example 4 from 1-[(4-Methylphenyl)sulfonyl]-4-piperidinecarboxylic acid (0.144 g) and (rac)-4-(3,3,3-trifluoro-2-methoxy-propoxy)-phenylamine (0.12 g) there was obtained (rac)-1-(toluene-4-sulfonyl)-piperidine-4-carboxylic acid [4-(3,3,3-trifluoro-2-methoxy-propoxy)-phenyl]-amide (0.16 g) as light red crystalline solid. MS (ESI): 501.2 (MH$^+$).

Preparation of the Starting Materiel (rac)-4-(3,3,3-Trifluoro-2-methoxy-propoxy)-phenylamine (a) On reaction of 1-fluoro-4-nitro-benzene and 3,3,3-trifluoro-2-(tetrahydro-pyran-2-yloxy)-propan-1-ol according to the procedure described in example 33 i) there was obtained 2-[2,2,2-trifluoro-1-(4-nitro-phenoxymethyl)-ethoxy]-tetrahydro-pyran. This compound was then treated with THF/1N HCl (20 min RT) to take off the tetrahydropyranyl protecting group and alkylated with methyl iodide in DMF and with NaH as a base at RT (2 h) to give 1-nitro-4-(3,3,3-trifluoro-2-methoxy-propoxy)-benzene, which was then hydrogenated as described in example 33 ii) to give the desired compound, (rac)-4-(3,3,3-trifluoro-2-methoxy-propoxy)-phenylamine.

EXAMPLE 54

(rac)-1-(Toluene-4-sulfonyl)-piperidine-4-carboxylic acid [4-(2,2,2-trifluoro-1-methoxymethyl-ethoxy)-phenyl]-amide

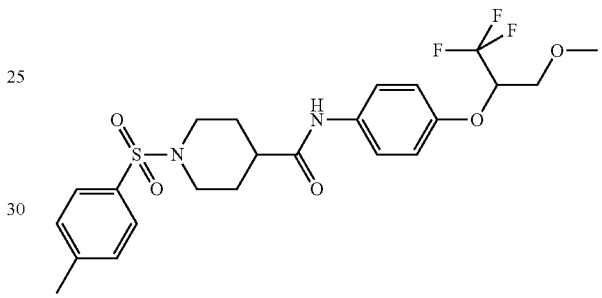

In analogy to example 4 from 1-[(4-methylphenyl)sulfonyl]-4-piperidinecarboxylic acid (0.283 g) and (rac) 4-(2,2,2-trifluoro-1-methoxymethyl-ethoxy)-phenylamine (0.235 g) there was obtained: (rac)-1-(toluene-4-sulfonyl)-piperidine-4-carboxylic acid [4-(2,2,2-trifluoro-1-methoxymethyl-ethoxy)-phenyl]-amide (0.35 g) as light gray crystalline solid. MS (ESI): 501.2 (MH$^+$).

Preparation of the Starting Material, (rac) 4-(2,2,2-trifluoro-1-methoxymethyl-ethoxy)-phenylamine This material was obtained following the procedures described in example 33 i,ii) from 1-fluoro-4-nitro-benzene and (rac)-1,1,1-trifluoro-3-methoxy-propan-2-ol.

EXAMPLE 55

(rac)-4-Hydroxymethyl-1-(toluene-4-sulfonyl)-piperidine-4-carboxylic acid [4-(2,2,2-trifluoro-1-methyl-ethoxy)-phenyl]-amide

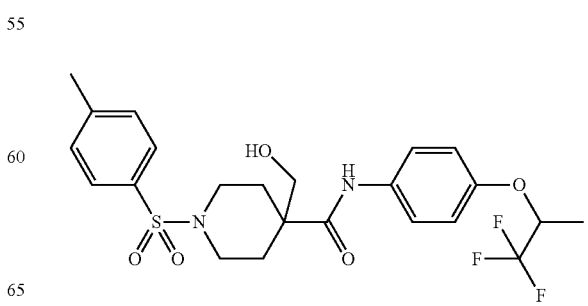

This was obtained in analogy to example 12D) from 4-benzyloxymethyl-1-(toluene-4-sulfonyl)-piperidine-4-carboxylic acid ethyl ester (0.3 g), (rac)-4-(2,2,2-trifluoro-1-methyl-ethoxy)-phenylamine (0.214 g) and dimethylaluminium chloride (1.93 ml, 0.9 molar in heptane) to give the desired (rac)-4-hydroxymethyl-1-(toluene-4-sulfonyl)-piperidine-4-carboxylic acid [4-(2,2,2-trifluoro-1-methyl-ethoxy)-phenyl]-amide (0.2 g) as a light yellow solid. MS (ESI): 499.2 (MH$^+$). (The benzyl group was concurrently cleaved under the reaction conditions applied).

EXAMPLE 56

1-(4,4-Dimethyl-pentanoyl)-piperidine-4-carboxylic acid (4-trifluoromethoxy-phenyl)-amide

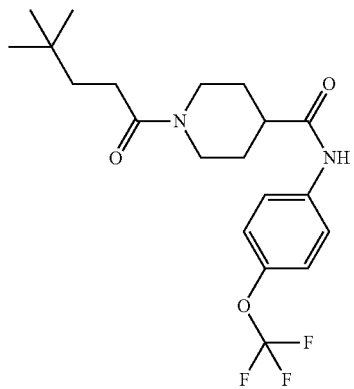

This material was prepared in analogy to example 8 step C) from piperidine-4-carboxylic acid (4-trifluoromethoxy-phenyl)-amide (0.144 g) and 4,4-dimethyl-pentanoic acid (0.065 g) to give the desired 1-(4,4-dimethyl-pentanoyl)-piperidine-4-carboxylic acid (4-trifluoromethoxy-phenyl)-amide (0.178 g) as an off-white solid. MS (ESI): 401.25 (MH$^+$).

EXAMPLE 57

1-Benzenesulfonyl-4-methyl-piperidine-4-carboxylic acid (4-trifluoromethoxy-phenyl)-amide

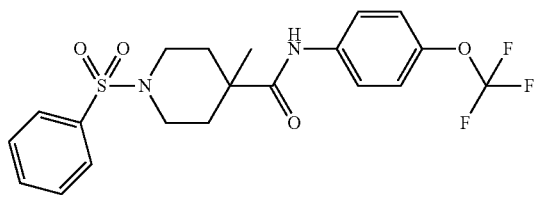

In analogy to example 29 C) there from 4-methyl-piperidine-4-carboxylic acid (4-trifluoromethoxy-phenyl)-amide (0.123 g), benzenesulfonyl chloride (0.072 g) there was obtained 1-benzenesulfonyl-4-methyl-piperidine-4-carboxylic acid (4-trifluoromethoxy-phenyl)-amide (0.1 g) as an off-white solid. MS (ESI): 443.3 (MH$^+$).

EXAMPLE 58

1-(2-Chloro-benzenesulfonyl)-4-methyl-piperidine-4-carboxylic acid (4-trifluoromethoxy-phenyl)-amide

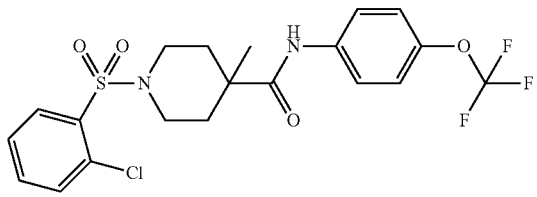

In analogy to example 29 C) there from 4-Methyl-piperidine-4-carboxylic acid (4-trifluoromethoxy-phenyl)-amide (0.123 g), 2-chloro-benzenesulfonyl chloride (0.086 g) there was obtained 1-(2-chloro-benzenesulfonyl)-4-methyl-piperidine-4-carboxylic acid (4-trifluoromethoxy-phenyl)-amide (0.1 g) as an off-white solid. MS (ESI): 477.1 (MH$^+$).

EXAMPLE 59

1-(Toluene-4-sulfonyl)-piperidine-4-carboxylic acid [4-((R)-3-methoxy-1-trifluoromethyl-propoxy)-phenyl]-amide

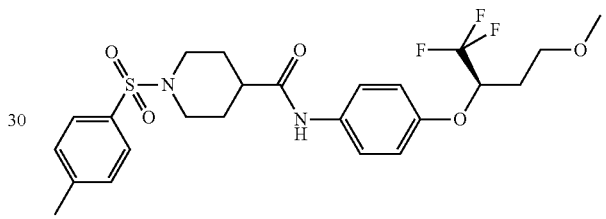

In analogy to example 4 from 1-[(4-methylphenyl)sulfonyl]-4-piperidinecarboxylic acid (0.17 g) and 4-(R)-3-methoxy-1-trifluoromethyl-propoxy)-phenylamine (0.15 g) there was obtained: 1-(toluene-4-sulfonyl)-piperidine-4-carboxylic acid [4-((R)-3-methoxy-1-trifluoromethyl-propoxy)-phenyl]-amide (0.276 g) as white crystalline solid. MS (ESI): 515.3 (MH$^+$).

Preparation of the starting materiel 4-(R)-3-Methoxy-1-trifluoromethyl-propoxy)-phenylamine: This material was obtained on reacting 1-fluoro-4-nitro-benzene and (3R)-1,1,1-trifluoro-4-methoxy-butan-2-ol (lit: patent application JP07242601) according to the procedures described in example 33 i,ii).

EXAMPLE 60

1-(Toluene-4-sulfonyl)-piperidine-4-carboxylic acid [4-((R)-3-hydroxy-1-trifluoromethyl-propoxy)-phenyl]-amide

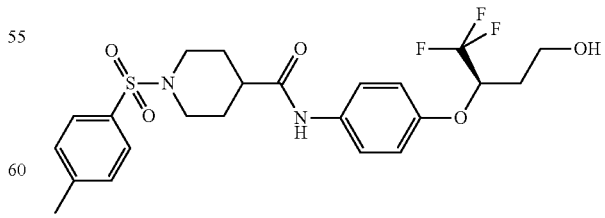

1-(Toluene-4-sulfonyl)-piperidine-4-carboxylic acid [4-((R)-3-methoxy-1-trifluoromethyl-propoxy)-phenyl]-amide (0.105 g), product of example 59), in methylene chloride (2 ml) was treated at RT and under an argon atmosphere with BBr$_3$ (0.5 molar, 1 ml) for 2 h. The mixture was then partitioned between diethyl ether and aqueous 1N HCL, the layers were separated, the organic layer was dried over sodium sulphate, and evaporated off to give the desired 1-(toluene-4-sulfonyl)-piperidine-4-carboxylic acid [4-((R)-3-hydroxy-1-trifluoromethyl-propoxy)-phenyl]-amide (0.073 g) as light brown crystalline solid. MS (ESI): 501.2 (MH⁺).

EXAMPLE 61

1-(2-Chloro-benzenesulfonyl)-piperidine-4-carboxylic acid [1-(4-chloro-phenyl)-cyclopropylmethyl]-amide

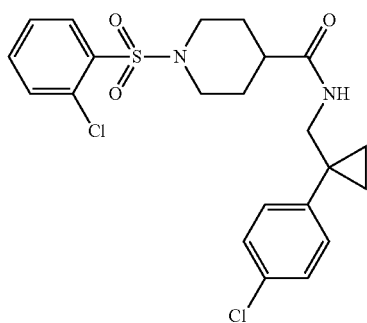

In analogy to example 1 from 1-(2-chloro-benzenesulfonyl)-piperidine-4-carboxylic acid (0.106 g) and C-[1-(4-chloro-phenyl)-cyclopropyl]-methylamine (0.076 g) there was obtained 1-(2-chloro-benzenesulfonyl)-piperidine-4-carboxylic acid [1-(4-chloro-phenyl)-cyclopropylmethyl]-amide (0.1 g) as an white solid. MS (ESI): 467.21 (MH⁺).

EXAMPLE 62

1-Benzenesulfonyl-piperidine-4-carboxylic acid [1-(4-chloro-phenyl)-cyclopropylmethyl]-amide

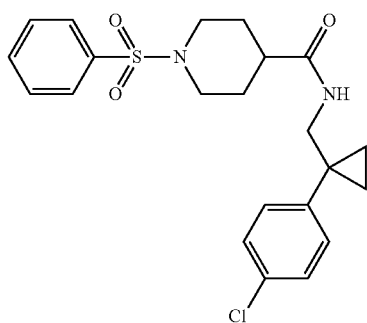

In analogy to example 1 from 1-(phenylsulfonyl)-4-piperidinecarboxylic acid (0.094 g) and C-[1-(4-chloro-phenyl)-cyclopropyl]-methylamine (0.076 g) there was obtained 1-benzenesulfonyl-piperidine-4-carboxylic acid [1-(4-chloro-phenyl)-cyclopropylmethyl]-amide (0.113 g) as a white solid. MS (ESI): 433.22 (MH⁺).

EXAMPLE 63

4-Fluoro-1-(1-methyl-3-trifluoromethyl-1H-pyrazole-4-sulfonyl)-piperidine-4-carboxylic acid (4-trifluoromethoxy-phenyl)-amide

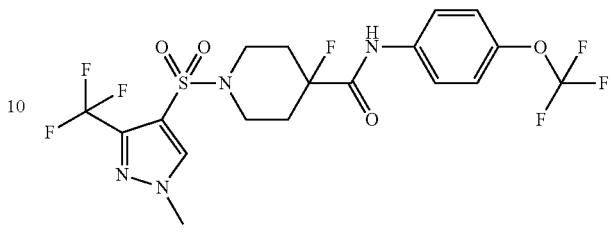

Step A): 4-Fluoro-1-(1-methyl-3-trifluoromethyl-1H-pyrazole-4-sulfonyl)-piperidine-4-carboxylic acid ethyl ester In analogy to example 18A) from 4-fluoro-piperidine-4-carboxylic acid ethyl ester (0.2 g) and 1-methyl-3-trifluoromethyl-1H-pyrazole-4-sulfonyl chloride (0.284 g) there was obtained 4-fluoro-1-(1-methyl-3-trifluoromethyl-1H-pyrazole-4-sulfonyl)-piperidine-4-carboxylic acid ethyl ester (0.37 g) as an orange solid. MS (ESI): 388.1 (MH⁺).

Step B) 4-Fluoro-1-(1-methyl-3-trifluoromethyl-1H-pyrazole-4-sulfonyl)-piperidine-4-carboxylic acid In analogy to example 18B) there was obtained from 4-fluoro-1-(1-methyl-3-trifluoromethyl-1H-pyrazole-4-sulfonyl)-piperidine-4-carboxylic acid ethyl ester (0.21 g) and hydrolysis with aqueous 3N NaOH (1.82 ml) in methanol (20 ml) the desired 4-fluoro-1-(1-methyl-3-trifluoromethyl-1H-pyrazole-4-sulfonyl)-piperidine-4-carboxylic acid (0.198 g) as a light yellow solid. MS (ESI): 358.2 ([M-H]⁻).

Step C): 4-Fluoro-1-(1-methyl-3-trifluoromethyl-1H-pyrazole-4-sulfonyl)-piperidine-4-carboxylic acid (4-trifluoromethoxy-phenyl)-amide This material was made in analogy to example 1 from 4-fluoro-1-(1-methyl-3-trifluoromethyl-1H-pyrazole-4-sulfonyl)-piperidine-4-carboxylic acid (0.176 g) and 4-trifluoromethoxy-aniline (0.087 g) to give the desired 4-fluoro-1-(1-methyl-3-trifluoromethyl-1H-pyrazole-4-sulfonyl)-piperidine-4-carboxylic acid (4-trifluoromethoxy-phenyl)-amide (0.04 g) as a white solid. MS (ESI): 519.28 (MH⁺).

EXAMPLE 64

1-(Toluene-4-sulfonyl)-piperidine-4-carboxylic acid [1-(4-chloro-phenyl)-cyclopropylmethyl]-amide

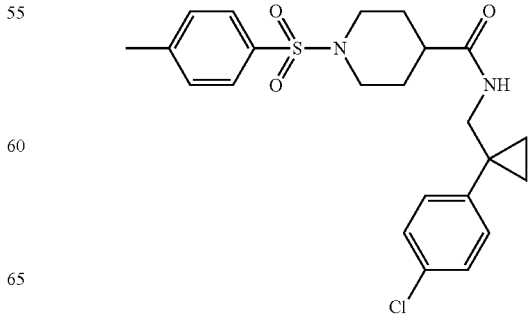

In analogy to example 1 from 1-[(4-methylphenyl)sulfonyl]-4-piperidinecarboxylic acid (0.099 g) and C-[1-(4-chloro-phenyl)-cyclopropyl]-methylamine (0.076 g) there was obtained 1-(toluene-4-sulfonyl)-piperidine-4-carboxylic acid [1-(4-chloro-phenyl)-cyclopropylmethyl]-amide (0.126 g) as a crystalline white solid. MS (ESI): 447.19 (MH⁺).

EXAMPLE A

A compound of formula (I) can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

EXAMPLE B

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:

1. A compound of formula (I),

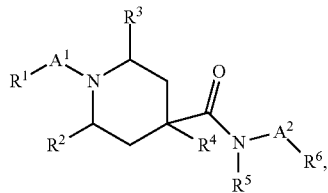

(I)

wherein $R^1$ is selected from the group consisting of: dimethylpropyl, dimethylbutyl, cyclopropylalkyl, pyrazolyl, methyl-trifluoromethyl-1H-pyrazolyl, morpholinyl, phenyl, 2-chlorophenyl, 4-methylphenyl and 4-methoxyphenyl;

$R^2$ is selected from the group consisting of: hydrogen, alkyl, hydroxyalkyl and alkoxyalkyl;

$R^3$ is selected from the group consisting of: hydrogen, alkyl, hydroxyalkyl and alkoxyalkyl;

$R^4$ is selected from the group consisting of: hydrogen, halogen, alkyl, hydroxyalkyl and alkoxyalkyl;

$R^5$ is hydrogen or alkyl;

$R^6$ is selected from the group consisting of: 2,3-dihydrobenzofuranyl, alkylpyridin-3-yl, haloalkoxypyridin-3yl, pyridazinyl, alkoxypyridazinyl, alkyl-trifluoromethyl-1H-pyrazolyl, phenyl and substituted phenyl, wherein substituted phenyl is phenyl substituted in the 4-position with a substituent selected from the group consisting of: chlorine, isopropyl, hydroxyalkyl, isopropoxy, cycloalkylalkoxy, haloalkoxy, haloalkoxyalkyl, alkoxycarbonylalkoxy, carboxyalkoxy, hydroxyalkoxy, alkoxyhaloalkoxy and hydroxyhaloalkoxy; and optionally further substituted in another position with one substituent independently selected from the group consisting of: fluorine, trifluoromethoxy, alkoxycarbonylalkoxy and hydroxyalkoxycarbonyl;

$A^1$ is carbonyl or —S(O)₂—;

$A^2$ is a single bond, —CH₂CH₂— or G;

G is 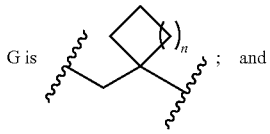 ; and n is zero, 1, 2, 3, 4 or 5;

and pharmaceutically acceptable salts thereof;

with the proviso that, when $R^6$ is phenyl or phenyl substituted in the 4-position with chlorine, $A^2$ is G;

with the further proviso that said compound is not 1-(toluene-4-sulfonyl)-piperidine-4-carboxylic acid (4-trifluoromethoxy-phenyl)-amide; 1-(toluene-4-sulfonyl)-piperidine-4-carboxylic acid [2-(4-difluoromethoxy-phenyl)-ethyl]-amide; 1-benzenesulfonyl-piperidine-4-carboxylic acid (4-isopropyl-phenyl)-amide; 1-(toluene-4-sulfonyl)-piperidine-4-carboxylic acid (4-isopropyl-phenyl)-amide; 1-(4-methoxy-benzenesulfonyl)-piperidine-4-carboxylic acid (4-trifluoromethoxy-phenyl)-amide; 1-benzenesulfonyl-piperidine-4-carboxylic acid (4-trifluoromethoxy-phenyl)-amide; 1-(4-methoxy-benzenesulfonyl)-piperidine-4-carboxylic acid (4-difluoromethoxy-phenyl)-amide; 1-(4-methoxy-benzenesulfonyl)-piperidine-4-carboxylic acid (4-isopropyl-phenyl)-amide; 1-(4-methoxy-benzenesulfonyl)-piperidine-4-carboxylic acid (4-chloro-2-fluoro-phenyl)-amide; 1-benzoyl-piperidine-4-carboxylic acid (4-isopropyl-phenyl)-amide; 1-(2-chloro-benzoyl)-piperidine-4-carboxylic acid (4-isopropyl-phenyl)-amide; 1-benzenesulfonyl-piperidine-4-carboxylic acid (1-phenyl-cyclopropylmethyl)-amide or 1-(toluene-4-sulfonyl)-piperidine-4-carboxylic acid (1-phenyl-cyclopentylmethyl)-amide.

2. A compound according to claim 1, wherein $R^1$ is selected from the group consisting of: dimethylpropyl, phenyl, 2-chlorophenyl and 4-methylphenyl.

3. A compound according to claim 1, wherein $R^1$ is 4-methylphenyl.

4. A compound according to claims 1, wherein n is zero.

5. A compound according to claim 1, wherein $R^2$ is hydrogen or hydroxyalkyl.

6. A compound according to claim 1, wherein $A^1$ is —S(O)₂—.

7. A compound according to claim 1, wherein $A^2$ is a single bond.

8. A compound according to claim 1, wherein $R^6$ is substituted phenyl, wherein substituted phenyl is phenyl substituted in the 4-position with a substituent selected from isopropoxy or haloalkoxy.

9. A compound according to claim 1, wherein $R^6$ is substituted phenyl, wherein substituted phenyl is phenyl substituted in the 4-position with trifluoromethoxy.

10. A compound according to claim 1, selected from the group consisting of:
- 1-Benzenesulfonyl-piperidine-4-carboxylic acid (6-isopropyl-pyridin-3-yl)-amide;
- 1-Benzenesulfonyl-piperidine-4-carboxylic acid (6-methoxy-pyridazin-3-yl)-amide;
- (rac)-1-(Toluene-4-sulfonyl)-piperidine-4-carboxylic acid ethyl-[4-(2,2,2-trifluoro-1-methyl-ethoxy)-phenyl]-amide;
- (rac)-1-(Toluene-4-sulfonyl)-piperidine-4-carboxylic acid methyl-[4-(2,2,2-trifluoro-1-methyl-ethoxy)-phenyl]-amide;
- (rac)-1-(Toluene-4-sulfonyl)-piperidine-4-carboxylic acid [6-(2,2,2-trifluoro-1-methyl-ethoxy) -pyridin-3-yl]-amide;
- 1-(Toluene-4-sulfonyl)-piperidine-4-carboxylic acid (4-isopropoxy-phenyl)-amide;
- 1-(2-Cyclopropyl-acetyl)-piperidine-4-carboxylic acid (4-isopropyl-phenyl)-amide;
- 1-(3-Cyclopropyl-propionyl)-piperidine-4-carboxylic acid (4-isopropyl-phenyl)-amide;
- 1-(3,3-Dimethyl-butyryl)-piperidine-4-carboxylic acid (4-isopropyl-phenyl)-amide;
- (2S,4S)-1-(2-Chloro-benzenesulfonyl)-2-hydroxymethyl-piperidine-4-carboxylic acid methyl-(4-trifluoromethoxy-phenyl)-amide;
- (2R,4R)-1-(2-Chloro-benzenesulfonyl)-2-hydroxymethyl-piperidine-4-carboxylic acid methyl -(4-trifluoromethoxy-phenyl)-amide;
- 1-Benzenesulfonyl-4-(3-methoxy-propyl)-piperidine-4-carboxylic acid (4-isopropoxy-phenyl) -amide;
- 1-(Toluene-4-sulfonyl)-piperidine-4-carboxylic acid (4-difluoromethoxy-phenyl)-amide;
- 1-(Toluene-4-sulfonyl)-piperidine-4-carboxylic acid [4-(2,2,2-trifluoro-ethoxy)-phenyl]-amide;
- 1-(Toluene-4-sulfonyl)-piperidine-4-carboxylic acid (2-fluoro-4-isopropoxy-phenyl)-amide;
- 1-(Toluene-4-sulfonyl)-piperidine-4-carboxylic acid methyl-(4-trifluoromethoxy-phenyl)-amide;
- 1-(Toluene-4-sulfonyl)-piperidine-4-carboxylic acid (2,3-dihydro-benzofuran-5-yl)-amide;
- 4-Fluoro-1-(toluene-4-sulfonyl)-piperidine-4-carboxylic acid (4-trifluoromethoxy-phenyl) -amide;
- 4-Fluoro-1-(toluene-4-sulfonyl)-piperidine-4-carboxylic acid (4-isopropoxy-phenyl)-amide;
- 1-(Toluene-4-sulfonyl)-piperidine-4-carboxylic acid (4-cyclopropylmethoxy-phenyl)-amide;
- 1-(3,3-Dimethyl-butyryl)-piperidine-4-carboxylic acid (4-trifluoromethoxy-phenyl)-amide;
- 1-(Toluene-4-sulfonyl)-piperidine-4-carboxylic acid [4-(2-hydroxy-ethyl)-phenyl]-amide;
- (2S,4S)-2-Methoxymethyl-1-(toluene-4-sulfonyl)-piperidine-4-carboxylic acid (4-trifluoromethoxy-phenyl)-amide;
- (2R,4R)-2-Methoxymethyl-1-(toluene-4-sulfonyl)-piperidine-4-carboxylic acid (4-trifluoromethoxy-phenyl)-amide;
- (rac)-1-(2-Chloro-benzenesulfonyl)-4-hydroxymethyl-piperidine-4-carboxylic acid [4-(2,2,2-trifluoro-1-methyl-ethoxy)-phenyl]-amide;
- (rac)-1-(Toluene-4-sulfonyl)-piperidine-4-carboxylic acid [4-(2,2,2-trifluoro-1-methyl-ethoxy) -phenyl]-amide;
- 1-Benzenesulfonyl-4-hydroxymethyl-piperidine-4-carboxylic acid (4-trifluoromethoxy-phenyl) -amide;
- (rac)-1-benzenesulfonyl-4-hydroxymethyl-piperidine-4-carboxylic acid [4-(2,2,2-trifluoro-1-methyl-ethoxy)-phenyl]-amide;
- 1-(2-Chloro-benzenesulfonyl)-4-hydroxymethyl-piperidine-4-carboxylic acid (4-trifluoromethoxy-phenyl)-amide;
- 4-Fluoro-1-(4-methoxy-benzenesulfonyl)-piperidine-4-carboxylic acid (4-trifluoromethoxy -phenyl)-amide;
- 1-(2-Chloro-benzenesulfonyl)-4-fluoro-piperidine-4-carboxylic acid (4-trifluoromethoxy -phenyl)-amide;
- 4-Methyl-1-(toluene-4-sulfonyl)-piperidine-4-carboxylic acid (4-trifluoromethoxy-phenyl) -amide;
- (rac)-4-Fluoro-1-(toluene-4-sulfonyl)-piperidine-4-carboxylic acid [4-(2,2,2-trifluoro-1-methyl -ethoxy)-phenyl]-amide;
- 1-(Toluene-4-sulfonyl)-piperidine-4-carboxylic acid [4-(2,2,2-trifluoro-1,1-dimethyl-ethoxy) -phenyl]-amide;
- (rac)-1-(Toluene-4-sulfonyl)-piperidine-4-carboxylic acid [4-(1-cyclopropyl-ethoxy)-phenyl]-amide;
- 1-Benzenesulfonyl-piperidine-4-carboxylic acid (1-ethyl-5-trifluoromethyl-1H-pyrazol-3-yl) -amide;
- (2S,4S)-1-(2-Chloro-benzenesulfonyl)-2-hydroxymethyl-piperidine-4-carboxylic acid (4-trifluoromethoxy-phenyl)-amide;
- (2R,4R)-1-(2-Chloro-benzenesulfonyl)-2-hydroxymethyl-piperidine-4-carboxylic acid (4-trifluoromethoxy-phenyl)-amide;
- 1-(Morpholine-4-sulfonyl)-piperidine-4-carboxylic acid (4-trifluoromethoxy-phenyl)-amide;
- 1-(2-Chloro-benzenesulfonyl)-piperidine-4-carboxylic acid (4-trifluoromethoxy-phenyl)-amide;
- 1-(2-Chloro-benzenesulfonyl)-piperidine-4-carboxylic acid (4-isopropoxy-phenyl)-amide;
- (rac)-1-(2-Chloro-benzenesulfonyl)-piperidine-4-carboxylic acid [4-(2,2,2-trifluoro-1-methyl -ethoxy)-phenyl]-amide;
- 4-Fluoro-1-(toluene-4-sulfonyl)-piperidine-4-carboxylic acid (4-isopropyl-phenyl)-amide;
- (2S,4S)-2-Hydroxymethyl-1-(toluene-4-sulfonyl)-piperidine-4-carboxylic acid (4-trifluoromethoxy-phenyl)-amide;
- (2R,4R)-2-Hydroxymethyl-1-(toluene-4-sulfonyl)-piperidine-4-carboxylic acid (4-trifluoromethoxy-phenyl)-amide;
- (rac)-4-Methyl-1-(toluene-4-sulfonyl)-piperidine-4-carboxylic acid [4-(2,2,2-trifluoro-1-methyl -ethoxy)-phenyl]-amide;
- (rac)-1-(2-Chloro-benzoyl)-piperidine-4-carboxylic acid [4-(2,2,2-trifluoro-1-methyl-ethoxy) -phenyl]-amide;
- 1-(Toluene-4-sulfonyl)-piperidine-4-carboxylic acid [4-(2,2,2-trifluoro-1-hydroxymethyl -ethoxy)-phenyl]-amide;
- 1-Benzenesulfonyl-piperidine-4-carboxylic acid (4-isopropoxy-phenyl)-amide;
- 1-(4-Methoxy-benzenesulfonyl)-piperidine-4-carboxylic acid (4-isopropoxy-phenyl)-amide;
- (rac)-1-Benzenesulfonyl-4-methyl-piperidine-4-carboxylic acid [4-(2,2,2-trifluoro-1,1-dimethyl -ethoxy)-phenyl]-amide;
- 4-Hydroxymethyl-1-(toluene-4-sulfonyl)-piperidine-4-carboxylic acid (4-trifluoromethoxy -phenyl)-amide;

(rac)-1-(Toluene-4-sulfonyl)-piperidine-4-carboxylic acid [4-(3,3,3-trifluoro-2-hydroxy -propoxy)-phenyl]-amide;

(rac)-1-(Toluene-4-sulfonyl)-piperidine-4-carboxylic acid [4-(3,3,3-trifluoro-2-methoxy -propoxy)-phenyl]-amide;

(rac)-1-(Toluene-4-sulfonyl)-piperidine-4-carboxylic acid [4-(2,2,2-trifluoro-1-methoxymethyl -ethoxy)-phenyl]-amide;

4-Hydroxymethyl-1-(toluene-4-sulfonyl)-piperidine-4-carboxylic acid [4-(2,2,2-trifluoro-1-methyl-ethoxy)-phenyl]-amide;

1-(4,4-Dimethyl-pentanoyl)-piperidine-4-carboxylic acid (4-trifluoromethoxy-phenyl)-amide;

1-Benzenesulfonyl-4-methyl-piperidine-4-carboxylic acid (4-trifluoromethoxy-phenyl)-amide;

1-(2-Chloro-benzenesulfonyl)-4-methyl-piperidine-4-carboxylic acid (4-trifluoromethoxy -phenyl)-amide;

1-(Toluene-4-sulfonyl)-piperidine-4-carboxylic acid [4-((R)-3-methoxy-1-trifluoromethyl -propoxy)-phenyl]-amide;

1-(Toluene-4-sulfonyl)-piperidine-4-carboxylic acid [4-((R)-3-hydroxy-1-trifluoromethyl -propoxy)-phenyl]-amide;

1-(2-Chloro-benzenesulfonyl)-piperidine-4-carboxylic acid [1-(4-chloro-phenyl) -cyclopropylmethyl]-amide;

1-Benzenesulfonyl-piperidine-4-carboxylic acid [1-(4-chloro-phenyl)-cyclopropylmethyl]-amide;

4-Fluoro-1-(1-methyl-3-trifluoromethyl-1H-pyrazole-4-sulfonyl)-piperidine-4-carboxylic acid (4-trifluoromethoxy-phenyl)-amide; and 1-(Toluene-4-sulfonyl)-piperidine-4-carboxylic acid [1-(4-chloro-phenyl)-cyclopropylmethyl]-amide.

11. A compound according to claim 1, selected from the group consisting of:

1-(Toluene-4-sulfonyl)-piperidine-4-carboxylic acid (4-isopropoxy-phenyl)-amide;

(2S,4S)-1-(2-Chloro-benzenesulfonyl)-2-hydroxymethyl-piperidine-4-carboxylic acid methyl-(4-trifluoromethoxy-phenyl)-amide;

(2R,4R)-1-(2-Chloro-benzenesulfonyl)-2-hydroxymethyl-piperidine-4-carboxylic acid methyl-(4-trifluoromethoxy-phenyl)-amide;

1-(Toluene-4-sulfonyl)-piperidine-4-carboxylic acid methyl-(4-trifluoromethoxy-phenyl)-amide;

1-(3,3-Dimethyl-butyryl)-piperidine-4-carboxylic acid (4-trifluoromethoxy-phenyl)-amide;

1-Benzenesulfonyl-4-hydroxymethyl-piperidine-4-carboxylic acid (4-trifluoromethoxy-phenyl) -amide;

1-(2-Chloro-benzenesulfonyl)-4-fluoro-piperidine-4-carboxylic acid (4-trifluoromethoxy -phenyl)-amide;

(rac)-1-(2-Chloro-benzenesulfonyl)-piperidine-4-carboxylic acid [4-(2,2,2-trifluoro-1-methyl -ethoxy)-phenyl]-amide;

(2S,4S)-2-Hydroxymethyl-1-(toluene-4-sulfonyl)-piperidine-4-carboxylic acid (4-trifluoromethoxy-phenyl)-amide;

(2R,4R)-2-Hydroxymethyl-1-(toluene-4-sulfonyl)-piperidine-4-carboxylic acid (4-trifluoromethoxy-phenyl)-amide; and 1-Benzenesulfonyl-4-methyl-piperidine-4-carboxylic acid (4-trifluoromethoxy-phenyl)-amide.

12. A compound selected from the group consisting of: 1-(toluene-4-sulfonyl)-piperidine-4-carboxylic acid (4-trifluoromethoxy-phenyl)-amide, 1-(toluene-4-sulfonyl)-piperidine-4-carboxylic acid [2-(4-difluoromethoxy-phenyl)-ethyl]-amide, 1-benzenesulfonyl-piperidine-4-carboxylic acid (4-isopropyl-phenyl)-amide, 1-(toluene-4-sulfonyl)-piperidine-4-carboxylic acid (4-isopropyl-phenyl)-amide, 1-(4-methoxy -benzenesulfonyl)-piperidine-4-carboxylic acid (4-trifluoromethoxy-phenyl)-amide, 1-benzenesulfonyl-piperidine-4-carboxylic acid (4-trifluoromethoxy-phenyl)-amide, 1-(4-methoxy-benzenesulfonyl)-piperidine-4-carboxylic acid (4-difluoromethoxy-phenyl)-amide, 1-(4-methoxy-benzenesulfonyl)-piperidine-4-carboxylic acid (4-isopropyl-phenyl)-amide, 1-(4-methoxy-benzenesulfonyl)-piperidine-4-carboxylic acid (4-chloro-2-fluoro-phenyl)-amide, 1-benzoyl-piperidine-4-carboxylic acid (4-isopropyl-phenyl)-amide, 1-(2-chloro-benzoyl) -piperidine-4-carboxylic acid (4-isopropyl-phenyl)-amide, 1-benzenesulfonyl-piperidine-4-carboxylic acid (1-phenyl-cyclopropylmethyl)-amide and 1-(toluene-4-sulfonyl)-piperidine-4-carboxylic acid (1-phenyl-cyclopentylmethyl)-amide.

13. A pharmaceutical composition comprising a therapeutically inert carrier and a compound according to claim 1.

* * * * *